US012619152B2

(12) United States Patent
Miyoshi et al.

(10) Patent No.: US 12,619,152 B2
(45) Date of Patent: May 5, 2026

(54) METHOD FOR PRODUCING ACTINIC RAY-SENSITIVE OR RADIATION-SENSITIVE RESIN COMPOSITION, PATTERN FORMING METHOD, METHOD FOR PRODUCING ELECTRONIC DEVICE, AND METHOD FOR PRODUCING ONIUM SALT

(71) Applicant: FUJIFILM Corporation, Tokyo (JP)

(72) Inventors: Taro Miyoshi, Shizuoka (JP); Shuhei Yamaguchi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 740 days.

(21) Appl. No.: 17/884,181

(22) Filed: Aug. 9, 2022

(65) Prior Publication Data

US 2023/0123203 A1 Apr. 20, 2023

(30) Foreign Application Priority Data

Aug. 31, 2021 (JP) ................................. 2021-142005
Dec. 10, 2021 (JP) ................................. 2021-201240
Jun. 22, 2022 (JP) ................................. 2022-100729

(51) Int. Cl.

| | |
|---|---|
| ***G03F 7/26*** | (2006.01) |
| ***C07C 51/41*** | (2006.01) |
| ***C07C 381/12*** | (2006.01) |
| ***C08F 212/14*** | (2006.01) |
| ***C08F 220/30*** | (2006.01) |
| ***G03F 7/004*** | (2006.01) |
| ***G03F 7/038*** | (2006.01) |
| ***G03F 7/039*** | (2006.01) |

(52) U.S. Cl.

CPC .............. *G03F 7/26* (2013.01); *C07C 51/412* (2013.01); *C07C 381/12* (2013.01); *C08F 212/24* (2020.02); *C08F 220/301* (2020.02); *G03F 7/0045* (2013.01); *G03F 7/038* (2013.01); *G03F 7/039* (2013.01); *G03F 7/0392* (2013.01); *G03F 7/0397* (2013.01)

(58) Field of Classification Search

CPC ........ G03F 7/26; C07C 51/412; C07C 381/12
See application file for complete search history.

(56) References Cited

U.S. PATENT DOCUMENTS

| | | | | |
|---|---|---|---|---|
| 6,344,307 | B1 * | 2/2002 | Kojima | C08F 2/48 522/31 |
| 7,220,879 | B2 | 5/2007 | Bass et al. | |
| 7,759,045 | B2 | 7/2010 | Akita et al. | |
| 11,156,917 | B2 | 10/2021 | Sakita et al. | |
| 2009/0004601 | A1 | 1/2009 | Akita et al. | |
| 2012/0082936 | A1 | 4/2012 | Serizawa et al. | |
| 2015/0198876 | A1 * | 7/2015 | Domon | C07C 61/29 430/326 |
| 2015/0355539 | A1 | 12/2015 | Namai | |

FOREIGN PATENT DOCUMENTS

| | | | | |
|---|---|---|---|---|
| CN | 1762965 | A | 4/2006 | |
| CN | 101334588 | A | 12/2008 | |
| JP | 2001-125277 | A | 5/2001 | |
| JP | 2009-8788 | A | 1/2009 | |
| TW | 201837018 | A | 10/2018 | |
| WO | 99/54788 | A1 | 10/1999 | |
| WO | WO-2006096578 | A1 * | 9/2006 | C07C 211/62 |
| WO | 2010/147079 | A1 | 12/2010 | |
| WO | 2014/188762 | A1 | 11/2014 | |
| WO | WO-2020175495 | A1 * | 9/2020 | C07C 319/24 |

OTHER PUBLICATIONS

Office Action issued on Aug. 8, 2025 by the Taiwan Intellectual Property Office in corresponding Taiwanese Patent Application No. 111130122.

Office Action issued on Nov. 26, 2025 by the Taiwan Intellectual Property Office in corresponding Taiwanese Patent Application No. 111130122.

Communication dated Jan. 20, 2026, issued by the Japanese Patent Office in Japanese Application No. 2022-100729.

Office Action dated Feb. 5, 2026, issued by Korean Patent Office in Korean Patent Application No. 10-2022-0106596.

* cited by examiner

*Primary Examiner* — Amanda C. Walke

(74) *Attorney, Agent, or Firm* — Sughrue Mion, PLLC

(57) ABSTRACT

A method for producing an actinic ray-sensitive or radiation-sensitive resin composition, the method including passing a solution including an acid compound having a pKa of 2.0 or more through a column packed with an ion-exchange resin, producing an onium salt by using the acid compound having been passed through the column, and mixing together the onium salt and a resin that undergoes an increase in polarity due to action of acid.

15 Claims, No Drawings

METHOD FOR PRODUCING ACTINIC RAY-SENSITIVE OR RADIATION-SENSITIVE RESIN COMPOSITION, PATTERN FORMING METHOD, METHOD FOR PRODUCING ELECTRONIC DEVICE, AND METHOD FOR PRODUCING ONIUM SALT

CROSS-REFERENCE TO RELATED APPLICATIONS

The present application is based on and claims priority under 35 U.S.C. § 119 from Japanese Patent Applications No. 2021-142005 filed on Aug. 31, 2021, No. 2021-201240 filed on Dec. 10, 2021, and No. 2022-100729 filed on Jun. 22, 2022, the contents of which are incorporated herein by reference.

BACKGROUND OF THE INVENTION

1. Field of the Invention

The present invention relates to a method for producing an actinic ray-sensitive or radiation-sensitive resin composition, a pattern forming method, a method for producing an electronic device, and a method for producing an onium salt. More specifically, the present invention relates to a method for producing an actinic ray-sensitive or radiation-sensitive resin composition suitably used for ultra-micro lithography processes applicable to fabrication processes of ultra-LSI (Large Scale Integration) and high-capacity microchips, nanoimprint mold formation processes, high-density data recording medium production processes, and the like and other photofabrication processes, a pattern forming method, a method for producing an electronic device, and a method for producing an onium salt.

2. Description of the Related Art

In the related art, in the fabrication processes for semiconductor devices such as ICs (Integrated Circuits) and LSIs, lithographic microprocessing using photoresist compositions has been performed. In recent years, with an increase in the degree of integration of integrated circuits, formation of ultrafine patterns in the submicron range or the quarter micron range has come to be in demand. With this, there is also a trend for exposure wavelengths toward shorter wavelengths from the g-line to the i-line further to KrF excimer laser light; currently, exposure apparatuses using, as light sources, ArF excimer laser having the wavelength of 193 nm have been developed. In addition, as a technique of further increasing the resolving power, a technique in which the space between a projection lens and a sample is filled with a liquid having a high refractive index (hereafter, also referred to as “immersion liquid”), what is called, the immersion method has been developed.

In addition, currently, lithography using, instead of excimer laser light, an electron beam (EB), X-rays, extreme ultraviolet rays (EUV), or the like has also been developed. With this, chemical amplification resist compositions that are effectively sensitive to various radiations and have high sensitivity and high resolution have been developed.

For actinic ray-sensitive or radiation-sensitive resin compositions such as resist compositions, onium salts are often used. For example, WO99/54788A describes a resist composition including a resin having an aprotic onium salt.

WO99/54788A describes a method for producing an aprotic onium salt compound having a hydroxyl anion by passing an aqueous solution of an aprotic onium salt compound having an acetate anion, through an anion-exchange resin, to exchange the acetate anion with a hydroxyl anion.

SUMMARY OF THE INVENTION

The inventors of the present invention performed studies and have found the following: in the case of using, for a resist composition, of onium salts, in particular, an onium salt including an anion whose a conjugate acid has a pKa of 2.0 or more, a resist pattern formed on a member to be processed such as a silicon wafer and etched tends to have large line width roughness (Line Width Roughness: LWR).

Thus, a resist composition that includes an onium salt including an anion whose conjugate acid has a pKa of 2.0 or more and that has high post-etching LWR performance is in demand. The LWR performance means the performance of providing a pattern having a smaller LWR.

An object of the present invention is to provide a method for producing an actinic ray-sensitive or radiation-sensitive resin composition that includes an onium salt including an anion whose conjugate acid has a pKa of 2.0 or more and that has high post-etching LWR performance. Another object of the present invention is to provide a pattern forming method and a method for producing an electronic device that use the method for producing an actinic ray-sensitive or radiation-sensitive resin composition, and a method for producing the onium salt.

The inventors of the present invention studied the above-described objects and have found the following: for the purpose of purifying an onium salt including an anion whose conjugate acid has a pKa of 2.0 or more, subjecting the onium salt to passing through an ion-exchange resin or washing using acid causes, in addition to purification, protonation, which leads to degradation of the post-etching LWR performance.

They also have found the following: a solution including an acid compound having a pKa of 2.0 or more is passed through a column packed with an ion-exchange resin and the acid compound having been passed through the column is used to produce an onium salt, to thereby suppress protonation and achieve purification, to achieve the above-described objects.

The inventors of the present invention have found that the following features enable achievement of the above-described objects.

[1]

A method for producing an actinic ray-sensitive or radiation-sensitive resin composition, the method including:

- a step (1) of passing a solution including an acid compound (CA) having a pKa of 2.0 or more, through a column packed with an ion-exchange resin;
- a step (2) of using the acid compound (CA) having been passed through the column to produce an onium salt (C); and
- a step (3) of mixing together the onium salt (C) and a resin (A) that undergoes an increase in polarity due to action of acid.

[2]

The method for producing an actinic ray-sensitive or radiation-sensitive resin composition according to [1], wherein the ion-exchange resin has, as an ion-exchange group, a strongly acidic cation-exchange group.

[3]

The method for producing an actinic ray-sensitive or radiation-sensitive resin composition according to [2], wherein the strongly acidic cation-exchange group is a sulfonic group.

[4]

The method for producing an actinic ray-sensitive or radiation-sensitive resin composition according to any one of [1] to [3], wherein the acid compound (CA) has a pKa of 3.0 or more.

[5]

The method for producing an actinic ray-sensitive or radiation-sensitive resin composition according to any one of [1] to [4], wherein the acid compound (CA) is a carboxylic acid or a phenol.

[6]

The method for producing an actinic ray-sensitive or radiation-sensitive resin composition according to any one of [1] to [4], wherein the acid compound (CA) is a compound represented by General formula (CA1) or (CA2) below.

(CA1)

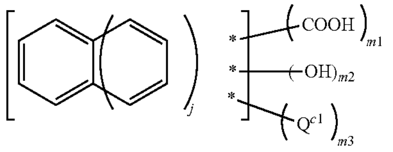

In General formula (CA1), j represents 0 or 1, $Q^{C1}$ represents a substituent, m1 and m2 each independently represent 0 or 1, m3 represents an integer of 0 or more and (6+2j−m1−m2) or less, a sum of m1 and m2 is 1 or 2, and

*'s each represent a direct bond connecting to the aromatic hydrocarbon described in General formula (CA1).

(CA2)

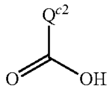

In General formula (CA2), $Q^{C2}$ represents an alkyl group or a cycloalkyl group.

[7]

The method for producing an actinic ray-sensitive or radiation-sensitive resin composition according to any one of [1] to [6], wherein a value provided by subtracting, from the pKa of the acid compound (CA), a pKa of an ion-exchange group of the ion-exchange resin is 3.0 or more.

[8]

The method for producing an actinic ray-sensitive or radiation-sensitive resin composition according to any one of [1] to [7], wherein the ion-exchange resin has a degree of crosslinking of 10% or less.

[9]

The method for producing an actinic ray-sensitive or radiation-sensitive resin composition according to any one of [1] to [8], wherein the actinic ray-sensitive or radiation-sensitive resin composition includes the onium salt (C) in an amount of 10 mass % or more relative to a total solid content.

[10]

The method for producing an actinic ray-sensitive or radiation-sensitive resin composition according to any one of [1] to [9], wherein the actinic ray-sensitive or radiation-sensitive resin composition further contains a compound (B) that generates acid in response to irradiation with an actinic ray or radiation, and the actinic ray-sensitive or radiation-sensitive resin composition has a mass-based content $A_C$ of the onium salt (C) and a mass-based content $A_B$ of the compound (B), and satisfies $A_C$:$A_B$=1.4 to 4:1.

[11]

The method for producing an actinic ray-sensitive or radiation-sensitive resin composition according to any one of [1] to [10], wherein the resin (A) has at least one selected from the group consisting of a repeating unit represented by General formula (A1) below, a repeating unit represented by General formula (A2) below, and a repeating unit represented by General formula (A3) below.

(A1)

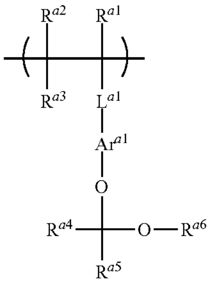

(A2)

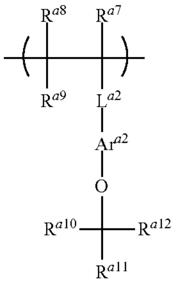

(A3)

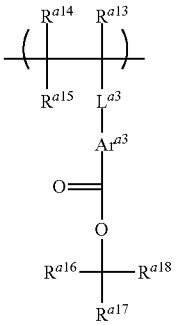

In General formula (A1), $R^{a1}$, $R^{a2}$, and $R^{a3}$ each independently represent a hydrogen atom, an alkyl group, a cycloalkyl group, a halogen atom, a cyano group, or an alkoxycarbonyl group, $L^{a1}$ represents a single bond or a divalent linking group, $Ar^{a1}$ represents an aromatic ring group, $R^{a4}$ represents a hydrogen atom, an alkyl group, a cycloalkyl group, an aryl group, an aralkyl group, or an alkenyl group, $R^{a5}$ and $R^{a6}$ each independently represent an alkyl group, a cycloalkyl group, an aryl group, an aralkyl group, or an alkenyl group, $R^{a4}$ and $R^{a5}$ may be linked together to form a ring, and $Ar^{a1}$ may be linked with $R^{a3}$ or $R^4$ to form a ring.

In General formula (A2), $R^{a7}$, $R^{a8}$, and $R^{a9}$ each independently represent a hydrogen atom, an alkyl group, a cycloalkyl group, a halogen atom, a cyano group, or an alkoxycarbonyl group, $L^{a2}$ represents a single bond or a divalent linking group, $Ar^{a2}$ represents an aromatic ring group, $R^{a10}$, $R^{a11}$, and $R^{a12}$ each independently represent an alkyl group, a cycloalkyl group, an aryl group, an aralkyl group, or an alkenyl group, and two of $R^{a10}$, $R^{a11}$, and $R^{a12}$ may be linked together to form a ring.

In General formula (A3), $R^{a13}$, $R^{a14}$, and $R^{a15}$ each independently represent a hydrogen atom, an alkyl group, a cycloalkyl group, a halogen atom, a cyano group, or an alkoxycarbonyl group, $L^{a3}$ represents a single bond or a divalent linking group, $Ar^3$ represents an aromatic ring group, $R^{a16}$, $R^{a17}$, and $R^{a18}$ each independently represent an alkyl group, a cycloalkyl group, an aryl group, an aralkyl group, or an alkenyl group, and two of $R^{a16}$, $R^{a17}$, and $R^{a18}$ may be linked together to form a ring.

[12]

The method for producing an actinic ray-sensitive or radiation-sensitive resin composition according to anyone of [1] to [11], wherein the resin (A) has a repeating unit having a group that generates acid in response to irradiation with an actinic ray or radiation.

[13]

A pattern forming method including a step of using an actinic ray-sensitive or radiation-sensitive resin composition produced by the method for producing an actinic ray-sensitive or radiation-sensitive resin composition according to any one of [1] to [11] to form, on a substrate, a resist film, a step of exposing the resist film, and a step of developing the exposed resist film using a developer.

[14]

A method for producing an electronic device, the method including the pattern forming method according to [13].

[15]

A method for producing an onium salt, the method including:

- a step (1) of passing a solution including an acid compound (CA) having a pKa of 2.0 or more, through a column packed with an ion-exchange resin; and
- a step (2) of using the acid compound (CA) having been passed through the column to produce an onium salt (C).

The present invention can provide a method for producing an actinic ray-sensitive or radiation-sensitive resin composition that includes an onium salt including an anion whose conjugate acid has a pKa of 2.0 or more and that has high post-etching LWR performance. The present invention can also provide a pattern forming method and a method for producing an electronic device that use the method for producing an actinic ray-sensitive or radiation-sensitive resin composition, and a method for producing the onium salt.

DESCRIPTION OF THE PREFERRED EMBODIMENTS

Hereinafter, the present invention will be described in detail.

Features may be described below with reference to representative embodiments according to the present invention; however, the present invention is not limited to the embodiments.

In this Specification, for written forms of groups (atomic groups), written forms without substituted or unsubstituted encompass, in addition to groups not having a substituent, groups including a substituent without departing from the spirit and scope of the present invention. For example, "alkyl group" encompasses not only alkyl groups not having a substituent (unsubstituted alkyl groups), but also alkyl groups having a substituent (substituted alkyl groups). In this Specification, "organic group" refers to a group including at least one carbon atom.

The substituent is preferably a monovalent substituent unless otherwise specified.

In this Specification, in the case of using a phrase "may have a substituent", the type of the substituent, the position of the substituent, and the number of such substituents are not particularly limited. The number of the substituents may be, for example, one, two, three, or more. Examples of the substituents include monovalent non-metallic atomic groups except for the hydrogen atom and, for example, can be selected from the following Substituent T.

Substituent T

Examples of Substituent T include halogen atoms such as a fluorine atom, a chlorine atom, a bromine atom, and an iodine atom; alkoxy groups such as a methoxy group, an ethoxy group, and a tert-butoxy group; aryloxy groups such as a phenoxy group and a p-tolyloxy group; alkoxycarbonyl groups such as a methoxycarbonyl group, a butoxycarbonyl group, and a phenoxycarbonyl group; acyloxy groups such as an acetoxy group, a propionyloxy group, and a benzoyloxy group; acyl groups such as an acetyl group, a benzoyl group, an isobutyryl group, an acryloyl group, a methacryloyl group, and a methoxalyl group; alkylsulfanyl groups such as a methylsulfanyl group and a tert-butylsulfanyl group; arylsulfanyl groups such as a phenylsulfanyl group and a p-tolylsulfanyl group; alkyl groups (for example, having 1 to 10 carbon atoms); cycloalkyl groups (for example, having 3 to 20 carbon atoms); aryl groups (for example, having 6 to 20 carbon atoms); heteroaryl groups; a hydroxy group; a carboxy group; a formyl group; a sulfo group; a cyano group; alkylaminocarbonyl groups; arylaminocarbonyl groups; a sulfonamide group; a silyl group; an amino group; monoalkylamino groups; dialkylamino groups; arylamino groups; a nitro group; a formyl group; and combinations of the foregoing.

In this Specification, "actinic ray" or "radiation" means, for example, the emission line spectrum of a mercury lamp, far-ultraviolet rays represented by excimer lasers, extreme ultraviolet rays (EUV light: Extreme Ultraviolet), X-rays, or an electron beam (EB: Electron Beam).

In this Specification, "light" means an actinic ray or a radiation.

In this Specification, "exposure" includes, unless otherwise specified, not only exposure using, for example, the emission line spectrum of a mercury lamp, far-ultraviolet rays represented by excimer lasers, extreme ultraviolet rays (EUV: Extreme ultraviolet), or X-rays, but also patterning using a corpuscular beam such as an electron beam or an ion beam.

In this Specification, "a value 'to' another value" is used to mean that it includes the value and the other value as the lower limit value and the upper limit value.

In this Specification, the bonding directions of divalent linking groups are not limited to the written forms unless otherwise specified. For example, in a compound represented by a formula "X—Y—Z" where Y is —COO—, Y may be —CO—O— or —O—CO—. The compound may be "X—CO—O—Z" or may be "X—O—CO—Z".

In this Specification, (meth)acrylate represents acrylate and methacrylate, and (meth)acrylic represents acrylic and methacrylic.

In this Specification, weight-average molecular weight (Mw), number-average molecular weight (Mn), and dispersity (hereafter, also referred to as "molecular weight distribution") (Mw/Mn) are defined as polystyrene equivalent values determined using a GPC (Gel Permeation Chromatography) apparatus (HLC-8120GPC manufactured by Tosoh Corporation) by GPC measurement (solvent: tetrahydrofuran, amount of flow (sample injection amount): 10 μL, column: TSK gel Multipore HXL-M manufactured by Tosoh Corporation, column temperature: 40° C., flow rate: 1.0 mL/min, detector: differential refractive index detector (Refractive Index Detector)).

In this Specification, the acid dissociation constant (pKa) represents pKa in an aqueous solution, specifically, a value determined using the following Software package 1, on the basis of the Hammett's substituent constant and the database of values in publicly known documents, by calculation.

Software Package 1: Advanced Chemistry Development (ACD/Labs) Software V8.14 for Solaris (1994-2007 ACD/Labs)

Alternatively, pKa can be determined by the molecular orbital method. Specifically, this method may be a method of, on the basis of a thermodynamic cycle, calculating $H^+$ dissociation free energy in an aqueous solution to achieve the determination. As the calculation method for H dissociation free energy, for example, DFT (density function method) can be performed for calculation; however, other various methods have been reported in documents etc. and the calculation method is not limited to DFT. Note that there are a plurality of pieces of software for performing DFT; for example, Gaussian 16 may be used.

In this Specification, as described above, pKa refers to a value determined using Software package 1, on the basis of the Hammett's substituent constant and the database of values in publicly known documents, by calculation; however, when use of this method cannot determine pKa, a value determined on the basis of DFT (density function method) using Gaussian 16 is employed.

In this Specification, as described above, pKa refers to "pKa in an aqueous solution"; however, when pKa in an aqueous solution cannot be determined, "pKa in a dimethyl sulfoxide (DMSO) solution" is employed.

"Solid content" means components forming the actinic ray-sensitive or radiation-sensitive film (typically, a resist film) and does not include solvents. As long as a component forms the actinic ray-sensitive or radiation-sensitive film, even when the component has the form of liquid, it is regarded as the solid content.

Hereinafter, the present invention will be described in detail.

Method for producing actinic ray-sensitive or radiation-sensitive resin composition A method for producing an actinic ray-sensitive or radiation-sensitive resin composition according to the present invention includes:

a step (1) of passing a solution including an acid compound (CA) having a pKa of 2.0 or more, through a column packed with an ion-exchange resin, a step (2) of using the acid compound (CA) having been passed through the column to produce an onium salt (C), and a step (3) of mixing together the onium salt (C) and a resin (A) that undergoes an increase in polarity due to action of acid.

In the present invention, the actinic ray-sensitive or radiation-sensitive resin composition is typically a resist composition and may be a positive resist composition or a negative resist composition. The resist composition may be a resist composition for alkali development or a resist composition for organic solvent development.

The resist composition may be a chemical amplification resist composition or a non-chemical amplification resist composition. The resist composition is typically a chemical amplification resist composition.

In the present invention, the actinic ray-sensitive or radiation-sensitive resin composition may also be referred to as "resist composition".

Step (1)

The step (1) is a step of passing a solution including an acid compound (CA) having a pKa of 2.0 or more, through a column packed with an ion-exchange resin.

Acid compound (CA) having pKa of 2.0 or more

The acid compound (CA) having a pKa of 2.0 or more (also referred to as "acid compound (CA)") will be described.

The pKa of the acid compound (CA) is 2.0 or more, preferably 2.5 or more, more preferably 3.0 or more. The pKa of the acid compound (CA) is preferably 8.0 or less, more preferably 6.0 or less, still more preferably 5.0 or less.

The pKa of the acid compound (CA) can be determined by the above-described method.

When the acid compound (CA) has two or more acid groups, two or more pKa values are determined; in this case, the smallest pKa value is 2.0 or more.

For example, the following compound CH-2 has two acid groups; the pKa of the dissociation reaction between CH-2 and CH-2a (the acid dissociation constant of the first stage, referred to as "pKa1") and the pKa of the dissociation reaction between CH-2a and CH-2b (the acid dissociation constant of the second stage, referred to as "pKa2") are determined and 2.0<pKa1<pKa2 is satisfied.

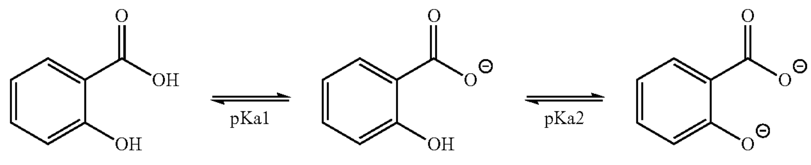

CH-2 CH-2a CH-2b

The acid compound (CA) preferably has a molecular weight of 50 to 500, more preferably 50 to 300, still more preferably 50 to 200.

The acid compound (CA) is preferably a carboxylic acid (compound having a carboxy group) or a phenol (compound having a phenolic hydroxy group).

The acid compound (CA) is preferably a compound represented by the following General formula (CA1).

(CA1)

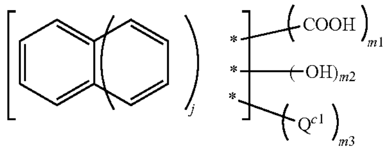

In General formula (CA1), j represents 0 or 1, $Q^{C1}$ represents a substituent, m1 and m2 each independently represent 0 or 1, m3 represents an integer of 0 or more and (6+2j−m1−m2) or less, a sum of m1 and m2 is 1 or 2, and

*'s each represent a direct bond connecting to the aromatic hydrocarbon described in General formula (CA1).

In General formula (CA1), when j represents 0, the aromatic hydrocarbon in General formula (CA1) represents benzene.

In General formula (CA1), when j represents 1, the aromatic hydrocarbon in General formula (CA1) represents naphthalene.

In General formula (CA1), $Q^{C1}$ represents a substituent. The substituent represented by $Q^{C1}$ is not particularly limited, but is preferably a halogen atom, an alkyl group, a cycloalkyl group, an alkenyl group, an aryl group, a heterocyclic group, a cyano group, or a nitro group.

When $Q^{C1}$ represents a halogen atom, the halogen atom is preferably a fluorine atom, a chlorine atom, a bromine atom, or an iodine atom, particularly preferably a fluorine atom.

When $Q^{C1}$ represents an alkyl group, the alkyl group may be linear or may be branched. The alkyl group is preferably an alkyl group having 1 to 10 carbon atoms such as a methyl group, an ethyl group, an n-propyl group, an isopropyl group, an n-butyl group, an isobutyl group, or a t-butyl group, more preferably an alkyl group having 1 to 6 carbon atoms.

The alkyl group may have a substituent; examples of the alkyl group having a substituent include fluorinated alkyl groups such as a trifluoromethyl group.

When $Q^{C1}$ represents a cycloalkyl group, the cycloalkyl group may be a monocyclic cycloalkyl group or may be a polycyclic cycloalkyl group. The number of carbon atoms of the cycloalkyl group is preferably 3 to 20, more preferably 4 to 15, still more preferably 5 to 10. The cycloalkyl group may have a substituent. A carbon atom included as an atom forming a ring of the cycloalkyl group may be substituted with an oxo group (═O). The cycloalkyl group is preferably a monocyclic cycloalkyl group such as a cyclopentyl group or a cyclohexyl group or a polycyclic cycloalkyl group such as a norbornyl group, a tetracyclodecanyl group, a tetracyclododecanyl group, or an adamantyl group.

When $Q^{C1}$ represents an aryl group, the aryl group may be a monocyclic aryl group or may be a polycyclic aryl group. The aryl group may have a substituent. The aryl group is preferably an aryl group having 6 to 20 carbon atoms, more preferably an aryl group having 6 to 10 carbon atoms; examples include a phenyl group, a naphthyl group, and an anthryl group.

When $Q^{C1}$ represents an alkenyl group, the alkenyl group may be linear or may be branched. The alkenyl group may have a substituent. The alkenyl group is preferably an alkenyl group having 2 to 10 carbon atoms such as a vinyl group, more preferably an alkenyl group having 2 to 6 carbon atoms.

When $Q^{C1}$ represents a heterocyclic group, the heterocyclic group is preferably an aromatic heterocyclic group or a non-aromatic heterocyclic group.

When $Q^{C1}$ represents an aromatic heterocyclic group (heteroaryl group), the aromatic heterocyclic group is preferably an aromatic heterocyclic group including at least one heteroatom selected from the group consisting of a nitrogen atom, a sulfur atom, and an oxygen atom.

The aromatic heterocyclic group may have a substituent.

A carbon atom included as an atom forming a ring of the aromatic heterocyclic group may be substituted with an oxo group (═O).

When $Q^{C1}$ represents a non-aromatic heterocyclic group (aliphatic heterocyclic group), the non-aromatic heterocyclic group is preferably a non-aromatic heterocyclic group including at least one heteroatom selected from the group consisting of a nitrogen atom, a sulfur atom, and an oxygen atom.

The non-aromatic heterocyclic group may have a substituent.

A carbon atom included as an atom forming a ring of the non-aromatic heterocyclic group may be substituted with an oxo group (═O).

When m1 represents 0 and m2 represents 1, m3 preferably represents an integer of 1 or more and at least one $Q^{C1}$ preferably represents a fluorine atom or a fluorinated alkyl group.

The acid compound (CA) is also preferably a compound represented by the following General formula (CA2).

(CA2)

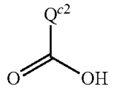

In General formula (CA2), $Q^{C2}$ represents an alkyl group or a cycloalkyl group.

When $Q^{C2}$ represents an alkyl group, the alkyl group may be linear or may be branched. The alkyl group is preferably an alkyl group having 1 to 10 carbon atoms such as a methyl group, an ethyl group, an n-propyl group, an isopropyl group, an n-butyl group, an isobutyl group, or a t-butyl group, more preferably an alkyl group having 1 to 6 carbon atoms.

The alkyl group may have a substituent; examples of the alkyl group having a substituent include fluorinated alkyl groups such as a trifluoromethyl group.

When $Q^{C2}$ represents a cycloalkyl group, the cycloalkyl group may be a monocyclic cycloalkyl group or may be a polycyclic cycloalkyl group. The number of carbon atoms of the cycloalkyl group is preferably 3 to 20, more preferably 4 to 15, still more preferably 5 to 10. The cycloalkyl group may have a substituent. A carbon atom included as an atom forming a ring of the cycloalkyl group may be substituted with an oxo group (═O). The cycloalkyl group is preferably a monocyclic cycloalkyl group such as a cyclopentyl group or a cyclohexyl group or a polycyclic cycloalkyl group such as a norbornyl group, a tetracyclodecanyl group, a tetracyclododecanyl group, or an adamantyl group.

The following are specific examples of the acid compound (CA); however, the present invention is not limited to these. Me represents a methyl group.

CH-1

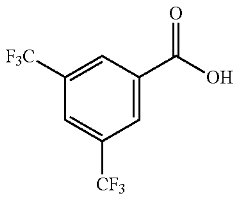

CH-2

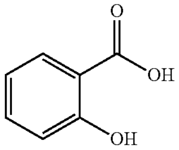

CH-3

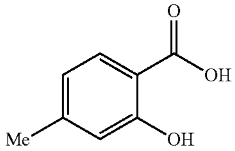

CH-4

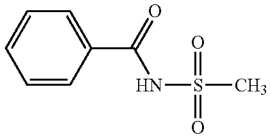

CH-5

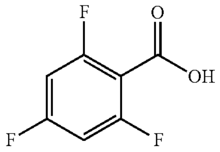

CH-6

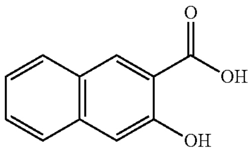

CH-7

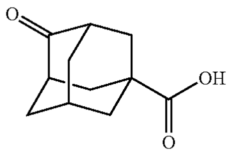

CH-8

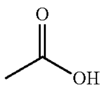

-continued

CH-9

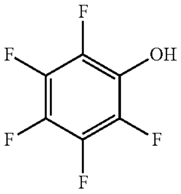

CH-10

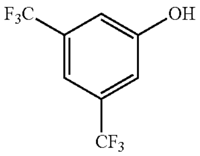

The acid compound (CA) can be synthesized by a method publicly known in the related art or can be a commercially available product.

Solvent

The solution including the acid compound (CA) and used in the step (1) can be obtained by mixing together the acid compound (CA) and a solvent.

The solvent is not particularly limited and may be an organic solvent or may be water.

Examples of the solvent include methylene chloride, chloroform, methanol, ethanol, acetonitrile, tetrahydrofuran, and water.

Ion-Exchange Resin

The ion-exchange resin used in the step (1) preferably has, as an ion-exchange group, a cation-exchange group. Examples of the cation-exchange group include a sulfonic group and a carboxylic group.

The ion-exchange resin preferably has, as an ion-exchange group, a strongly acidic cation-exchange group, more preferably has a sulfonic group.

The strongly acidic cation-exchange group is an ion-exchange group having a pKa of 1.0 or less.

A value (X1−X2) provided by subtracting, from the pKa (X1) of the acid compound (CA), the pKa (X2) of the ion-exchange group of the ion-exchange resin is preferably 1.0 or more, more preferably 2.0 or more, still more preferably 3.0 or more. X1−X2 is also preferably 8.0 or less, more preferably 7.0 or less, still more preferably 6.0 or less.

The pKa of the ion-exchange group of the ion-exchange resin is specifically the pKa of a monomer (M) having a structure corresponding to a repeating unit (T) to which the ion-exchange group bonds in the ion-exchange resin, the pKa being determined by the above-described method.

For example, when the repeating unit to which the ion-exchange group bonds is a repeating unit represented by Formula (T1) below, the pKa of a compound that is a monomer having a structure corresponding to the repeating unit represented by Formula (T1) and that is represented by Formula (M1) below is defined as the pKa of the ion-exchange group of the ion-exchange resin.

(T1)

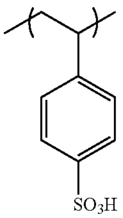

-continued (M1)

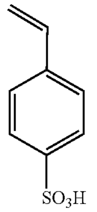

The ion-exchange resin preferably has a degree of cross-linking of 12% or less, more preferably 10% or less.

When the ion-exchange resin has a structure in which a copolymer of a main monomer (for example, styrene or (meth)acrylic acid) and a crosslinking agent (for example, divinylbenzene) serves as the base structure and, to this base structure, an ion-exchange group is bonded, the percent by mass of the crosslinking agent in the base structure is defined as the degree of crosslinking.

For example, in the ion-exchange resin, when a copolymer of styrene and divinylbenzene (crosslinking agent) serves as the base structure, the percent by mass of divinylbenzene in the base structure is defined as the degree of crosslinking.

As the ion-exchange resin, a commercially available product can be employed. Examples of the ion-exchange resin include products from Mitsubishi Chemical Corporation that are DIAION SK1BH, DIAION SK112L, Diaion WK10, DIAION SK104H, DIAION SK110, DIAION SK110L, DIAION SK112, DIAION SKIB, DIAION SK1BL, DIAION SK1BLH, DIAION SKL10, DIAION SKT10L, DIAION SKT110, DIAION SKT110L, DIAION SKT20L, DIAION PK208, DIAION PK208L, DIAION PK208LH, DIAION PK212L, DIAION PK212LH, DIAION PK216, DIAION PK216L, DIAION PK216H, DIAION PK216LH, DIAION PK218, DIAION PK218L, DIAION PK220, DIAION PK220L, DIAON PK228, DIAION PK228L, DIAION PK228LH, DIAION RCP145H, DIAION RCP160M, DIAION RCP200, DIAION RCP400, DIAION RCP610, DIAION UBK04, DIAION UBK08, DIAION UBK08H, DIAION UBK08HUP, DIAION UBK10, DIAION UBK10H, DIAION UBK10HUP, DIAION UBK12, DIAION UBK16, DIAION UBKN1U, DIAION UBKN1UMB, DIAION UBK522M, DIAION UBK530, DIAION UBK530J, DIAION UBK530K, DIAION UBK535, DIAION UBK535J, DIAION UBK535K, DIAION UBK535L, DIAION UBK550, DIAION UBK555, DIAION JC600, and DIAION JC603.

Column

The column used in the step (1) is not particularly limited as long as it can be packed with the ion-exchange resin. Examples include columns formed of glass.

In the step (1), during passing of the solution including the acid compound (CA) through the column packed with an ion-exchange resin, the temperature and the pressure are not particularly limited. For example, it can be performed at 5 to 40° C. and at atmospheric pressure.

Step (2)

The step (2) is a step of using the acid compound (CA) having been passed through the column in the above-described step (1) to produce an onium salt (C).

Onium Salt (C)

The onium salt (C) produced by the step (2) is an onium salt including an anion whose conjugate acid has a pKa of 2.0 or more.

The onium salt (C) is preferably a compound that generates the acid compound (CA) in response to irradiation with an actinic ray or radiation. The acid generated from a photoacid generator (B) described later preferably has a pKa lower than the pKa of the acid compound (CA).

In the actinic ray-sensitive or radiation-sensitive resin composition, the onium salt (C) preferably functions as an acid diffusion control agent.

When the actinic ray-sensitive or radiation-sensitive resin composition contains the photoacid generator (B) described later, the onium salt (C) can serve as a quencher that traps the acid generated from the photoacid generator (B) being exposed and that suppresses the reaction of, caused by an excess of generated acid, the acid-decomposable resin in the unexposed region. More specifically, when the onium salt (C) is an onium salt that generates an acid weaker than the acid generated from the photoacid generator (B), upon collision between the acid generated from the photoacid generator (B) in response to irradiation with an actinic ray or radiation and the onium salt (C) having an unreacted weak-acid anion, salt exchange is caused to release the weak acid to generate an onium salt having a strong-acid anion. In this process, the strong acid is exchanged with the weak acid having a lower catalytic activity, so that the acid is apparently deactivated to achieve control of acid diffusion.

The onium salt (C) is preferably a compound represented by "$M^+X^-$".

In the compound represented by "$M^+X^-$", $X^-$ is an anion formed by deprotonation of the acid compound (CA).

The anion ($X^-$) included in the onium salt (C) is preferably an anion represented by the following General formula (CA1a-1).

(CA1a-1)

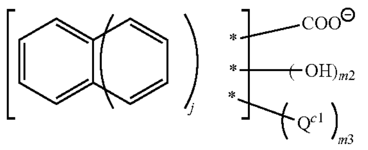

In General formula (CA1a-1), j represents 0 or 1, $Q^{C1}$ represents a substituent, m2 represents 0 or 1, m3 represents an integer of 0 or more and (5+2j−m2) or less, and

*'s each represent a direct bond connecting to the aromatic hydrocarbon in General formula (CA1a-1).

In General formula (CA1a-1), j and $Q^{C1}$ are the same as, in terms of descriptions, specific examples, and preferred examples, j and $Q^{C1}$ in General formula (CA1).

In General formula (CA1a-1), when m2 represents 1, the anion represented by General formula (CA1a-1) may be turned, by the second-stage dissociation reaction, into an anion represented by the following General formula (CA1a-1b).

(CA1a-1b)

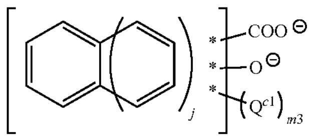

In General formula (CA1a-1b), j represents 0 or 1, $Q^{C1}$ represents a substituent, m3 represents an integer of 0 or more and (4+2j) or less, and

*'s each represent a direct bond connecting to the aromatic hydrocarbon in General formula (CA1a-ab).

In General formula (CA1a-1b), j and $Q^{C1}$ are the same as, in terms of descriptions, specific examples, and preferred examples, j and $Q^{C1}$ in General formula (CA1).

The anion ($X^-$) included in the onium salt (C) is also preferably an anion represented by the following General formula (CA1a-2).

(CA1a-2)

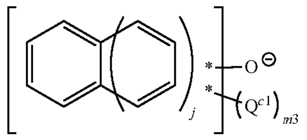

In General formula (CA1a-2), j represents 0 or 1, $Q^{C1}$ represents a substituent, m3 represents an integer of 0 or more and (5+2j−m2) or less, and

*'s each represent a direct bond connecting to the aromatic hydrocarbon in General formula (CA1a-1).

In General formula (CA1a-2), j and $Q^{C1}$ are respectively the same as, in terms of descriptions, specific examples, and preferred examples, j and $Q^{C1}$ in General formula (CA1).

In General formula (CA1a-2), m3 preferably represents an integer of 1 or more and at least one $Q^{C1}$ preferably represents a fluorine atom or a fluorinated alkyl group.

The anion ($X^-$) included in the onium salt (C) is also preferably an anion represented by the following General formula (CA2a).

(CA2a)

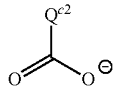

In General formula (CA2a), $Q^{C2}$ represents an alkyl group or a cycloalkyl group.

In General formula (CA2a), $Q^{C2}$ is the same as, in terms of descriptions, specific examples, and preferred examples, $Q^{C2}$ in General formula (CA2).

The following are specific examples of the anion ($X^-$) included in the onium salt (C); however, the present invention is not limited to these. Me represents a methyl group.

CH-1a

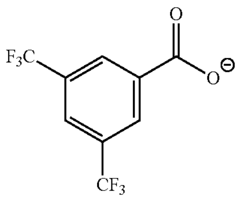

-continued

CH-2a

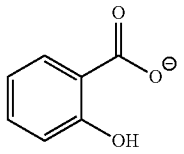

CH-3a

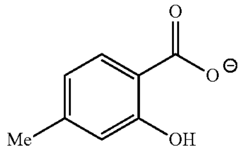

CH-4a

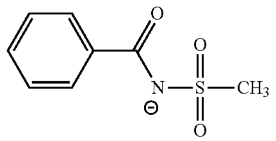

CH-5a

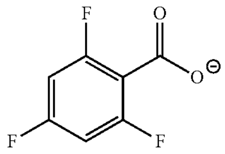

CH-6a

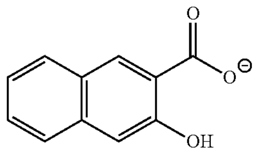

CH-7a

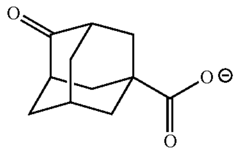

CH-8a

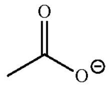

CH-9a

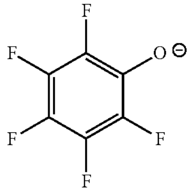

CH-10a

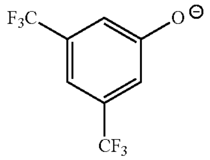

In the compound represented by "$M^+X^-$", $M^+$ represents an organic cation.

The organic cation is not particularly limited. For the valence, the organic cation may be mono-, di-, or higher valent.

In particular, the organic cation is preferably a cation represented by Formula (ZaI) (hereafter, also referred to as "Cation (ZaI)"), or a cation represented by Formula (ZaII) (hereafter, also referred to as "Cation (ZaII)").

(ZaI)

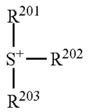

(ZaII)

$R^{204}$—$I^+$—$R^{205}$

In Formula (ZaI) above, $R^{201}$, $R^{212}$, and $R^{203}$ each independently represent an organic group.

In $R^{201}$, $R^{202}$, and $R^{203}$, such an organic group preferably has 1 to 30, more preferably 1 to 20 carbon atoms. Of $R^{201}$ to $R^{203}$, two may be linked together to form a ring structure and the ring may include an oxygen atom, a sulfur atom, an ester group, an amide group, or a carbonyl group. Examples of the group formed by linking together two of $R^{201}$ to $R^{203}$ include alkylene groups (such as a butylene group and a pentylene group), and $-CH_2-CH_2-O-CH_2-CH_2-$.

In Formula (ZaI), preferred examples of the organic cation include, as described later, Cation (ZaI-1), Cation (ZaI-2), Cation (ZaI-3b), and Cation (ZaI-4b).

First, Cation (ZaI-1) will be described.

Cation (ZaI-1) is an aryl sulfonium cation represented by Formula (ZaI) above where at least one of $R^{20'}$ to $R^{203}$ is an aryl group.

In the aryl sulfonium cation, all of $R^{201}$ to $R^{203}$ may be aryl groups, or at least one of $R^{201}$ to $R^{203}$ may be an aryl group and the other may be an alkyl group or a cycloalkyl group.

Alternatively, one of $R^{201}$ to $R^{203}$ may be an aryl group and the other two of $R^{201}$ to $R^{203}$ may be linked together to form a ring structure and the ring may include an oxygen atom, a sulfur atom, an ester group, an amide group, or a carbonyl group. Examples of the group formed by linking together two of $R^{201}$ to $R^{203}$ include alkylene groups in which at least one methylene group may be substituted with an oxygen atom, a sulfur atom, an ester group, an amide group, and/or a carbonyl group (such as a butylene group, a pentylene group, and $-CH_2-CH_2-O-CH_2-CH_2-$).

Examples of the aryl sulfonium cation include triaryl sulfonium cations, diaryl alkyl sulfonium cations, aryl dialkyl sulfonium cations, diaryl cycloalkyl sulfonium cations, and aryl dicycloalkyl sulfonium cations.

The aryl group included in the aryl sulfonium cation is preferably a phenyl group or a naphthyl group, more preferably a phenyl group. The aryl group may be an aryl group having a heterocyclic structure having an oxygen atom, a nitrogen atom, or a sulfur atom, for example. Examples of the heterocyclic structure include a pyrrole residue, a furan residue, a thiophene residue, an indole residue, a benzofuran residue, and a benzothiophene residue. When the aryl sulfonium cation has two or more aryl groups, the two or more aryl groups may be the same or different.

The aryl sulfonium cation optionally has an alkyl group or cycloalkyl group that is preferably a linear alkyl group having 1 to 15 carbon atoms, a branched alkyl group having 3 to 15 carbon atoms, or a cycloalkyl group having 3 to 15 carbon atoms, more preferably a methyl group, an ethyl group, a propyl group, an n-butyl group, a sec-butyl group, a t-butyl group, a cyclopropyl group, a cyclobutyl group, or a cyclohexyl group.

In $R^{201}$ to $R^{203}$, the aryl group, the alkyl group, and the cycloalkyl group may have a substituent; the substituent is preferably an alkyl group (having, for example, 1 to 15 carbon atoms), a cycloalkyl group (having, for example, 3 to 15 carbon atoms), an aryl group (having, for example, 6 to 14 carbon atoms), an alkoxy group (having, for example, 1 to 15 carbon atoms), a cycloalkylalkoxy group (having, for example, 1 to 15 carbon atoms), a halogen atom (for example, fluorine or iodine), a hydroxy group, a carboxyl group, an ester group, a sulfinyl group, a sulfonyl group, an alkylthio group, or a phenylthio group.

The substituent may further have, if possible, a substituent; the alkyl group also preferably has, as a substituent, a halogen atom to serve as an alkyl halide group such as a trifluoromethyl group.

Such substituents are also preferably combined appropriately to form an acid-decomposable group.

Note that the acid-decomposable group means a group that is decomposed by the action of acid to generate a polar group, and preferably has a structure in which a group that leaves by the action of acid protects the polar group. The polar group and the leaving group are the same as those in the resin (A) described later.

Hereinafter, Cation (ZaI-2) will be described.

Cation (ZaI-2) is a cation represented by Formula (ZaI) where $R^{201}$ to $R^{203}$ each independently represent an organic group not having an aromatic ring. The aromatic ring also encompasses aromatic rings including heteroatoms.

In $R^{201}$ to $R^{203}$, the organic group not having an aromatic ring preferably has 1 to 30, more preferably 1 to 20 carbon atoms.

$R^{201}$ to $R^{203}$ each independently represent preferably an alkyl group, a cycloalkyl group, an allyl group, or a vinyl group, more preferably a linear or branched 2-oxoalkyl group, a 2-oxocycloalkyl group, or an alkoxycarbonylmethyl group, still more preferably a linear or branched 2-oxoalkyl group.

In $R^{201}$ to $R^{203}$, the alkyl group and the cycloalkyl group may be, for example, a linear alkyl group having 1 to 10 carbon atoms or a branched alkyl group having 3 to 10 carbon atoms (for example, a methyl group, an ethyl group, a propyl group, a butyl group, or a pentyl group), and a cycloalkyl group having 3 to 10 carbon atoms (for example, a cyclopentyl group, a cyclohexyl group, or a norbornyl group).

$R^{201}$ to $R^{203}$ may be further substituted with a halogen atom, an alkoxy group (having, for example, 1 to 5 carbon atoms), a hydroxy group, a cyano group, or a nitro group.

In $R^{201}$ to $R^{203}$, such substituents are also preferably provided independently as appropriate combinations of substituents to form acid-decomposable groups.

Hereinafter, Cation (ZaI-3b) will be described.

Cation (ZaI-3b) is a cation represented by the following Formula (ZaI-3b).

(ZaI-3b)

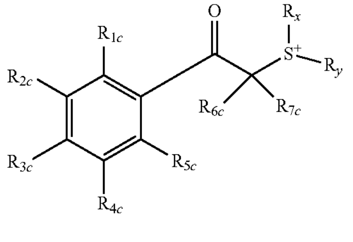

In Formula (ZaI-3b), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxy group, a nitro group, an alkylthio group, or an arylthio group.

$R_{6c}$ and $R_{7c}$ each independently represent a hydrogen atom, an alkyl group (for example, a t-butyl group), a cycloalkyl group, a halogen atom, a cyano group, or an aryl group.

$R_x$ and $R_y$ each independently represent an alkyl group, a cycloalkyl group, a 2-oxoalkyl group, a 2-oxocycloalkyl group, an alkoxycarbonylalkyl group, an allyl group, or a vinyl group.

In $R_{1c}$ to $R_{7c}$ and $R_x$ and $R_y$, such substituents are also preferably provided independently as appropriate combinations of substituents to form acid-decomposable groups.

Any two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$ may be individually linked together to form rings; these rings may each independently include an oxygen atom, a sulfur atom, a ketone group, an ester bond, or an amide bond.

Such a ring may be an aromatic or non-aromatic hydrocarbon ring, an aromatic or non-aromatic heterocycle, or a polycyclic fused ring formed as a combination of two or more of these rings. The ring may be a three- to ten-membered ring, and is preferably a four- to eight-membered ring, more preferably a five- or six-membered ring.

Examples of the groups formed by linking together any two or more of $R_{1c}$ to $R_{5c}$, $R_{6c}$ and $R_{7c}$, and $R_x$ and $R_y$ include alkylene groups such as a butylene group and a pentylene group. In such an alkylene group, a methylene group may be substituted with a heteroatom such as an oxygen atom.

The groups formed by linking together $R_{5c}$ and $R_{6c}$, and $R_{5c}$ and $R_x$ are preferably single bonds or alkylene groups. Examples of the alkylene groups include a methylene group and an ethylene group.

$R_{1c}$ to $R_{5c}$, $R_{6c}$, $R_{7c}$, $R_c$, $R_y$, and the rings formed by individually linking together any two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$ may have a substituent.

Hereinafter, Cation (ZaI-4b) will be described.

Cation (ZaI-4b) is a cation represented by the following Formula (ZaI-4b).

(ZaI-4b)

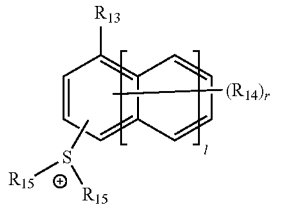

In Formula (ZaI-4b), l represents an integer of 0 to 2; and r represents an integer of 0 to 8.

$R_{13}$ represents a hydrogen atom, a halogen atom (for example, a fluorine atom or an iodine atom), a hydroxy group, an alkyl group, an alkyl halide group, an alkoxy group, a carboxyl group, an alkoxycarbonyl group, or a group including a cycloalkyl group (may be the cycloalkyl group itself or a group including, as a part thereof, the cycloalkyl group). These groups may have a substituent.

$R_{14}$ represents a hydroxy group, a halogen atom (for example, a fluorine atom or an iodine atom), an alkyl group, an alkyl halide group, an alkoxy group, an alkoxycarbonyl group, an alkylcarbonyl group, an alkylsulfonyl group, a cycloalkylsulfonyl group, or a group including a cycloalkyl group (may be the cycloalkyl group itself or a group including, as a part thereof, the cycloalkyl group). These groups may have a substituent. When there are a plurality of $R_{14}$'s, $R_{14}$'s each independently represent such a group, for example, a hydroxy group.

$R_{15}$'s each independently represent an alkyl group, a cycloalkyl group, or a naphthyl group. Two $R_{15}$'s may be linked together to form a ring. When two $R_{15}$'s are linked together to form a ring, the ring skeleton may include a heteroatom such as an oxygen atom or a nitrogen atom.

In an example, two $R_{15}$'s are preferably alkylene groups and linked together to form a ring structure. Note that the alkyl group, the cycloalkyl group, the naphthyl group, and the ring formed by linking together two $R_{15}$'s may have a substituent.

In Formula (ZaI-4b), in $R_{13}$, $R_{14}$, and $R_{15}$, the alkyl groups may be linear or branched. Such an alkyl group preferably has 1 to 10 carbon atoms. Preferred examples of the alkyl group include a methyl group, an ethyl group, an n-butyl group, and a t-butyl group.

In $R_{13}$ to $R_{15}$, and $R_x$ and $R_y$, such substituents are also preferably provided independently as appropriate combinations of substituents to form acid-decomposable groups.

Hereinafter, Formula (ZaII) will be described.

In Formula (ZaII), $R^{204}$ and $R^{205}$ each independently represent an aryl group, an alkyl group, or a cycloalkyl group.

In $R^{204}$ and $R^{205}$, the aryl group is preferably a phenyl group or a naphthyl group, more preferably a phenyl group. In $R^{204}$ and $R^{205}$, the aryl group may be an aryl group having a heterocycle having an oxygen atom, a nitrogen atom, or a sulfur atom, for example. Examples of the skeleton of the aryl group having a heterocycle include pyrrole, furan, thiophene, indole, benzofuran, and benzothiophene.

In $R^{204}$ and $R^{205}$, the alkyl group and the cycloalkyl group are preferably a linear alkyl group having 1 to 10 carbon atoms or a branched alkyl group having 3 to 10 carbon atoms (for example, a methyl group, an ethyl group, a propyl group, a butyl group, or a pentyl group), and a cycloalkyl group having 3 to 10 carbon atoms (for example, a cyclopentyl group, a cyclohexyl group, or a norbornyl group).

In $R^{204}$ and $R^{205}$, the aryl group, the alkyl group, and the cycloalkyl group may each independently have a substituent. In $R^{204}$ and $R^{205}$, the aryl group, the alkyl group, and the cycloalkyl group may have a substituent; examples of the substituent include alkyl groups (having, for example, 1 to 15 carbon atoms), cycloalkyl groups (having, for example, 3 to 15 carbon atoms), aryl groups (having, for example, 6 to 15 carbon atoms), alkoxy groups (having, for example, 1 to 15 carbon atoms), halogen atoms, a hydroxy group, and a phenylthio group. In $R^{204}$ and $R^{205}$, such substituents are also preferably provided independently as appropriate combinations of substituents to form acid-decomposable groups.

The following are specific examples of the organic cation; however, the present invention is not limited to these.

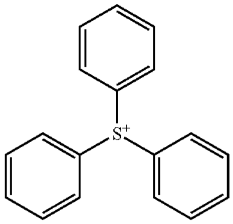
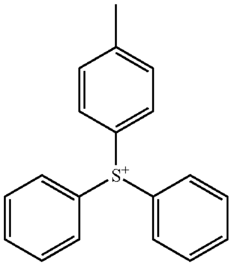
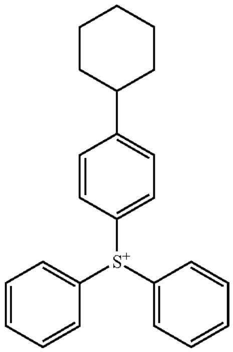
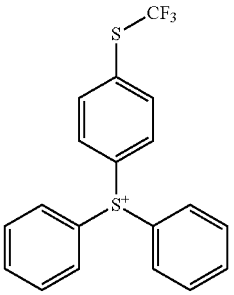
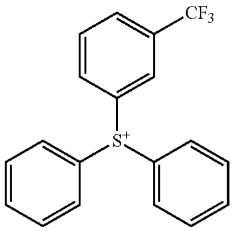
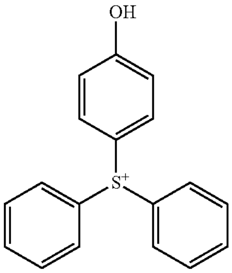
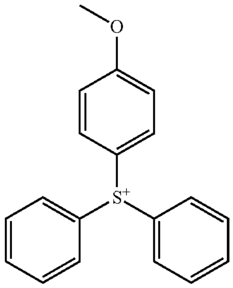
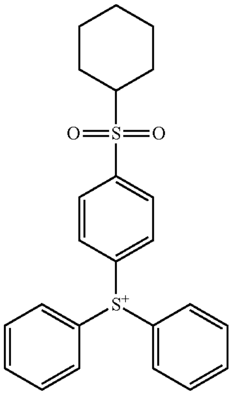
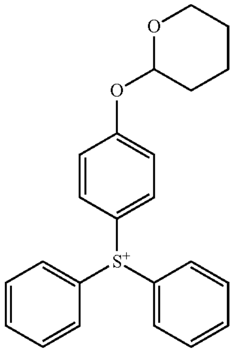
-continued
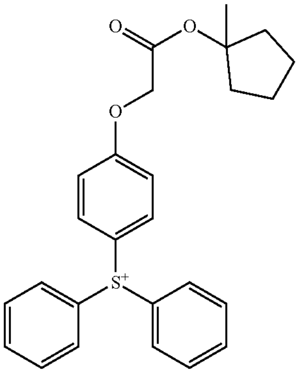
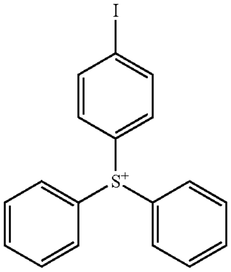
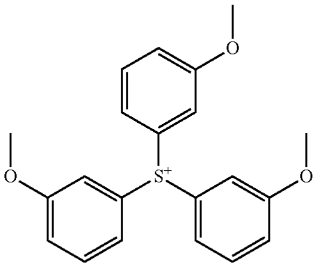
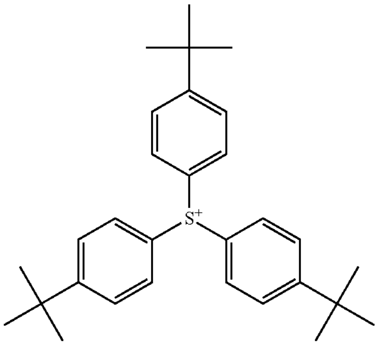
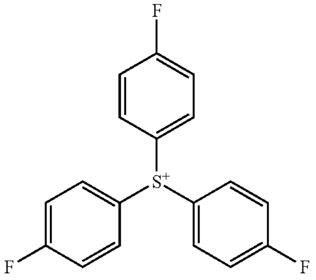

-continued
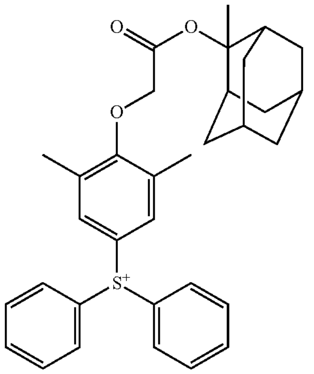
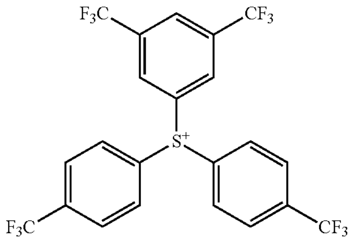
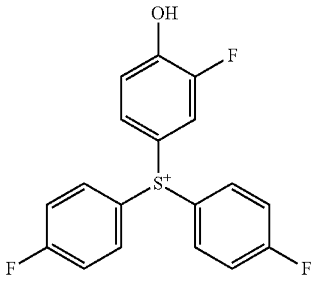
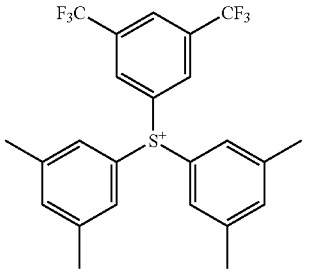
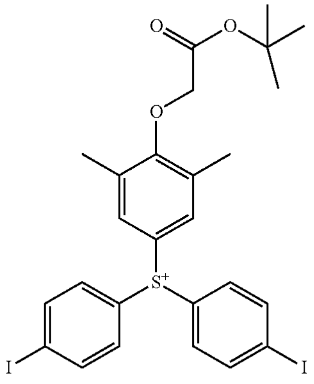
-continued
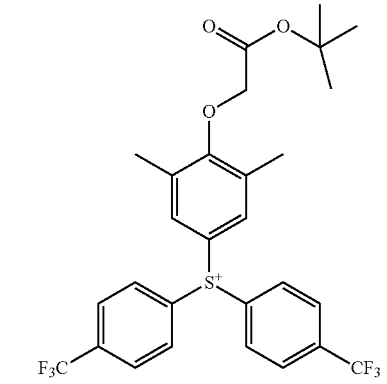
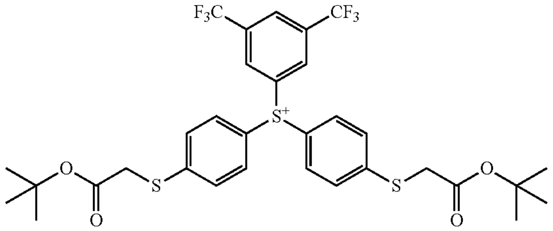
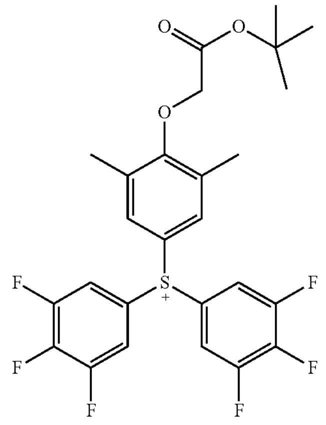
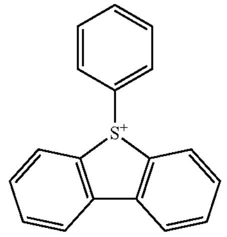
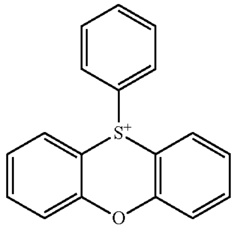
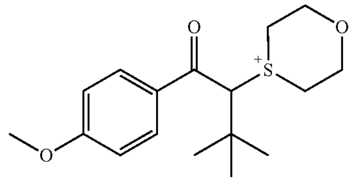
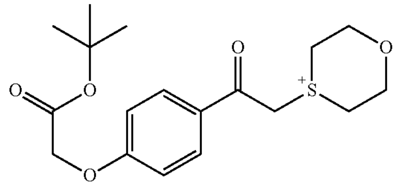

-continued

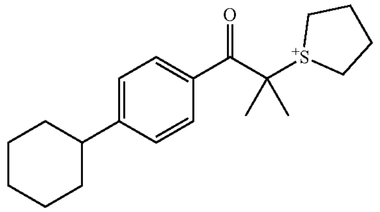

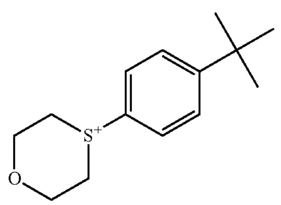

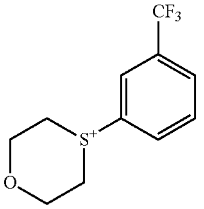

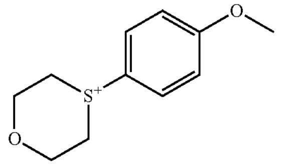

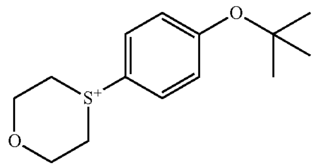

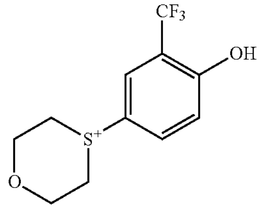

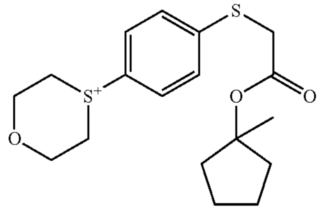

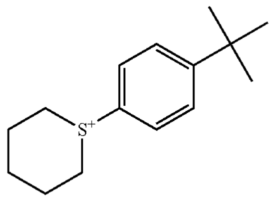

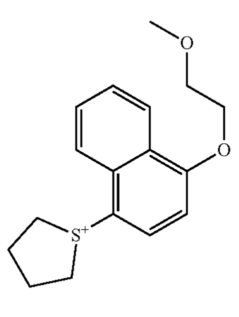

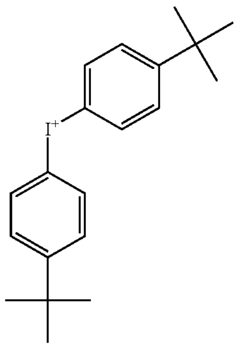

-continued

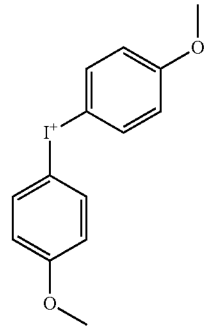

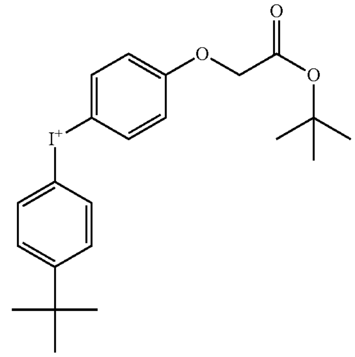

In the step (2), the method of using the acid compound (CA) to produce the onium salt (C) is not particularly limited.

For example, a salt constituted by an anion whose conjugate acid has a pKa larger than the pKa of the acid compound (CA) and a cation of the onium salt (C) serving as the target product can be caused to react with the acid compound (CA) in a solvent to exchange anions, to thereby produce the onium salt (C).

For example, when the onium salt (C) is a sulfonium salt including a carboxylate ion, as described by the following formula, a salt represented by General formula (c-a) (salt constituted by a sulfonium cation and a hydrogencarbonate ion) can be caused to react with a carboxylic acid serving as the acid compound (CA) and represented by General formula (c-b) in a solvent to thereby produce an onium salt serving as the onium salt (C) and represented by General formula (C1).

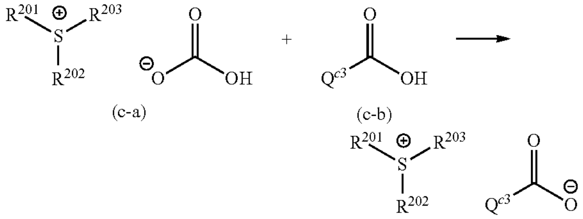

(c-a) (c-b) (C1)

In General formulas (c-a) and (C1), $R^{201}$, $R^{202}$, and $R^{203}$ respectively have the same meanings, specific examples, and preferred examples as in $R^{201}$, $R^{202}$, and $R^{203}$ in Formula (ZaI) above.

In General formulas (c-b) and (C1), $Q^{c3}$ represents an organic group.

The acid compound represented by General formula (c-b) may be a compound represented by General formula (CA1) above in which m1 is 1 or the compound represented by General formula (CA2).

The solvent for the reaction is not particularly limited and may be an organic solvent or water; examples include methylene chloride, chloroform, methanol, acetonitrile, and water.

The reaction is ordinarily performed in a temperature range of 15 to 80° C. for 0.5 to 24 hours, which is a non-limiting example.

Step (3)

The step (3) is a step of mixing together the onium salt (C) obtained in the above-described step (2) and a resin (A) that undergoes an increase in the polarity due to the action of acid.

In the actinic ray-sensitive or radiation-sensitive resin composition, the content of the onium salt (C) (in the case of a plurality of species, the total thereof) relative to the total solid content of the actinic ray-sensitive or radiation-sensitive resin composition is preferably 1 mass % or more, more preferably 5 mass % or more, still more preferably 10 mass % or more. The content of the onium salt (C) (in the case of a plurality of species, the total thereof) relative to the total solid content of the actinic ray-sensitive or radiation-sensitive resin composition is preferably 40 mass % or less, more preferably 35 mass % or less, still more preferably 30 mass % or less.

In the actinic ray-sensitive or radiation-sensitive resin composition, such onium salts (C) may be used alone or in combination of two or more thereof.

Resin (A) that Undergoes Increase in Polarity Due to Action of Acid

The resin (A) that undergoes an increase in the polarity due to the action of acid (also simply referred to as "resin (A)") will be described. The resin (A) is an acid-decomposable resin. The resin (A) preferably ordinarily includes a group that is decomposed by the action of acid to undergo an increase in the polarity (hereafter, also referred to as "acid-decomposable group") and includes a repeating unit having the acid-decomposable group. When the resin (A) has the acid-decomposable group, in a pattern forming method in this Specification, typically, in a case of employing a developer that is an alkali developer, a positive-type pattern is suitably formed or, in another case of employing a developer that is an organic-based developer, a negative-type pattern is suitably formed.

The repeating unit having an acid-decomposable group is preferably, in addition to a repeating unit having an acid-decomposable group described later, a repeating unit having an acid-decomposable group including an unsaturated bond.

Repeating Unit Having Acid-Decomposable Group

The acid-decomposable group refers to a group that is decomposed due to the action of acid to generate a polar group. The acid-decomposable group preferably has a structure in which the polar group is protected with a group (leaving group) that leaves due to the action of acid. Thus, the resin (A) has a repeating unit having a group that is decomposed due to the action of acid to generate a polar group. The resin having the repeating unit is subjected to the action of acid to have increased polarity to have an increased degree of solubility in the alkali developer, but have a decreased degree of solubility in organic solvents.

The polar group is preferably an alkali soluble group; examples include acidic groups such as a carboxyl group, a phenolic hydroxy group, fluorinated alcohol groups, a sulfonic group, a phosphate group, a sulfonamide group, a sulfonylimide group, (alkylsulfonyl)(alkylcarbonyl)methylene groups, (alkylsulfonyl)(alkylcarbonyl)imide groups, bis(alkylcarbonyl)methylene groups, bis(alkylcarbonyl)imide groups, bis(alkylsulfonyl)methylene groups, bis(alkylsulfonyl)imide groups, tris(alkylcarbonyl)methylene groups, and tris(alkylsulfonyl)methylene groups, and an alcoholic hydroxy group.

In particular, the polar group is preferably a carboxyl group, a phenolic hydroxy group, a fluorinated alcohol group (preferably a hexafluoroisopropanol group), or a sulfonic group.

Examples of the group that leaves due to the action of acid include groups represented by Formulas (Y1) to (Y4).

$$-C(Rx_1)(Rx_2)(Rx_3) \quad \text{Formula (Y1):}$$

$$-C(=O)OC(Rx_1)(Rx_2)(Rx_3) \quad \text{Formula (Y2):}$$

$$-C(R_{36})(R_{37})(OR_{38}) \quad \text{Formula (Y3):}$$

$$-C(Rn)(H)(Ar) \quad \text{Formula (Y4):}$$

In Formula (Y1) and Formula (Y2), $Rx_1$ to $Rx_3$ each independently represent an alkyl group (linear or branched), a cycloalkyl group (monocyclic or polycyclic), an alkenyl group (linear or branched), or an aryl group (monocyclic or polycyclic). Note that, when $Rx_1$ to $Rx_3$ are all alkyl groups (linear or branched), at least two of $Rx_1$ to $Rx_3$ are preferably methyl groups.

In particular, $Rx_1$ to $Rx_3$ preferably each independently represent a linear or branched alkyl group, and $Rx_1$ to $Rx_3$ more preferably each independently represent a linear alkyl group.

Two of $Rx_t$ to $Rx_3$ may be linked together to form a monocycle or a polycycle.

In $Rx_1$ to $Rx_3$, the alkyl group is preferably an alkyl group having 1 to 5 carbon atoms such as a methyl group, an ethyl group, an n-propyl group, an isopropyl group, an n-butyl group, an isobutyl group, or a t-butyl group.

In $Rx_1$ to $Rx_3$, the cycloalkyl group is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group.

In $Rx_1$ to $Rx_3$, the aryl group is preferably an aryl group having 6 to 10 carbon atoms, for example, a phenyl group, a naphthyl group, or an anthryl group.

In $Rx_1$ to $Rx_3$, the alkenyl group is preferably a vinyl group.

The ring formed by linking together two of $Rx_1$ to $Rx_3$ is preferably a cycloalkyl group. The cycloalkyl group formed by linking together two of $Rx_1$ to $Rx_3$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group, more preferably a monocyclic cycloalkyl group having 5 to 6 carbon atoms.

In the cycloalkyl group formed by linking together two of $Rx_1$ to $Rx_3$, one of methylene groups forming the ring may be replaced by a heteroatom such as an oxygen atom, a group including a heteroatom such as a carbonyl group, or a vinylidene group. In the cycloalkyl group, one or more ethylene groups forming the cycloalkane ring may be replaced by vinylene groups.

The group represented by Formula (Y1) or Formula (Y2) preferably has a form in which, for example, $Rx_1$ is a methyl group or an ethyl group, and $Rx_2$ and $Rx_3$ are linked together to form the cycloalkyl group.

When the actinic ray-sensitive or radiation-sensitive resin composition is, for example, an EUV-exposure resist composition, the alkyl groups, the cycloalkyl groups, the alkenyl groups, and the aryl groups represented by $Rx_1$ to $Rx_3$ and the ring formed by linking together two of $Rx_1$ to $Rx_3$ also preferably further have, as a substituent, a fluorine atom or an iodine atom.

In Formula (Y3), $R_{36}$ to $R_{38}$ each independently represent a hydrogen atom or a monovalent organic group. $R_{37}$ and $R_{38}$ may be linked together to form a ring. The monovalent organic group may be an alkyl group, a cycloalkyl group, an aryl group, an aralkyl group, or an alkenyl group. $R_{36}$ is also preferably a hydrogen atom.

Note that the alkyl group, the cycloalkyl group, the aryl group, and the aralkyl group may include a heteroatom such as an oxygen atom and/or a group including a heteroatom such as a carbonyl group. For example, in the alkyl group, the cycloalkyl group, the aryl group, and the aralkyl group, one or more methylene groups may be replaced by a heteroatom such as an oxygen atom and/or a group including a heteroatom such as a carbonyl group.

$R_{38}$ and another substituent of the main chain of the repeating unit may be linked together to form a ring. The group formed by linking together $R_{38}$ and another substituent of the main chain of the repeating unit is preferably an alkylene group such as a methylene group.

When the actinic ray-sensitive or radiation-sensitive resin composition is, for example, an EUV-exposure resist composition, the monovalent organic groups represented by $R_{36}$ to $R_{38}$ and the ring formed by linking together $R_{37}$ and $R_{38}$ also preferably further have, as a substituent, a fluorine atom or an iodine atom.

Formula (Y3) is preferably a group represented by the following Formula (Y3-1).

(Y3-1)

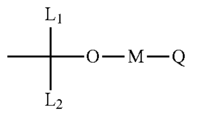

$L_1$ and $L_2$ each independently represent a hydrogen atom, an alkyl group, a cycloalkyl group, an aryl group, or a group of a combination of the foregoing (for example, a group of a combination of an alkyl group and an aryl group).

M represents a single bond or a divalent linking group.

Q represents an alkyl group that may include a heteroatom, a cycloalkyl group that may include a heteroatom, an aryl group that may include a heteroatom, an amino group, an ammonium group, a mercapto group, a cyano group, an aldehyde group, or a group of a combination of the foregoing (for example, a group of a combination of an alkyl group and a cycloalkyl group).

In the alkyl group and the cycloalkyl group, for example, one of methylene groups may be replaced by a heteroatom such as an oxygen atom or a group including a heteroatom such as a carbonyl group.

Note that one of $L_1$ and $L_2$ is preferably a hydrogen atom and the other is preferably an alkyl group, a cycloalkyl group, an aryl group, or a group that is a combination of an alkylene group and an aryl group.

At least two of Q, M, and $L_1$ may be linked together to form a ring (preferably a five-membered or six-membered ring).

From the viewpoint of forming finer patterns, $L_2$ is preferably a secondary or tertiary alkyl group, more preferably a tertiary alkyl group. Examples of the secondary alkyl group include an isopropyl group, a cyclohexyl group, and a norbornyl group; examples of the tertiary alkyl group include a tert-butyl group and an adamantane group. In such examples, Tg (glass transition temperature) and activation energy are increased, so that film hardness is ensured and fog can be suppressed.

When the actinic ray-sensitive or radiation-sensitive resin composition is, for example, an EUV-exposure resist composition, the alkyl groups, the cycloalkyl groups, the aryl groups, and the groups of combinations of the foregoing represented by $L_1$ and $L_2$ also preferably further have, as a substituent, a fluorine atom or an iodine atom. The alkyl groups, the cycloalkyl groups, the aryl groups, and the aralkyl groups also preferably include, in addition to a fluorine atom and an iodine atom, a heteroatom such as an oxygen atom. Specifically, in the alkyl groups, the cycloalkyl groups, the aryl groups, and the aralkyl groups, for example, one of methylene groups may be replaced by a heteroatom such as an oxygen atom or a group including a heteroatom such as a carbonyl group.

When the actinic ray-sensitive or radiation-sensitive resin composition is, for example, an EUV-exposure resist composition, in the alkyl group that may include a heteroatom, the cycloalkyl group that may include a heteroatom, the aryl group that may include a heteroatom, the amino group, the ammonium group, the mercapto group, the cyano group, the aldehyde group, and the group of a combination of the foregoing represented by Q, such a heteroatom is also preferably a heteroatom selected from the group consisting of a fluorine atom, an iodine atom, and an oxygen atom.

In Formula (Y4), Ar represents an aromatic ring group. Rn represents an alkyl group, a cycloalkyl group, or an aryl group. Rn and Ar may be linked together to form a non-aromatic ring. Ar is preferably an aryl group.

When the actinic ray-sensitive or radiation-sensitive resin composition is, for example, an EUV-exposure resist composition, the aromatic ring group represented by Ar and the alkyl group, the cycloalkyl group, and the aryl group represented by Rn also preferably have, as a substituent, a fluorine atom or an iodine atom.

From the viewpoint of providing a repeating unit having high acid decomposability, in the leaving group protecting the polar group, when a non-aromatic ring is directly bonded to the polar group (or its residue), in the non-aromatic ring, a ring-member atom adjacent to a ring-member atom directly bonded to the polar group (or its residue) also preferably does not have, as a substituent, a halogen atom such as a fluorine atom.

Alternatively, the group that leaves due to the action of acid may be a 2-cyclopentenyl group having a substituent (such as an alkyl group) such as 3-methyl-2-cyclopentenyl group, or a cyclohexyl group having a substituent (such as an alkyl group) such as a 1,1,4,4-tetramethylcyclohexyl group.

The repeating unit having an acid-decomposable group is also preferably a repeating unit represented by Formula (A).

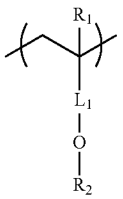

(A)

$L_1$ represents a divalent linking group that may have a fluorine atom or an iodine atom; $R_1$ represents a hydrogen atom, a fluorine atom, an iodine atom, or an alkyl group that may have a fluorine atom or an iodine atom, or an aryl group that may have a fluorine atom or an iodine atom; $R_2$ represents a leaving group that leaves due to the action of acid and that may have a fluorine atom or an iodine atom. Note that at least one of $L_1$, $R_1$, or $R_2$ has a fluorine atom or an iodine atom.

Examples of the divalent linking group that is represented by $L_1$ and may have a fluorine atom or an iodine atom include —CO—, —O—, —S—, —SO—, —$SO_2$—, hydrocarbon groups that may have a fluorine atom or an iodine atom (for example, alkylene groups, cycloalkylene groups, alkenylene groups, and arylene groups), and linking groups provided by linking together a plurality of the foregoing. In particular, $L_1$ is preferably —CO—, an arylene group, or an -arylene group-alkylene group having a fluorine atom or an iodine atom-, more preferably —CO— or an -arylene group-alkylene group having a fluorine atom or an iodine atom-.

The arylene group is preferably a phenylene group.

The alkylene group may be linear or branched. The number of carbon atoms of the alkylene group is not particularly limited, but is preferably 1 to 10, more preferably 1 to 3.

In the alkylene group having a fluorine atom or an iodine atom, the total number of fluorine atoms and iodine atoms is not particularly limited, but is preferably 2 or more, more preferably 2 to 10, still more preferably 3 to 6.

The alkyl group represented by $R_1$ may be linear or branched. The number of carbon atoms of the alkyl group is not particularly limited, but is preferably 1 to 10, more preferably 1 to 3.

In the alkyl group represented by $R_t$ and having a fluorine atom or an iodine atom, the total number of fluorine atoms and iodine atoms is not particularly limited, but is preferably 1 or more, more preferably 1 to 5, still more preferably 1 to 3.

The alkyl group represented by $R_t$ may include a heteroatom other than halogen atoms, such as an oxygen atom.

Examples of the leaving group that is represented by $R_2$ and may have a fluorine atom or an iodine atom include leaving groups that are represented by Formulas (Y1) to (Y4) above and that have a fluorine atom or an iodine atom.

The repeating unit having an acid-decomposable group is also preferably a repeating unit represented by Formula (AI).

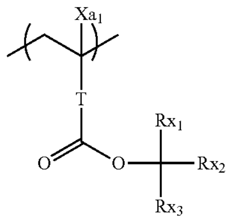

(AI)

In Formula (A1), $Xa_1$ represents a hydrogen atom or an alkyl group that may have a substituent. T represents a single bond or a divalent linking group. $Rx_1$ to $Rx_3$ each independently represent an alkyl group (linear or branched), a cycloalkyl group (monocyclic or polycyclic), an alkenyl group (linear or branched), or an aryl (monocyclic or polycyclic) group. Note that, when $Rx_1$ to $Rx_3$ are all alkyl groups (linear or branched), at least two of $Rx_1$ to $Rx_3$ are preferably methyl groups.

Two of $Rx_1$ to $Rx_3$ may be linked together to form a monocycle or polycycle (such as a monocyclic or polycyclic cycloalkyl group).

In $Xa_1$, the alkyl group that may have a substituent may be, for example, a methyl group or a group represented by —$CH_2$—$R_{11}$. $R_{11}$ represents a halogen atom (such as a fluorine atom), a hydroxy group, or a monovalent organic group. The monovalent organic group represented by $R_{11}$ is, for example, an alkyl group that has 5 or less carbon atoms and that may be substituted with a halogen atom, an acyl group that has 5 or less carbon atoms and that may be substituted with a halogen atom, or an alkoxy group that has 5 or less carbon atoms and that may be substituted with a halogen atom, and is preferably an alkyl group having 3 or less carbon atoms, more preferably a methyl group. $Xa_1$ is preferably a hydrogen atom, a methyl group, a trifluoromethyl group, or a hydroxymethyl group.

In T, the divalent linking group may be an alkylene group, an aromatic ring group, a —COO-Rt- group, or an —O-Rt- group. In the formulas, Rt represent an alkylene group or a cycloalkylene group.

T is preferably a single bond or a —COO-Rt- group. When T represents a —COO-Rt- group, Rt is preferably an alkylene group having 1 to 5 carbon atoms, more preferably a —$CH_2$— group, a —$(CH_2)_2$— group, or a —$(CH_2)_3$— group.

In $Rx_1$ to $Rx_3$, the alkyl group is preferably an alkyl group having 1 to 4 carbon atoms such as a methyl group, an ethyl group, an n-propyl group, an isopropyl group, an n-butyl group, an isobutyl group, or a t-butyl group.

In $Rx_1$ to $Rx_3$, the cycloalkyl group is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group.

In $Rx_1$ to $Rx_3$, the aryl group is preferably an aryl group having 6 to 10 carbon atoms, for example, a phenyl group, a naphthyl group, or an anthryl group.

In $Rx_1$ to $Rx_3$, the alkenyl group is preferably a vinyl group.

The cycloalkyl group formed by linking together two of $Rx_1$ to $Rx_3$ is preferably a monocyclic cycloalkyl group such as a cyclopentyl group or a cyclohexyl group, or also preferably a polycyclic cycloalkyl group such as a norbornyl group, a tetracyclodecanyl group, a tetracyclododecanyl group, or an adamantyl group. In particular, preferred is a monocyclic cycloalkyl group having 5 to 6 carbon atoms.

In the cycloalkyl group formed by linking together two of $Rx_1$ to $Rx_3$, for example, one of methylene groups forming the ring may be replaced by a heteroatom such as an oxygen atom, a group including a heteroatom such as a carbonyl group, or a vinylidene group. In the cycloalkyl group, one or more of the ethylene groups forming the cycloalkane ring may be replaced by vinylene groups.

The repeating unit represented by Formula (AI) preferably has a form in which, for example, $Rx_1$ is a methyl group or an ethyl group, and $Rx_2$ and $Rx_3$ are linked together to form the cycloalkyl group.

When the above-described groups each have a substituent, examples of the substituent include alkyl groups (having 1 to 4 carbon atoms), halogen atoms, a hydroxy group, alkoxy groups (having 1 to 4 carbon atoms), a carboxyl group, and alkoxycarbonyl groups (having 2 to 6 carbon atoms). The substituent preferably has 8 or less carbon atoms.

The repeating unit represented by Formula (AI) is preferably an acid-decomposable (meth)acrylic acid tertiary alkyl ester-based repeating unit (repeating unit where $Xa_1$ represents a hydrogen atom or a methyl group and T represents a single bond).

The following are non-limiting specific examples of the repeating unit having an acid-decomposable group. Note that, in the formulas, $Xa_1$ represent H, $CH_3$, $CF_3$, or $CH_2OH$, and Rxa and Rxb each independently represent a linear or branched alkyl group having 1 to 5 carbon atoms.

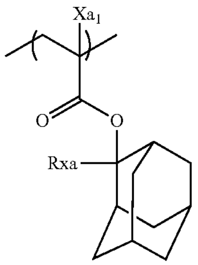
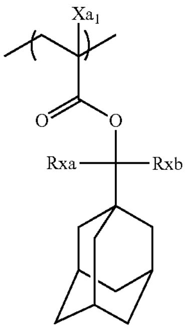
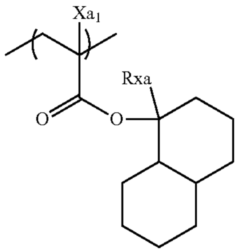
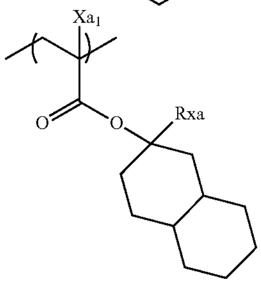
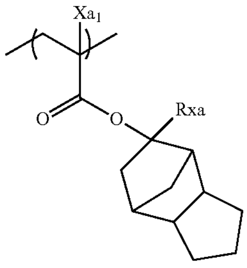

-continued

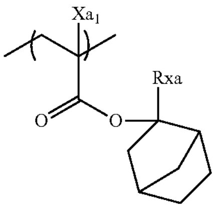
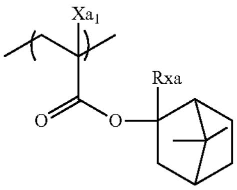
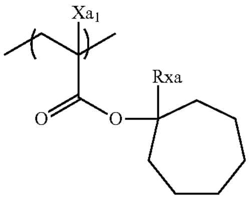
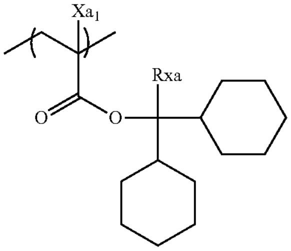
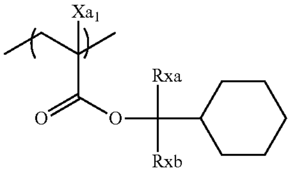
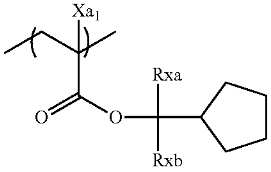
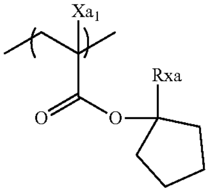
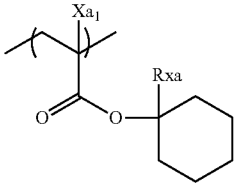
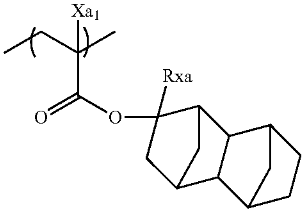
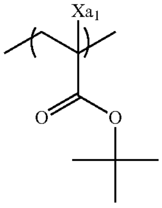
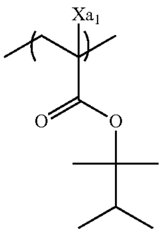
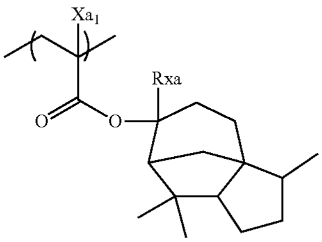

-continued
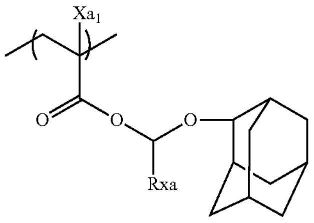
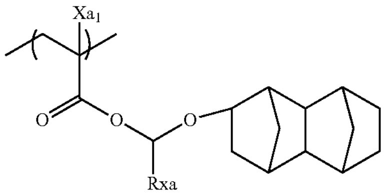
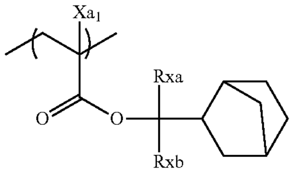
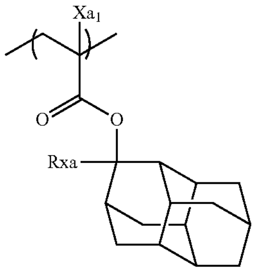
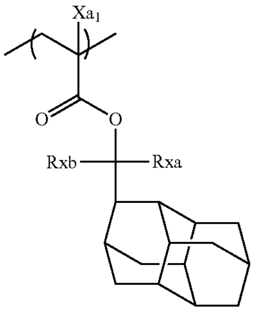
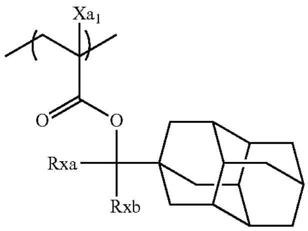
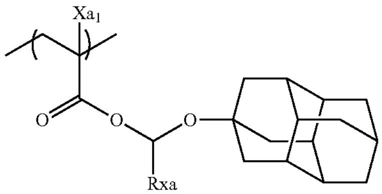
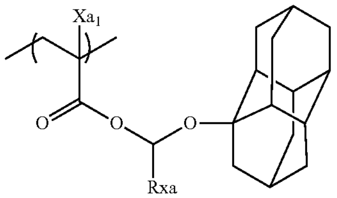
-continued
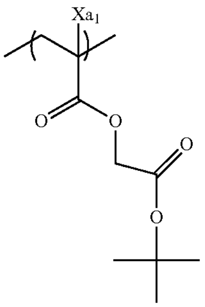
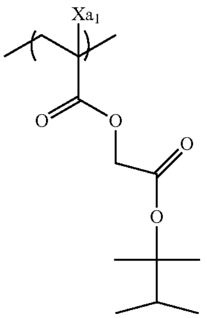
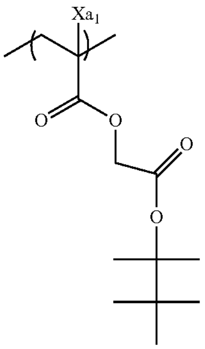
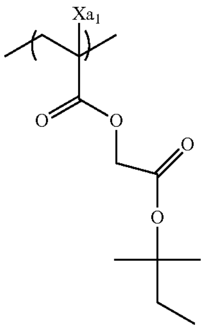
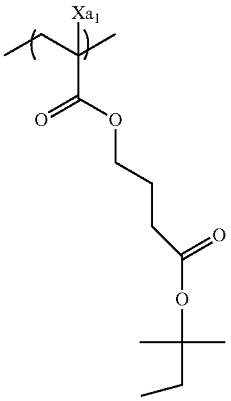
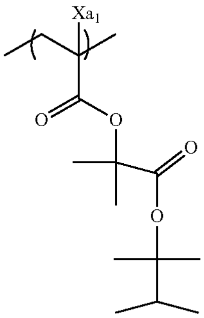
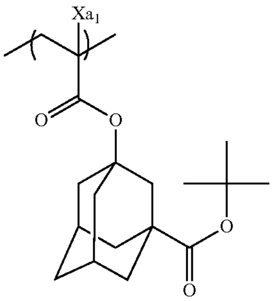
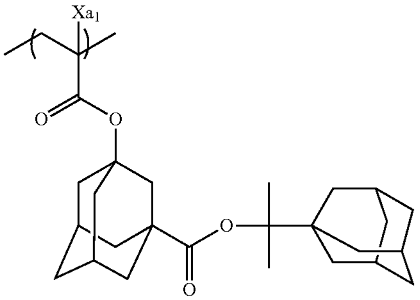

-continued
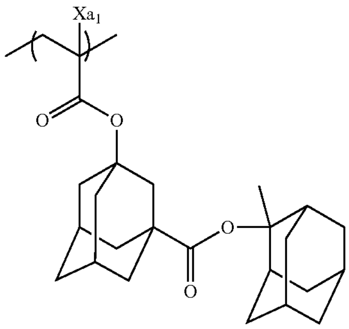
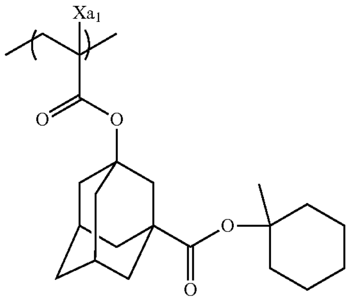
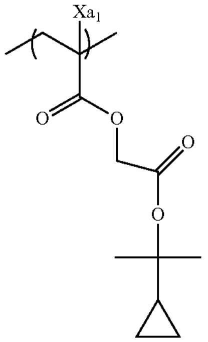
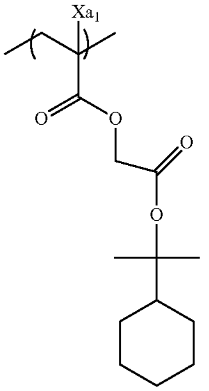
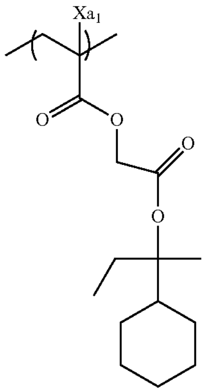
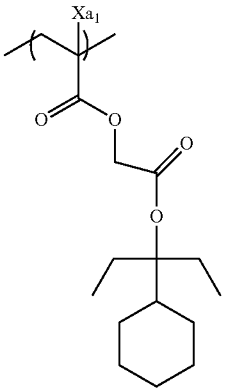
-continued
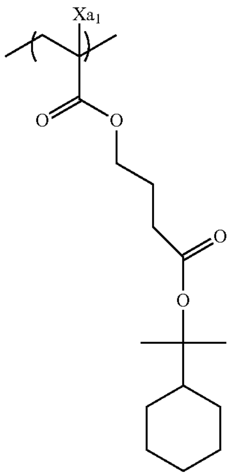
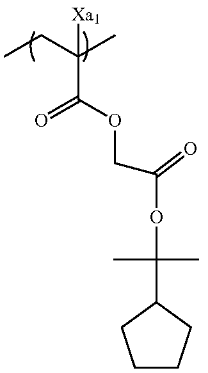
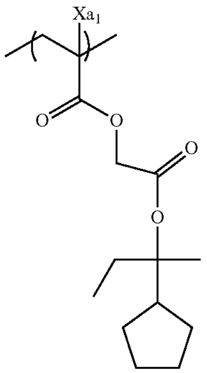
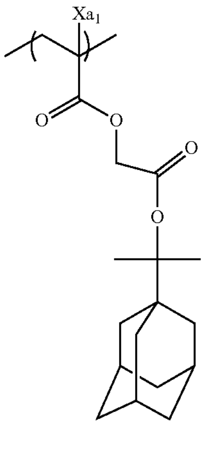
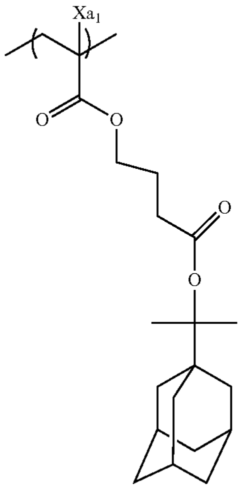
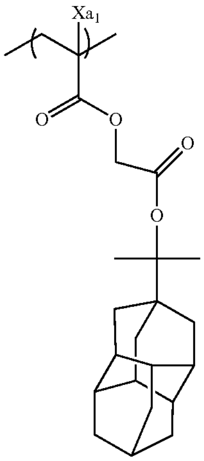

-continued
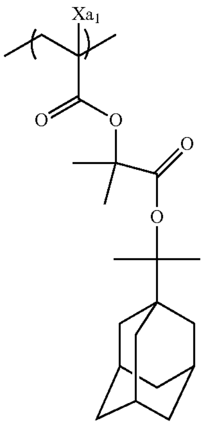
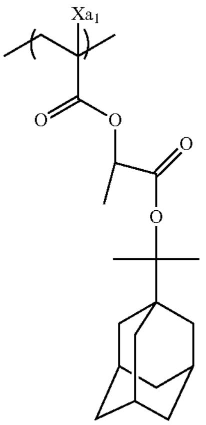
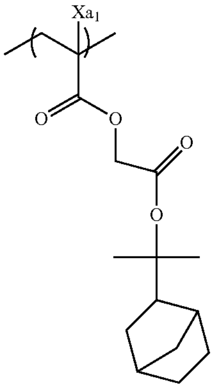
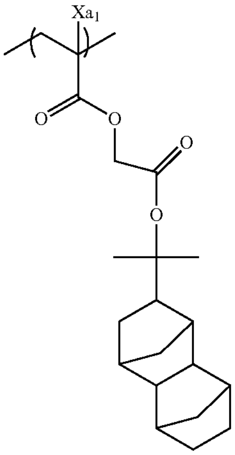
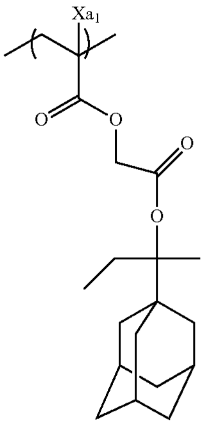
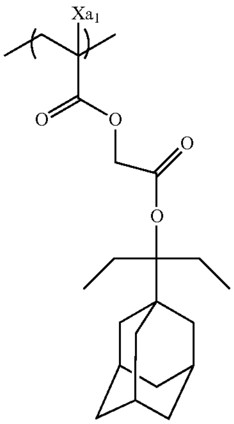
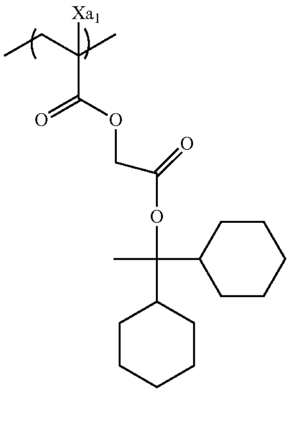
-continued
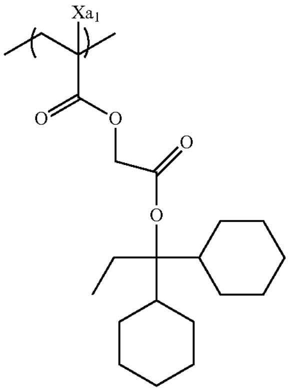
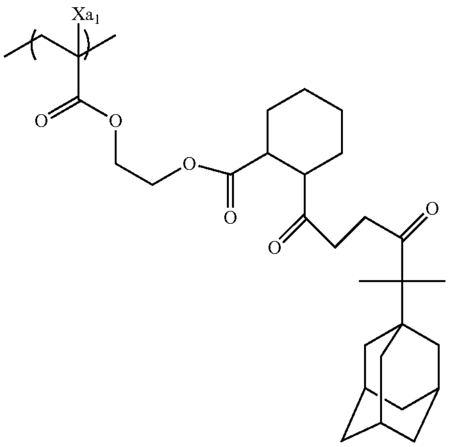
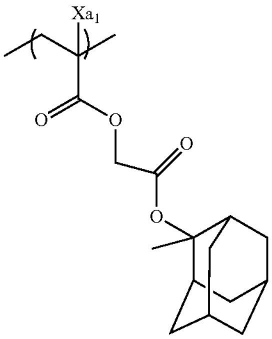
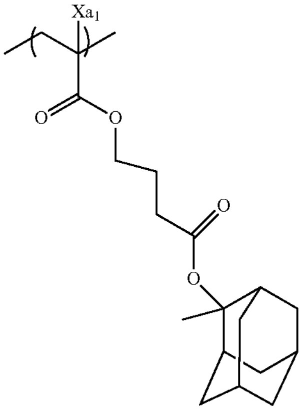

-continued
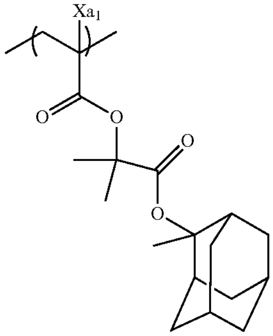
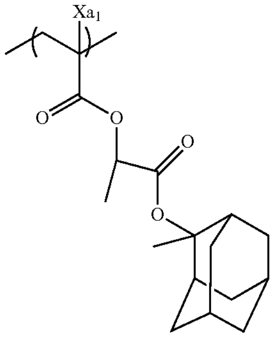
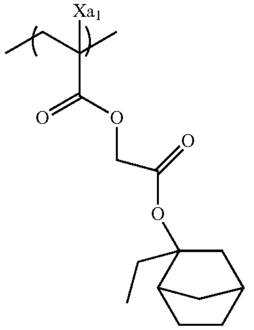
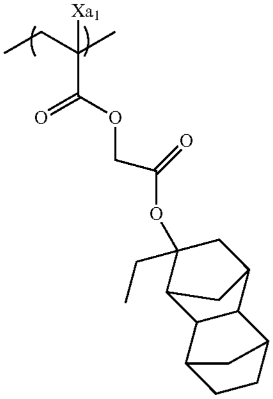
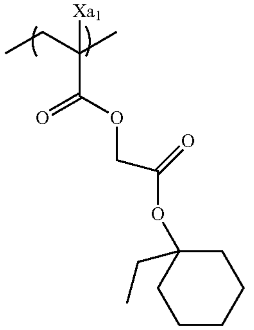
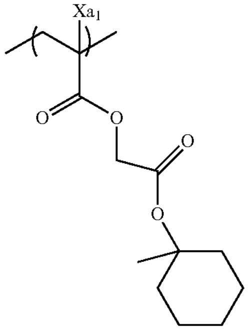
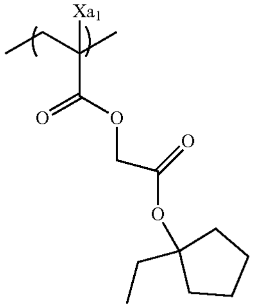
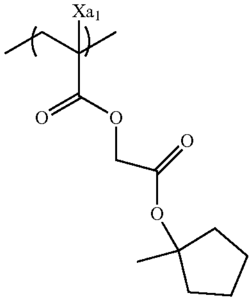
-continued
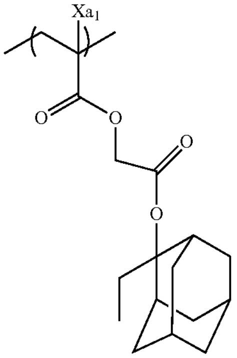
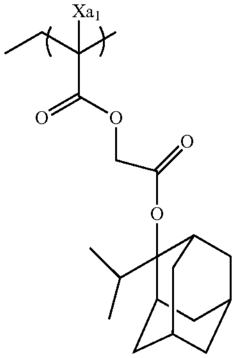
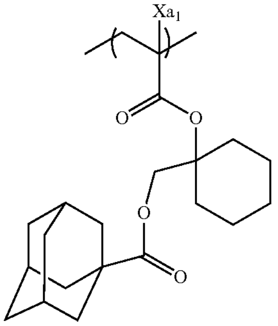
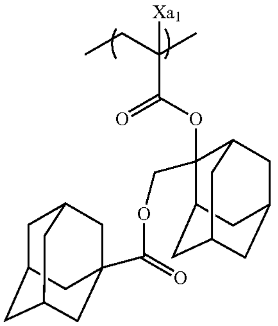
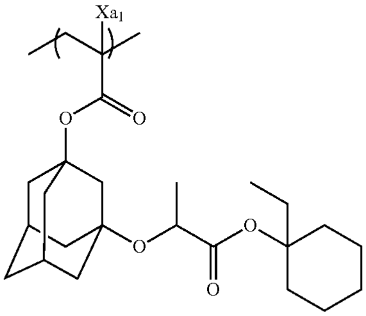
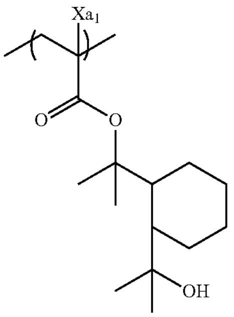
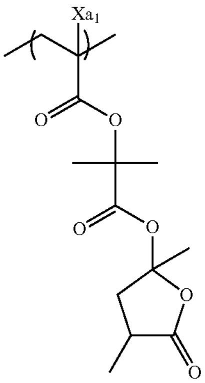

-continued

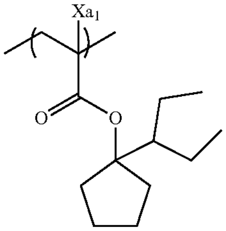

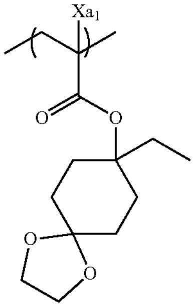

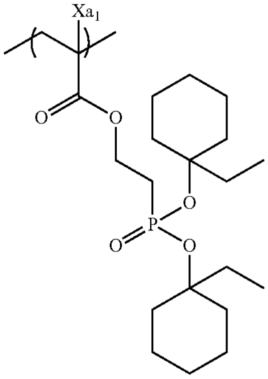

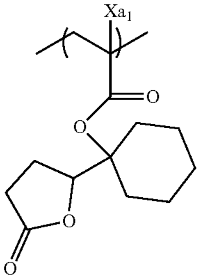

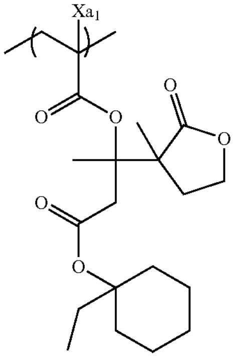

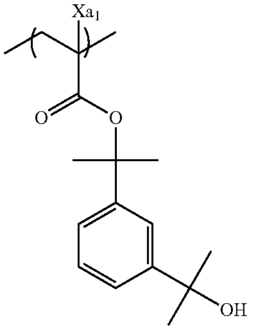

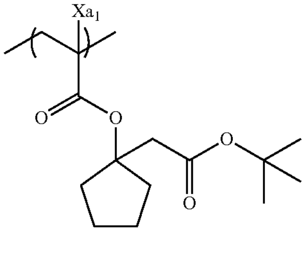

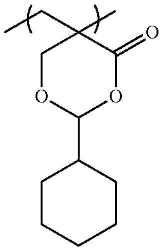

-continued

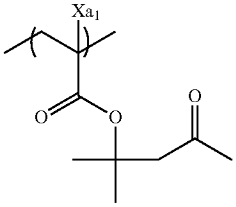

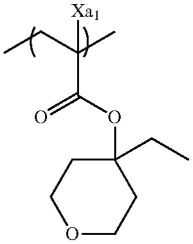

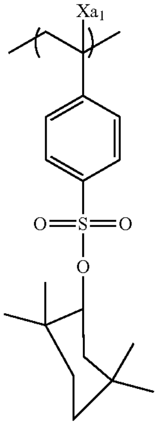

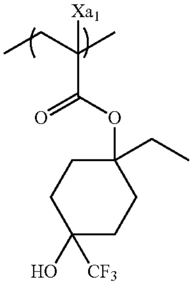

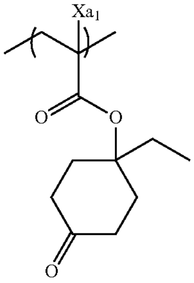

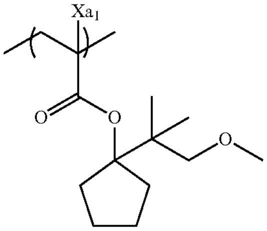

The resin (A) may have, as a repeating unit having an acid-decomposable group, a repeating unit having an acid-decomposable group including an unsaturated bond.

The repeating unit having an acid-decomposable group including an unsaturated bond is preferably a repeating unit represented by Formula (B).

(B)

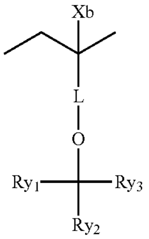

In Formula (B), Xb represents a hydrogen atom, a halogen atom, or an alkyl group that may have a substituent. L represents a single bond or a divalent linking group that may have a substituent. $Ry_1$ to $Ry_3$ each independently represent a linear or branched alkyl group, a monocyclic or polycyclic cycloalkyl group, an alkenyl group, an alkynyl group, or a monocyclic or polycyclic aryl group. Note that at least one of $Ry_1$ to $Ry_3$ represents an alkenyl group, an alkynyl group, a monocyclic or polycyclic cycloalkenyl group, or a monocyclic or polycyclic aryl group.

Two of $Ry_1$ to $Ry_3$ may be linked together to form a monocycle or polycycle (such as a monocyclic or polycyclic cycloalkyl group or cycloalkenyl group).

In Xb, the alkyl group that may have a substituent may be, for example, a methyl group or a group represented by —$CH_2$—Ru. Ru represents a halogen atom (such as a fluorine atom), a hydroxy group, or a monovalent organic group such as an alkyl group that has 5 or less carbon atoms and that may be substituted with a halogen atom, an acyl group that has 5 or less carbon atoms and that may be substituted with a halogen atom, or an alkoxy group that has 5 or less carbon atoms and that may be substituted with a halogen atom, and is preferably an alkyl group having 3 or less carbon atoms, more preferably a methyl group. Xb is preferably a hydrogen atom, a fluorine atom, a methyl group, a trifluoromethyl group, or a hydroxymethyl group.

In L, the divalent linking group may be an -Rt- group, a —CO— group, a —COO-Rt- group, a —COO-Rt-CO— group, an -Rt-CO— group, or an —O-Rt- group. In the formulas, Rt represent an alkylene group, a cycloalkylene group, or an aromatic ring group, and is preferably an aromatic ring group.

L is preferably an -Rt- group, a —CO— group, a —COO-Rt-CO— group, or an -Rt-CO— group. Rt may have a substituent such as a halogen atom, a hydroxy group, or an alkoxy group.

In $Ry_1$ to $Ry_3$, the alkyl group is preferably an alkyl group having 1 to 4 carbon atoms such as a methyl group, an ethyl group, an n-propyl group, an isopropyl group, an n-butyl group, an isobutyl group, or a t-butyl group.

In $Ry_1$ to $Ry_3$, the cycloalkyl group is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group.

In $Ry_1$ to $Ry_3$, the aryl group is preferably an aryl group having 6 to 10 carbon atoms, and may be, for example, a phenyl group, a naphthyl group, or an anthryl group.

In $Ry_1$ to $Ry_3$, the alkenyl group is preferably a vinyl group.

In $Ry_1$ to $Ry_3$, the alkynyl group is preferably an ethynyl group.

In $Ry_1$ to $Ry_3$, the cycloalkenyl group is preferably a structure in which a monocyclic cycloalkyl group such as a cyclopentyl group or a cyclohexyl group includes partially a double bond.

The cycloalkyl group formed by linking together two of $Ry_1$ to $Ry_3$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group. In particular, more preferred is a monocyclic cycloalkyl group having 5 to 6 carbon atoms.

In the cycloalkyl group or the cycloalkenyl group formed by linking together two of $Ry_1$ to $Ry_3$, for example, one of methylene groups forming the ring may be replaced by a heteroatom such as an oxygen atom, a group including a heteroatom such as a carbonyl group, a —$SO_2$— group, or a —$SO_3$— group, a vinylidene group, or a combination of the foregoing. In the cycloalkyl group or the cycloalkenyl group, one or more ethylene groups forming the cycloalkane ring or the cycloalkene ring may be replaced by vinylene groups.

The repeating unit represented by Formula (B) preferably has a form in which, for example, $Ry_1$ is a methyl group, an ethyl group, a vinyl group, an allyl group, or an aryl group, and $Ry_2$ and $Ry_3$ are linked together to form the above-described cycloalkyl group or cycloalkenyl group.

When the above-described groups each have a substituent, examples of the substituent include alkyl groups (having 1 to 4 carbon atoms), halogen atoms, a hydroxy group, alkoxy groups (having 1 to 4 carbon atoms), a carboxyl group, and alkoxycarbonyl groups (having 2 to 6 carbon atoms). The substituent preferably has 8 or less carbon atoms.

The repeating unit represented by Formula (B) is preferably an acid-decomposable (meth)acrylic acid tertiary ester-based repeating unit (a repeating unit in which Xb represents a hydrogen atom or a methyl group, and L represents a —CO— group), an acid-decomposable hydroxystyrene tertiary alkyl ether-based repeating unit (a repeating unit in which Xb represents a hydrogen atom or a methyl group, and L represents a phenyl group), or an acid-decomposable styrenecarboxylic acid tertiary ester-based repeating unit (a repeating unit in which Xb represents a hydrogen atom or a methyl group, and L represents an -Rt-CO— group (Rt is an aromatic group)).

The content of the repeating unit having an acid-decomposable group including an unsaturated bond relative to all the repeating units in the resin (A) is preferably 15 mol % or more, more preferably 20 mol % or more, still more preferably 30 mol % or more. The upper limit value relative to all the repeating units in the resin (A) is preferably 80 mol % or less, more preferably 70 mol % or less, still more preferably 60 mol % or less.

The following are non-limiting specific examples of the repeating unit having an acid-decomposable group including an unsaturated bond. Note that, in the formulas, Xb and $L_1$ represent the above-described substituent or linking group; Ar represent an aromatic group; R represent a substituent such as a hydrogen atom, an alkyl group, a cycloalkyl group, an aryl group, an aralkyl group, an alkenyl group, a hydroxy group, an alkoxy group, an acyloxy group, a cyano group, a nitro group, an amino group, a halogen atom, an ester group (—OCOR''' or —COOR'''; R''' is an alkyl group or a fluorinated alkyl group having 1 to 20 carbon atoms), or a carboxyl group; R' represent a linear or branched alkyl group, a monocyclic or polycyclic cycloalkyl group, an alkenyl group, an alkynyl group, or a monocyclic or polycyclic aryl group; Q represent a heteroatom such as an oxygen atom, a group including a heteroatom such as a carbonyl group, a —$SO_2$— group, or a —$SO_3$— group, a vinylidene group, or a combination of the foregoing; n, m, and l represent an integer of 0 or more.

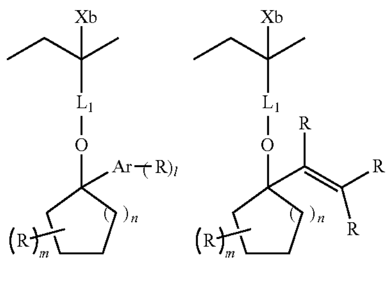

-continued
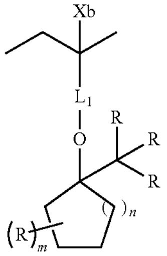
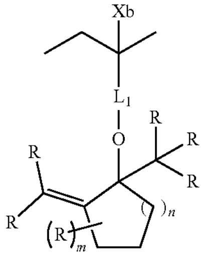
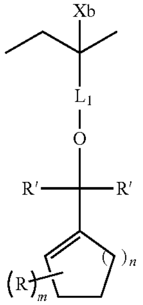
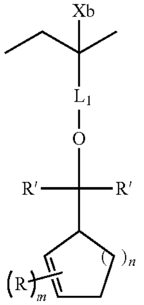
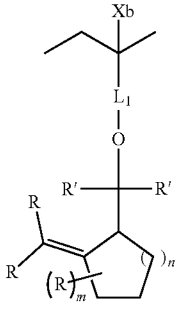
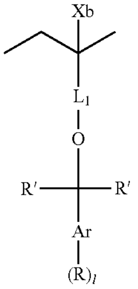
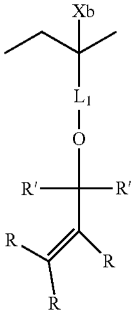
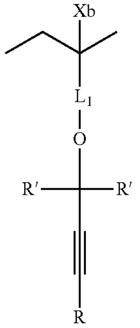
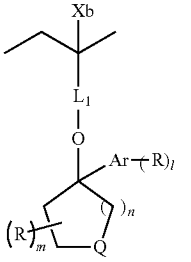
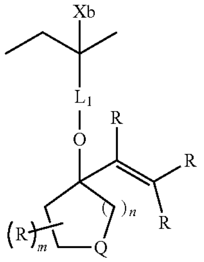
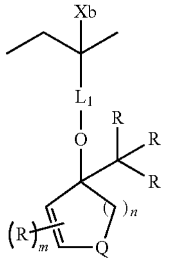
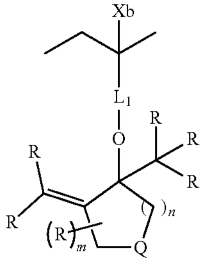
-continued
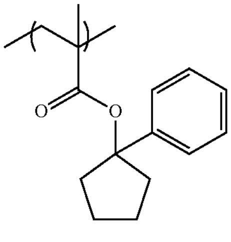
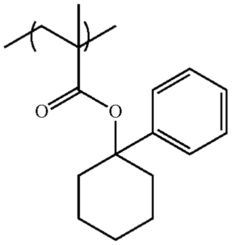
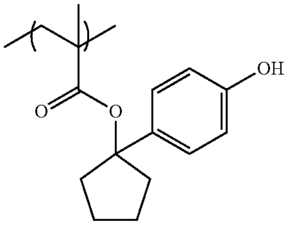
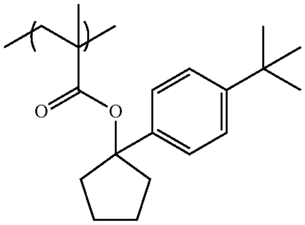
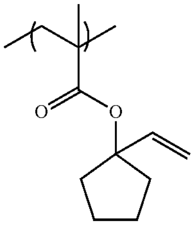
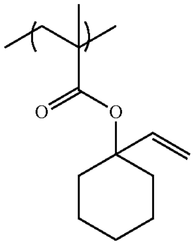
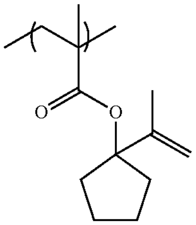
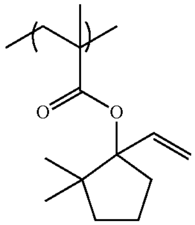
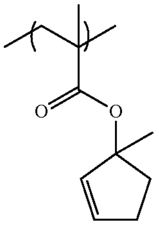
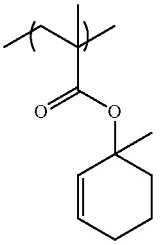
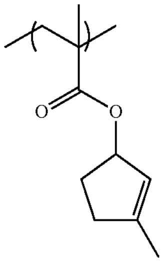
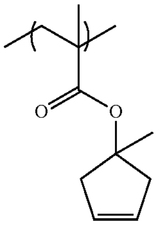
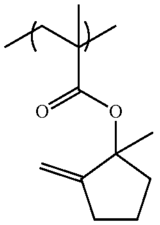
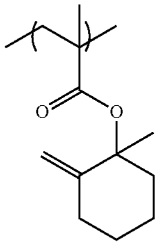

-continued
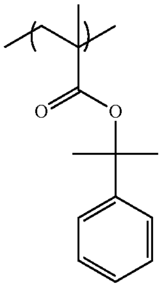
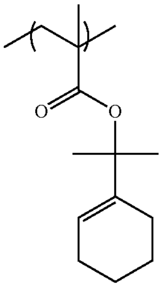
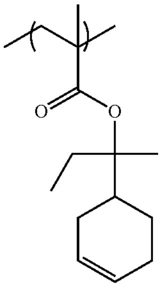
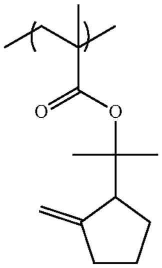
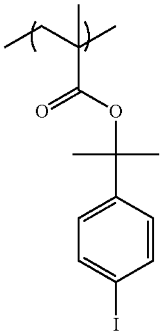
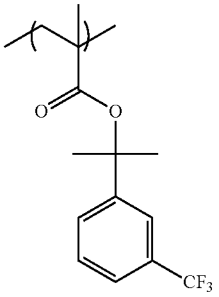
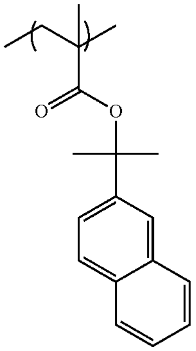
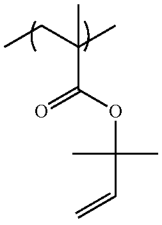
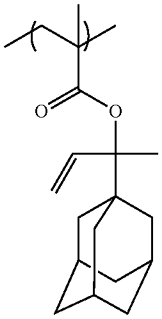
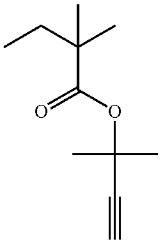
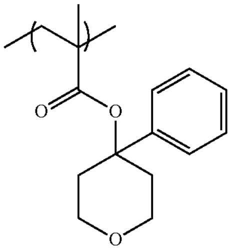
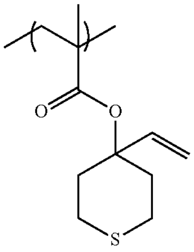
-continued
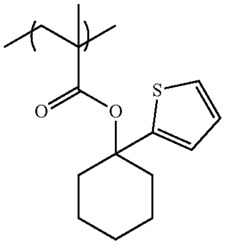
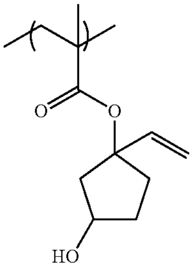
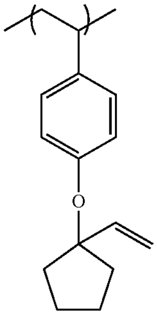
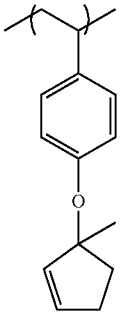
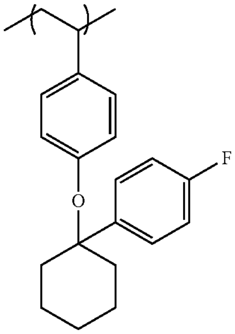
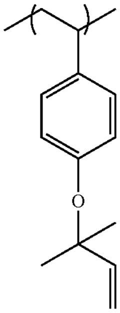
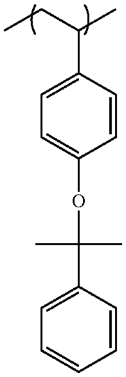
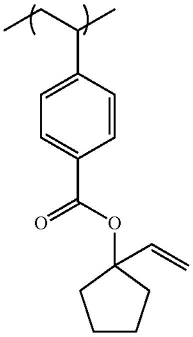
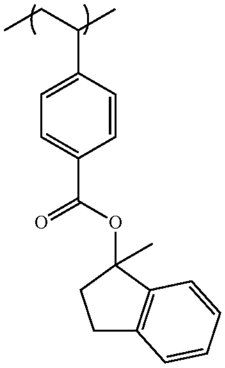
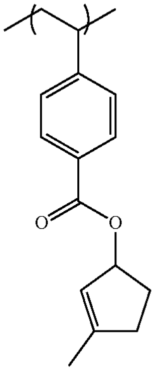

-continued
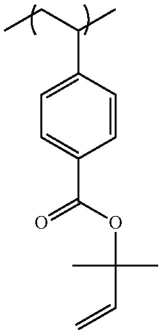
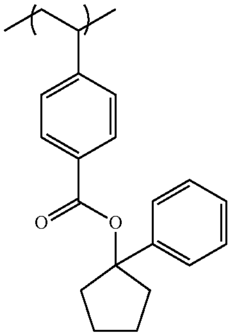
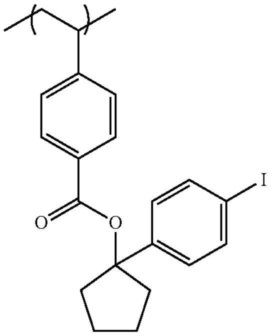
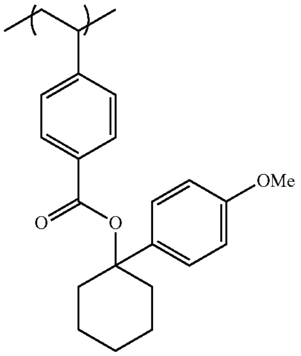
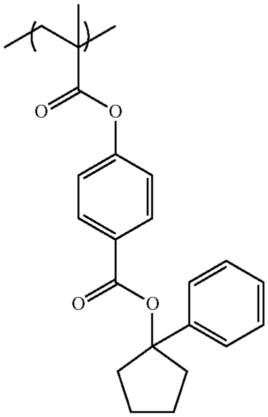
-continued
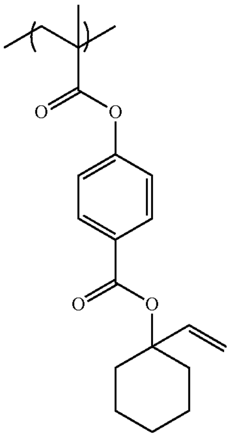
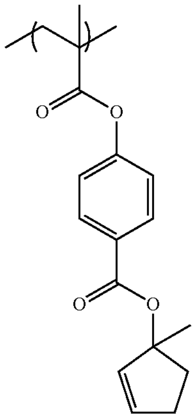
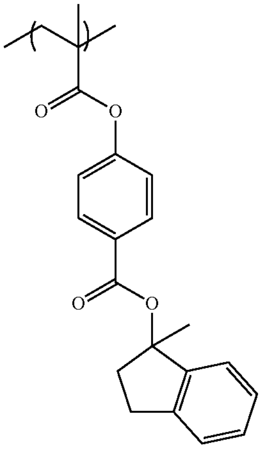
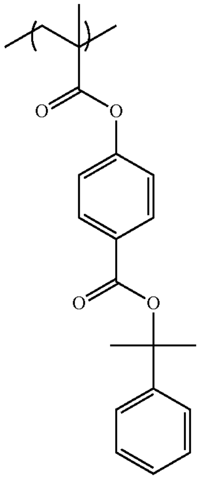
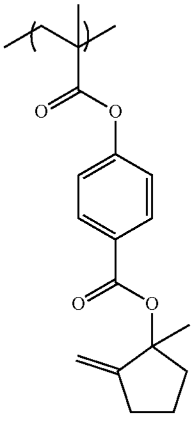
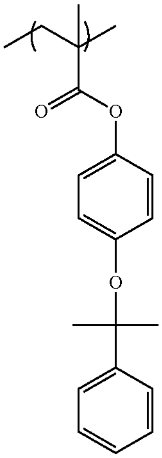

-continued

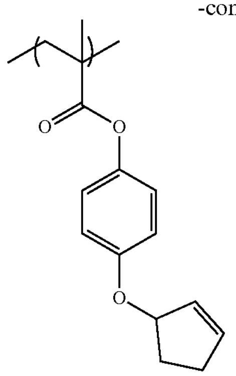

The resin (A) particularly preferably has at least one selected from the group consisting of the repeating unit represented by the following General formula (A1), the repeating unit represented by the following General formula (A2), and the repeating unit represented by the following General formula (A3).

(A1)

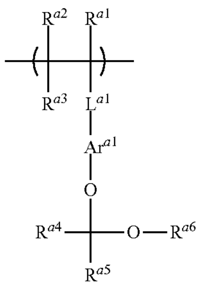

(A2)

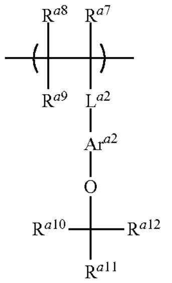

(A3)

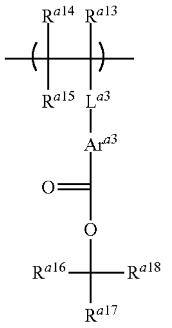

In General formula (A1), $R^{a1}$, $R^{a2}$, and $R^{a3}$ each independently represent a hydrogen atom, an alkyl group, a cycloalkyl group, a halogen atom, a cyano group, or an alkoxycarbonyl group, $L^{a1}$ represents a single bond or a divalent linking group, $Ar^{a1}$ represents an aromatic ring group, $R^{a4}$ represents a hydrogen atom, an alkyl group, a cycloalkyl group, an aryl group, an aralkyl group, or an alkenyl group, $R^{a5}$ and $R^{a6}$ each independently represent an alkyl group, a cycloalkyl group, an aryl group, an aralkyl group, or an alkenyl group, $R^{a4}$ and $R^{a5}$ may be linked together to form a ring, and $Ar^{a1}$ may be linked with $R^{a3}$ or $R^4$ to form a ring.

In General formula (A2), $R^{a7}$, $R^{a8}$, and $R^{a9}$ each independently represent a hydrogen atom, an alkyl group, a cycloalkyl group, a halogen atom, a cyano group, or an alkoxycarbonyl group, $L^{a2}$ represents a single bond or a divalent linking group, $Ar^{a2}$ represents an aromatic ring group, $R^{a10}$, $R^{a11}$, and $R^{a12}$ each independently represent an alkyl group, a cycloalkyl group, an aryl group, an aralkyl group, or an alkenyl group, and two of $R^{a10}$, $R^{a11}$, and $R^{a12}$ may be linked together to form a ring.

In General formula (A3), $R^{a13}$, $R^{a14}$, and $R^{a15}$ each independently represent a hydrogen atom, an alkyl group, a cycloalkyl group, a halogen atom, a cyano group, or an alkoxycarbonyl group, $L^{a3}$ represents a single bond or a divalent linking group, $Ar^3$ represents an aromatic ring group, $R^{a16}$, $R^{a17}$, and $R^{a18}$ each independently represent an alkyl group, a cycloalkyl group, an aryl group, an aralkyl group, or an alkenyl group, and two of $R^{a16}$, $R^{a17}$, and $R^{a18}$ may be linked together to form a ring.

The repeating unit represented by General formula (A1), the repeating unit represented by General formula (A2), and the repeating unit represented by General formula (A3) are repeating units having an acid-decomposable group.

The repeating unit represented by General formula (A1) will be described.

The alkyl groups represented by $R^{a1}$, $R^{a2}$, and $R^{a3}$ may be linear or branched. The number of carbon atoms of such an alkyl group is not particularly limited, but is preferably 1 to 5, more preferably 1 to 3.

The cycloalkyl group represented by $R^{a1}$, $R^{a2}$, and $R^{a3}$ is preferably a monocyclic cycloalkyl group such as a cyclopentyl group or a cyclohexyl group or a polycyclic cycloalkyl group such as a norbornyl group, a tetracyclodecanyl group, a tetracyclododecanyl group, or an adamantyl group.

The halogen atoms represented by $R^{a1}$, $R^{a2}$, and $R^{a3}$ may be, for example, a fluorine atom, a chlorine atom, a bromine atom, or an iodine atom, and are preferably a fluorine atom or an iodine atom.

In the alkoxycarbonyl groups represented by $R^{a1}$, $R^{a2}$, and $R^{a3}$, the alkyl groups may be linear or branched. For the alkyl group included in such an alkoxycarbonyl group, the number of carbon atoms is not particularly limited, but is preferably 1 to 5, more preferably 1 to 3.

When Lai represents a divalent linking group, examples of the divalent linking group include —CO—, —O—, —S—, —SO—, $—SO_2—$, hydrocarbon groups (such as alkylene groups, cycloalkylene groups, alkenylene groups, and arylene groups), and linking groups formed by linking together a plurality of the foregoing.

The aromatic ring group represented by $Ar^{a1}$ is not particularly limited, but may be, for example, a phenylene group or a naphthylene group, and is preferably a phenylene group.

The alkyl groups represented by $R^{a4}$, $R^{a5}$, and $R^{a6}$ may be linear or branched. The number of carbon atoms of such an alkyl group is not particularly limited, but is preferably 1 to 5, more preferably 1 to 3. For the alkyl groups represented by $R^{a4}$, $R^{a5}$, and $R^{a6}$, a methylene group may be replaced by at least one of —CO— or —O—.

The cycloalkyl groups represented by $R^{a4}$, $R^{a5}$, and $R^{a6}$ are preferably monocyclic cycloalkyl groups such as a cyclopentyl group or a cyclohexyl group or polycyclic cycloalkyl groups such as a norbornyl group, a tetracyclodecanyl group, a tetracyclododecanyl group, or an adamantyl group.

The aryl groups represented by $R^{a4}$, $R^{a5}$, and $R^{a6}$ are preferably phenyl groups.

The aralkyl groups represented by $R^{a4}$, $R^{a5}$, and $R^{a6}$ are preferably groups provided by, in each of the alkyl groups represented by $R^{a4}$, $R^{a5}$, and $R^{a6}$, replacing a hydrogen atom by an aryl group having 6 to 10 carbon atoms (preferably a phenyl group); examples include benzyl groups.

The alkenyl groups represented by $R^{a4}$, $R^{a5}$, and $R^{a6}$ are preferably vinyl groups.

The ring formed by linking together $R^{a4}$ and $R^{a5}$ is preferably a cycloalkyl group. The cycloalkyl group formed by linking together $R^{a4}$ and $R^{a5}$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group, more preferably a monocyclic cycloalkyl group having 5 to 6 carbon atoms.

In the cycloalkyl group formed by linking together $R^{a4}$ and $R^{a5}$, for example, one of methylene groups forming the ring may be replaced by a heteroatom such as an oxygen atom, a group having a heteroatom such as a carbonyl group, or a vinylidene group. In the cycloalkyl group, one or more of the ethylene groups forming the cycloalkane ring may be replaced by vinylene groups.

In General formula (A1), the groups may have a substituent and examples of the substituent include the above-described substituent T.

The repeating unit represented by General formula (A2) will be described.

$R^{a7}$, $R^{a8}$, and $R^{a9}$ have the same definitions and preferred examples as in $R^{a1}$, $R^{a2}$, and $R^{a3}$ in General formula (A1).

$L^{a2}$ has the same definition and preferred examples as in $L^{a1}$ in General formula (A1).

$Ar^{a2}$ has the same definition and preferred examples as in $Ar^{a1}$ in General formula (A1).

$R^{a10}$, $R^{a11}$, and $R^{a12}$ have the same definitions and preferred examples as in $R^{a4}$, $R^{a5}$, and $R^{a6}$ in General formula (A1).

The ring formed by linking together two of $R^{a10}$, $R^{a11}$, and $R^{a12}$ is preferably a cycloalkyl group. The cycloalkyl group formed by linking together two of $R^{a10}$, $R^{a11}$, and $R^{a12}$ is preferably a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group, more preferably a monocyclic cycloalkyl group having 5 to 6 carbon atoms.

In the cycloalkyl group formed by linking together two of $R^{a10}$, $R^{a11}$, and $R^{a12}$, one of methylene groups forming the ring may be replaced by a heteroatom such as an oxygen atom, a group including a heteroatom such as a carbonyl group, or a vinylidene group. In the cycloalkyl group, one or more of the ethylene groups forming the cycloalkane ring may be replaced by vinylene groups.

In General formula (A2), the groups may have a substituent and examples of the substituent include the above-described substituent T.

The repeating unit represented by General formula (A3) will be described.

$R^{a13}$, $R^{a14}$, and $R^{a15}$ have the same definitions and preferred examples as in $R^{a1}$, $R^{a2}$, and $R^{a3}$ in General formula (A1).

$L^{a3}$ has the same definition and preferred examples as in $L^{a1}$ in General formula (A1).

$Ar^{a3}$ has the same definition and preferred examples as in $Ar^{a3}$ in General formula (A1).

$R^{a16}$, $R^{a17}$, and $R^{a18}$ have the same definitions and preferred examples as in $R^{a4}$, $R^{a5}$, and $R^{a6}$ in General formula (A1).

The ring formed by linking together two of $R^{a16}$, $R^{a17}$, and $R^{a18}$ is the same as the ring formed by linking together two of $R^{a10}$, $R^{a11}$, and $R^{a12}$ in General formula (A2).

In General formula (A3), the groups may have a substituent and examples of the substituent include the above-described substituent T.

The following are non-limiting specific examples of the repeating unit represented by General formula (A1), the repeating unit represented by General formula (A2), and the repeating unit represented by General formula (A3).

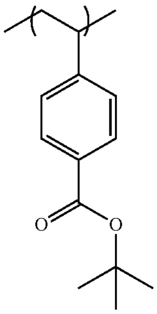
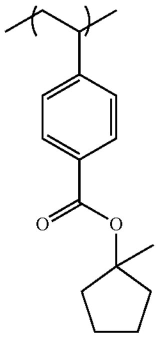
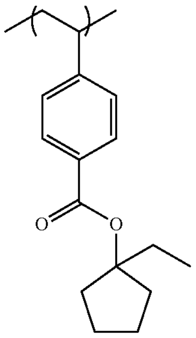
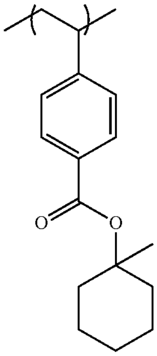
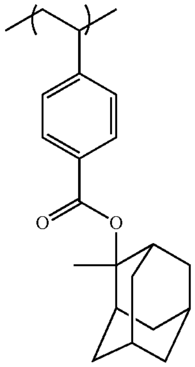
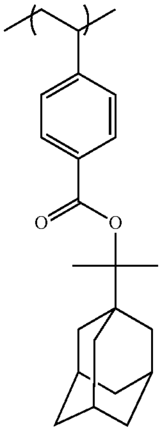
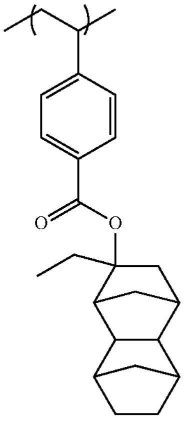

-continued

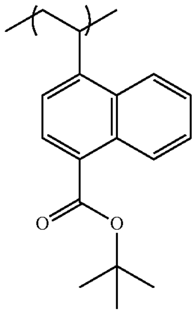
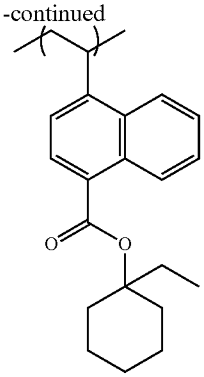
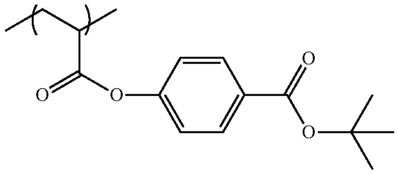
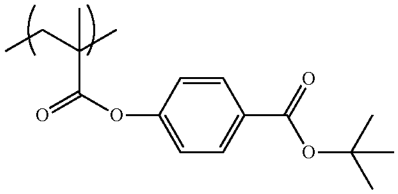
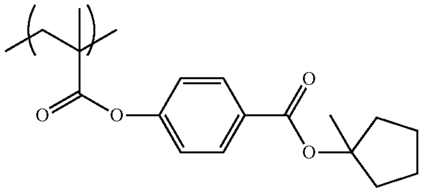
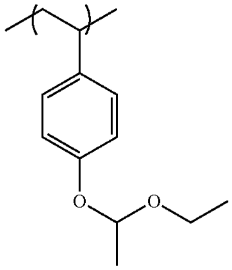
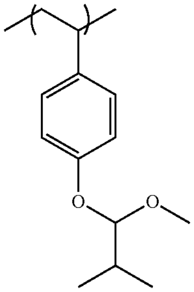
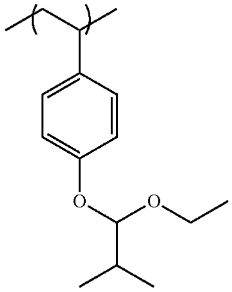
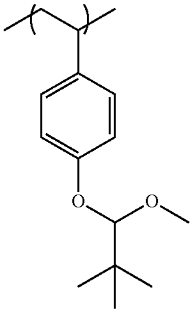

-continued

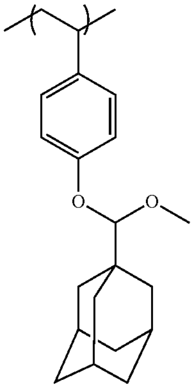
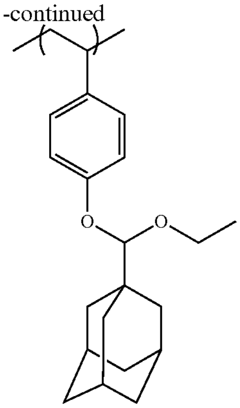
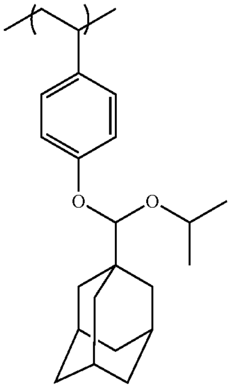
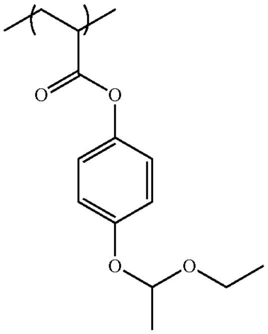
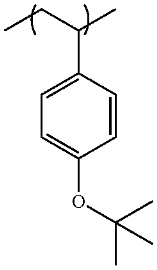
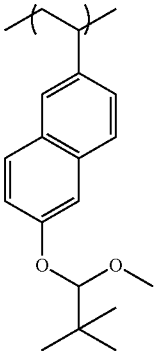
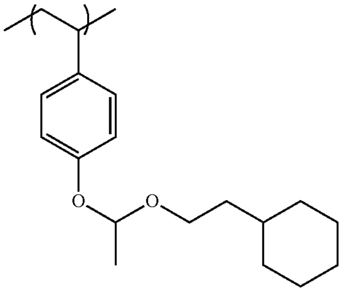

The content of the repeating unit having an acid-decomposable group relative to all the repeating units in the resin (A) is preferably 15 mol % or more, more preferably 20 mol % or more, still more preferably 30 mol % or more. The upper limit value relative to all the repeating units in the resin (A) is preferably 90 mol % or less, more preferably 80 mol % or less, still more preferably 70 mol % or less, particularly preferably 60 mol % or less.

The resin (A) may include at least one repeating unit species selected from the group consisting of the following Group A and/or at least one repeating unit species selected from the group consisting of the following Group B.

Group A: group consisting of the following repeating units (20) to (25)

(20) a repeating unit having an acid group described later

(21) a repeating unit not having an acid-decomposable group or an acid group, but having a fluorine atom, a bromine atom, or an iodine atom described later

(22) a repeating unit having a lactone group, a sultone group, or a carbonate group described later

(23) a repeating unit having a photoacid generation group described later

(24) a repeating unit represented by Formula (V-1) or Formula (V-2) below described later

(25) a repeating unit for lowering the mobility of main chains

Note that repeating units represented by Formula (A) to Formula (E) described later correspond to the repeating unit (25) for lowering the mobility of main chains.

Group B: group consisting of the following repeating units (30) to (32)

(30) a repeating unit having at least one group species selected from the group consisting of a lactone group, a sultone group, a carbonate group, a hydroxy group, a cyano group, and an alkali-soluble group described later

(31) a repeating unit having an alicyclic hydrocarbon structure and not exhibiting acid decomposability described later

(32) a repeating unit not having a hydroxy group or a cyano group and represented by Formula (III) described later The resin (A) preferably has an acid group and preferably includes a repeating unit having an acid group as described later. Note that the definition of the acid group will be described in a later part together with preferred examples of the repeating unit having an acid group. When the resin (A) has an acid group, a better interaction between the resin (A) and the acid generated from the photoacid generator is provided. This results in further suppression of diffusion of the acid to form a pattern having a more square profile.

The resin (A) may have at least one repeating unit species selected from the group consisting of Group A above. When the actinic ray-sensitive or radiation-sensitive resin composition is used as an EUV-exposure actinic ray-sensitive or radiation-sensitive resin composition, the resin (A) preferably has at least one repeating unit species selected from the group consisting of Group A above.

The resin (A) may include at least one of a fluorine atom or an iodine atom. When the actinic ray-sensitive or radiation-sensitive resin composition is used as an EUV-exposure actinic ray-sensitive or radiation-sensitive resin composition, the resin (A) preferably includes at least one of a fluorine atom or an iodine atom. When the resin (A) includes both of a fluorine atom and an iodine atom, the resin (A) may have a repeating unit including both of a fluorine atom and an iodine atom, or the resin (A) may include two species that are a repeating unit having a fluorine atom and a repeating unit including an iodine atom.

The resin (A) may have a repeating unit having an aromatic group. When the actinic ray-sensitive or radiation-sensitive resin composition is used as an EUV-exposure actinic ray-sensitive or radiation-sensitive resin composition, the resin (A) also preferably has a repeating unit having an aromatic group.

The resin (A) may also have at least one repeating unit species selected from the group consisting of Group B above. When the actinic ray-sensitive or radiation-sensitive resin composition is used as an ArF actinic ray-sensitive or radiation-sensitive resin composition, the resin (A) preferably has at least one repeating unit species selected from the group consisting of Group B above.

Note that, when the actinic ray-sensitive or radiation-sensitive resin composition is used as an ArF actinic ray-sensitive or radiation-sensitive resin composition, the resin (A) preferably does not include a fluorine atom or a silicon atom.

When the actinic ray-sensitive or radiation-sensitive resin composition is used as an ArF actinic ray-sensitive or radiation-sensitive resin composition, the resin (A) preferably does not have an aromatic group.

Repeating Unit Having Acid Group

The resin (A) may have a repeating unit having an acid group.

The acid group is preferably an acid group having a pKa of 13 or less. The acid group preferably has an acid dissociation constant of 13 or less, more preferably 3 to 13, still more preferably 5 to 10.

When the resin (A) has an acid group having a pKa of 13 or less, the content of the acid group in the resin (A) is not particularly limited, but is often 0.2 to 6.0 mmol/g, in particular, preferably 0.8 to 6.0 mmol/g, more preferably 1.2 to 5.0 mmol/g, still more preferably 1.6 to 4.0 mmol/g. When the content of the acid group is within such a range, development suitably proceeds to form a pattern having a good profile at high resolution.

The acid group is preferably, for example, a carboxyl group, a phenolic hydroxy group, a fluoroalcohol group (preferably a hexafluoroisopropanol group), a sulfonic group, a sulfonamide group, or an isopropanol group.

In the hexafluoroisopropanol group, one or more (preferably one to two) of the fluorine atoms may be substituted with groups other than fluorine atoms (such as alkoxycarbonyl groups). The acid group is also preferably $—C(CF_3)(OH)—CF_2—$ formed in this manner. Alternatively, one or more of the fluorine atoms may be substituted with groups other than fluorine atoms, to form a ring including $—C(CF_3)(OH)—CF_2—$.

The repeating unit having an acid group is preferably a repeating unit different from the above-described repeating unit having a structure in which a polar group is protected with a group that leaves due to the action of acid and repeating units described later and having a lactone group, sultone group, or a carbonate group.

The repeating unit having an acid group may have a fluorine atom or an iodine atom.

Examples of the repeating unit having an acid group include the following repeating units.

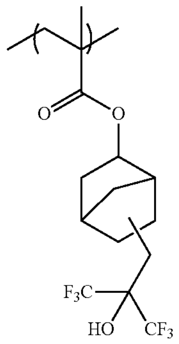

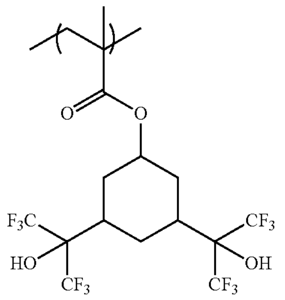

-continued

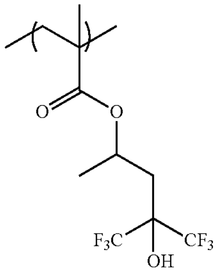

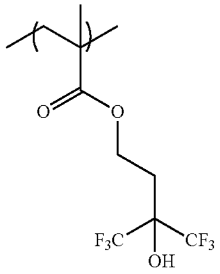

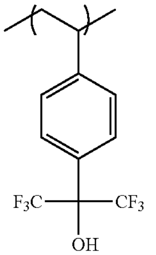

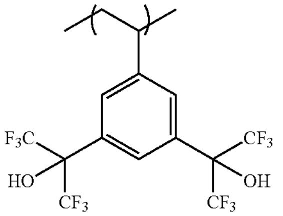

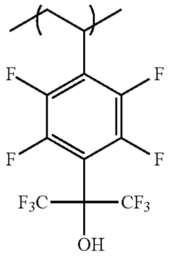

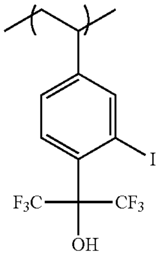

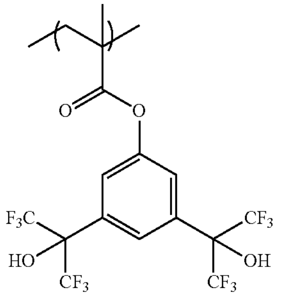

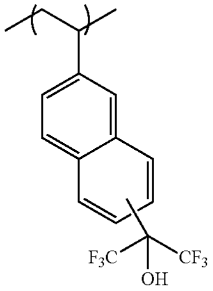

The repeating unit having an acid group is preferably a repeating unit represented by the following Formula (1).

(1)

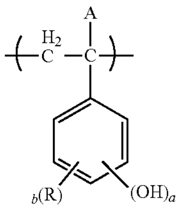

In Formula (1), A represents a hydrogen atom, an alkyl group, a cycloalkyl group, a halogen atom, or a cyano group. R represents a halogen atom, an alkyl group, a cycloalkyl group, an aryl group, an alkenyl group, an aralkyl group, an alkoxy group, an alkylcarbonyloxy group, an alkylsulfonyloxy group, an alkyloxycarbonyl group, or an aryloxycarbonyl group; when there are a plurality of R's, they may be the same or different. When Formula (1) has a plurality of R's, they may together form a ring. R is preferably a hydrogen atom. a represents an integer of 1 to 3. b represents an integer of 0 to (5−a).

The following are examples of the repeating unit having an acid group. In the formulas, a represent 1 or 2.

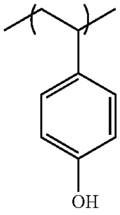

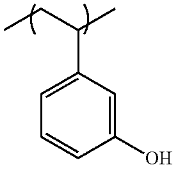

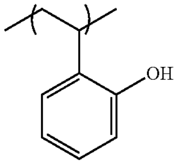

(B-1)

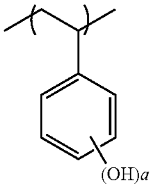

(B-2)

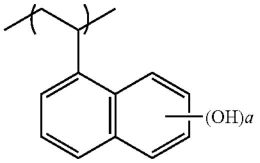

(B-3)

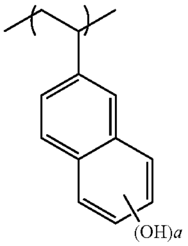

(B-4)

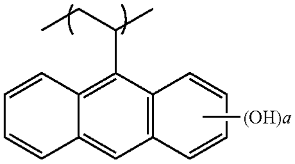

(B-5)

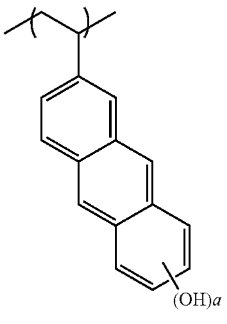

-continued
(B-6)
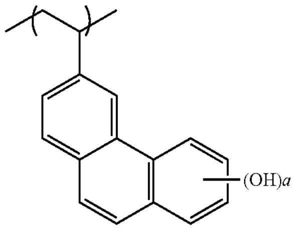
(B-7)
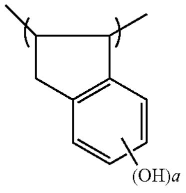
(B-8)
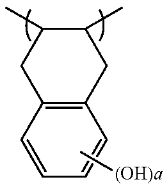
(B-9)
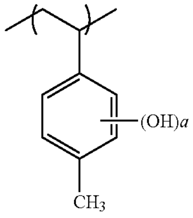
(B-10)
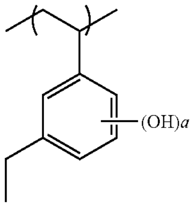
(B-11)
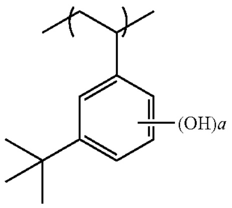
(B-12)
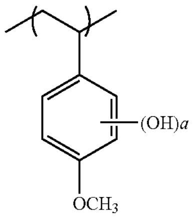
-continued
(B-13)
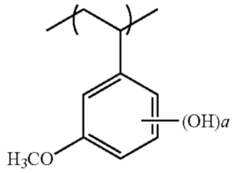
(B-14)
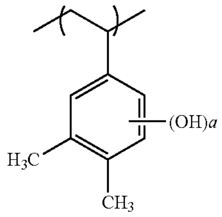
(B-15)
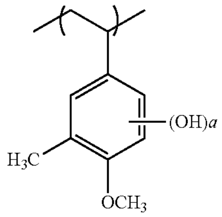
(B-16)
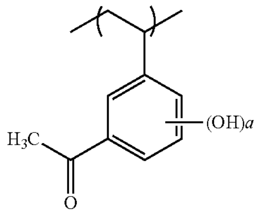
(B-17)
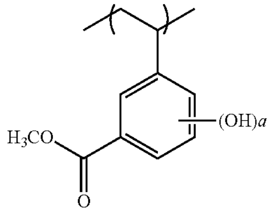
(B-18)
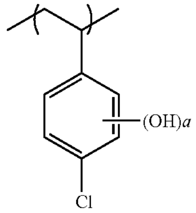
(B-19)
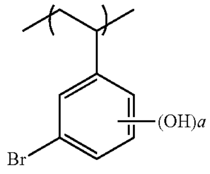

-continued
(B-20)
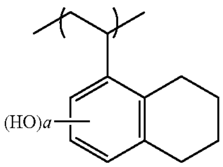
(B-21)
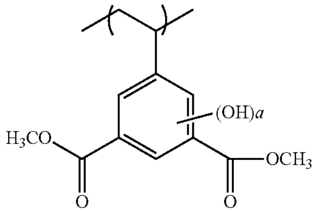
(B-22)
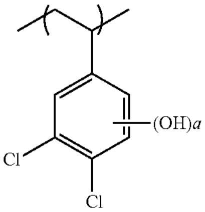
(B-23)
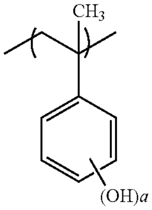
(B-24)
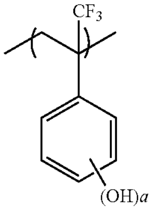
(B-25)
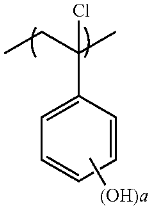
(B-26)
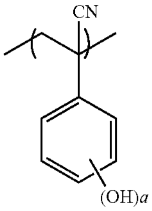
-continued
(B-27)
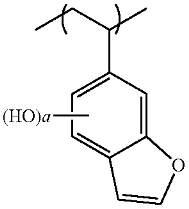
(B-28)
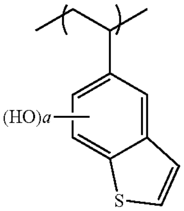
(B-29)
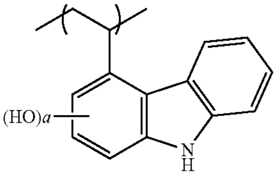
(B-30)
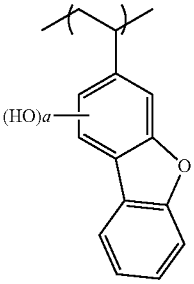
(B-31)
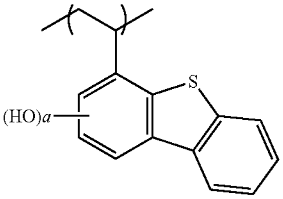
(B-32)
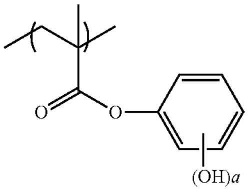
(B-33)
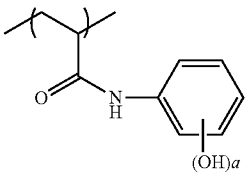

-continued
(B-34)
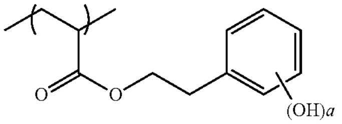
(B-35)
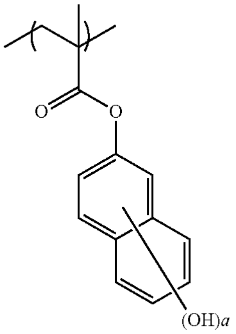
(B-36)
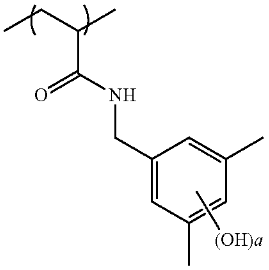
(B-37)
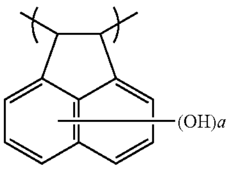
(B-38)
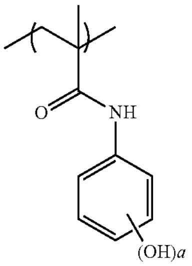
Note that, of the repeating units, preferred are the following specific repeating units. In the formulas, R represent a hydrogen atom or a methyl group, and a represent 2 or 3.
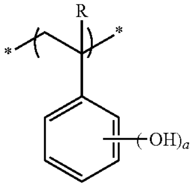
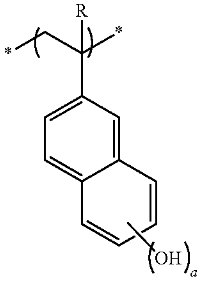
-continued
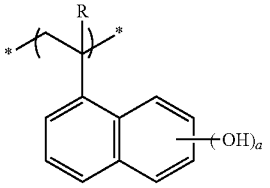
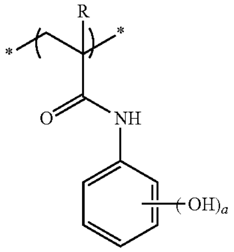
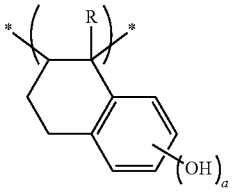
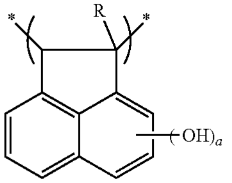
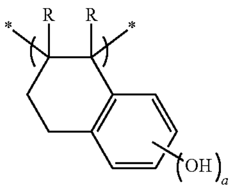
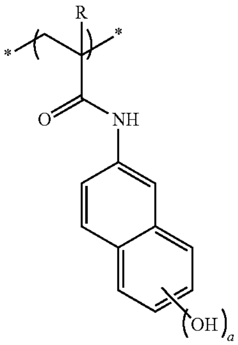
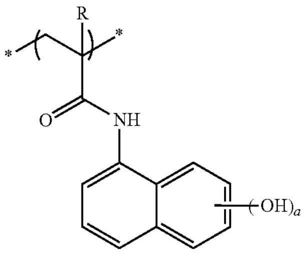
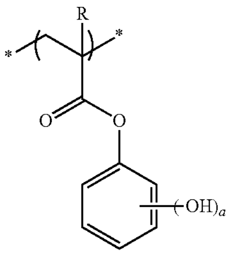
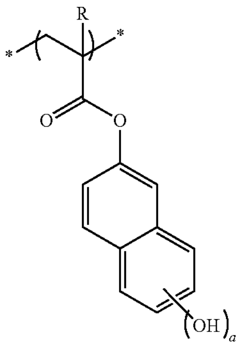
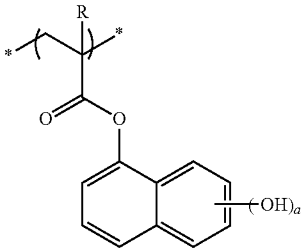

-continued

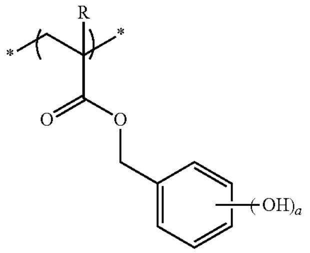

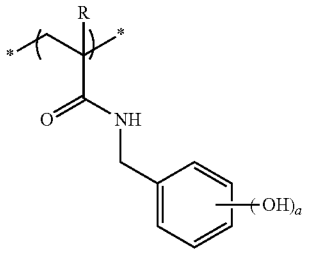

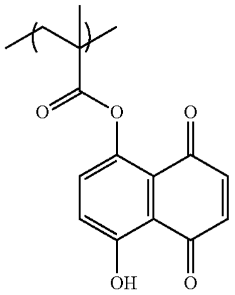

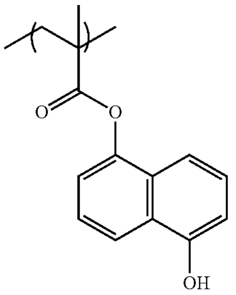

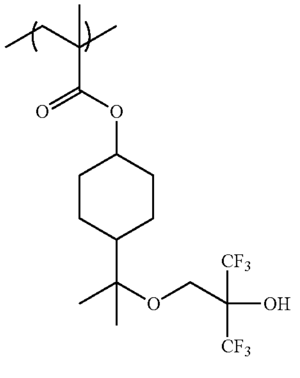

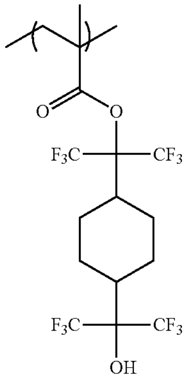

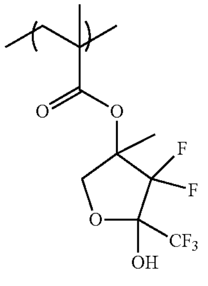

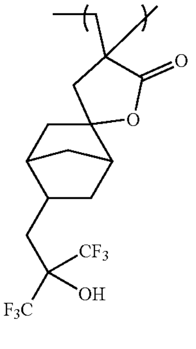

-continued

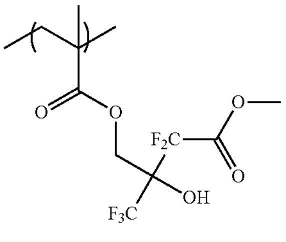

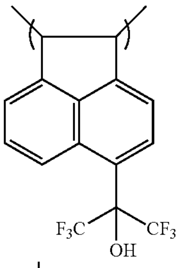

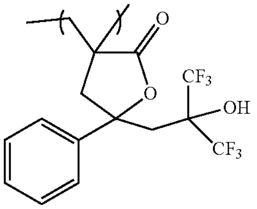

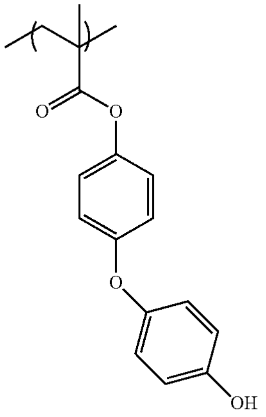

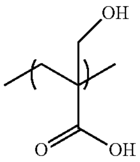

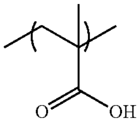

The content of the repeating unit having an acid group relative to all the repeating units in the resin (A) is preferably 10 mol % or more, more preferably 15 mol % or more. The upper limit value relative to all the repeating units in the resin (A) is preferably 70 mol % or less, more preferably 65 mol % or less, still more preferably 60 mol % or less.

Repeating Unit not Having Acid-Decomposable Group or Acid Group, but Having Fluorine Atom, Bromine Atom, or Iodine Atom The resin (A) may have, in addition to the above-described <repeating unit having an acid-decomposable group> and <repeating unit having an acid group>, a repeating unit not having an acid-decomposable group or an acid group, but having a fluorine atom, a bromine atom, or an iodine atom (hereafter, also referred to as the unit X). This <repeating unit not having an acid-decomposable group or an acid group, but having a fluorine atom, a bromine atom, or an iodine atom> is preferably different from other repeating unit species belonging to Group A such as a <repeating unit having a lactone group, a sultone group, or a carbonate group> and a <repeating unit having a photoacid generation group> described later.

The unit X is preferably a repeating unit represented by Formula (C).

(C)

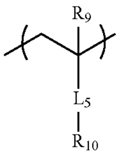

$L_5$ represents a single bond or an ester group. Re represents an alkyl group that may have a hydrogen atom, a fluorine atom, or an iodine atom. $R_{10}$ represents an alkyl group that may have a hydrogen atom, a fluorine atom, or an iodine atom, a cycloalkyl group that may have a fluorine atom or an iodine atom, an aryl group that may have a fluorine atom or an iodine atom, or a group provided as a combination of the foregoing.

The following are examples of the repeating unit having a fluorine atom or an iodine atom.

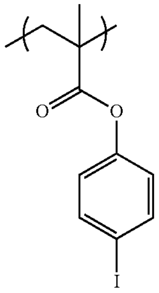

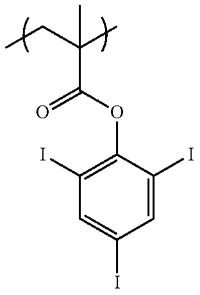

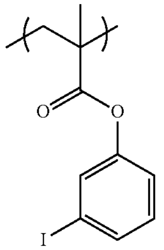

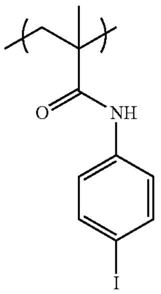

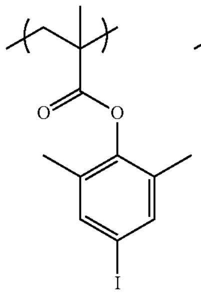

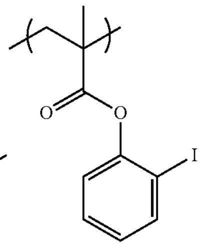

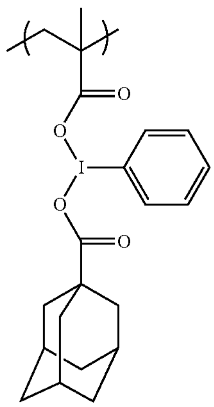

-continued

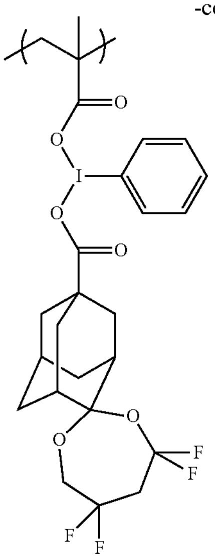

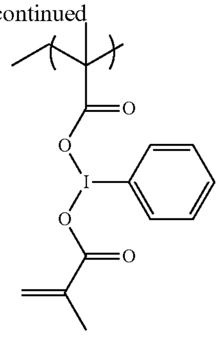

The unit X content relative to all the repeating units in the resin (A) is preferably 0 mol % or more, more preferably 5 mol % or more, still more preferably 10 mol % or more. The upper limit value relative to all the repeating units in the resin (A) is preferably 50 mol % or less, more preferably 45 mol % or less, still more preferably 40 mol % or less.

Of the repeating units of the resin (A), the total content of the repeating unit including at least one of a fluorine atom, a bromine atom, or an iodine atom relative to all the repeating units of the resin (A) is preferably 10 mol % or more, more preferably 20 mol % or more, still more preferably 30 mol % or more, particularly preferably 40 mol % or more. The upper limit value is not particularly limited, but is, for example, relative to all the repeating units of the resin (A), 100 mol % or less.

Note that examples of the repeating unit including at least one of a fluorine atom, a bromine atom, or an iodine atom include a repeating unit having a fluorine atom, a bromine atom, or an iodine atom and having an acid-decomposable group, a repeating unit having a fluorine atom, a bromine atom, or an iodine atom and having an acid group, and a repeating unit having a fluorine atom, a bromine atom, or an iodine atom.

Repeating Unit Having Lactone Group, Sultone Group, or Carbonate Group

The resin (A) may have a repeating unit having at least one species selected from the group consisting of a lactone group, a sultone group, and a carbonate group (hereafter, also referred to as the "unit Y").

The unit Y also preferably does not have acid groups such as a hydroxy group and a hexafluoropropanol group.

The lactone group or the sultone group at least has a lactone structure or a sultone structure. The lactone structure or the sultone structure is preferably a five- to seven-membered lactone structure or a five- to seven-membered sultone structure. In particular, more preferred is a five- to seven-membered lactone structure to which another ring structure is fused so as to form a bicyclo structure or a spiro structure, or a five- to seven-membered sultone structure to which another ring structure is fused so as to form a bicyclo structure or a spiro structure.

The resin (A) preferably has a repeating unit having a lactone group or a sultone group provided by withdrawing, from ring-member atoms of the lactone structure represented by any one of Formulas (LC1-1) to (LC1-21) below or the sultone structure represented by any one of Formulas (SL1-1) to (SL1-3) below, one or more hydrogen atoms, and a lactone group or a sultone group may be directly bonded to the main chain. For example, ring-member atoms of a lactone group or a sultone group may constitute the main chain of the resin (A).

LC1-1

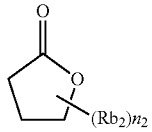

LC1-2

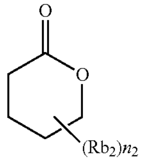

LC1-3

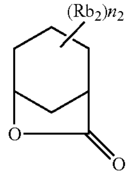

LC1-4

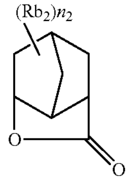

LC1-5

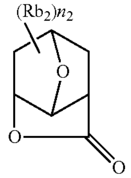

LC1-6

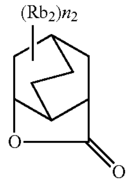

LC1-7

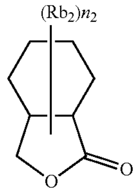

-continued

LC1-8

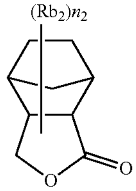

LC1-9

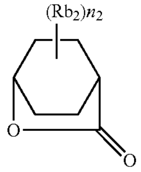

LC1-10

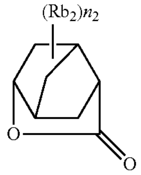

LC1-11

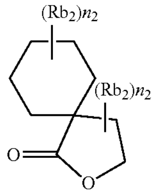

LC1-12

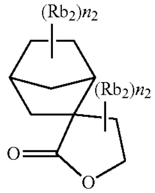

LC1-13

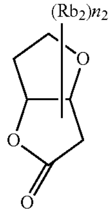

LC1-14

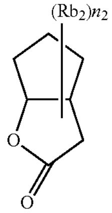

LC1-15

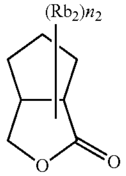

-continued

LC1-16

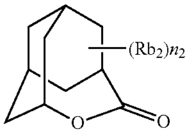

LC1-17

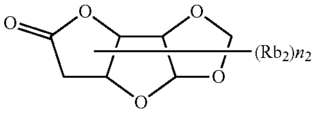

LC1-18

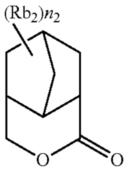

LC1-19

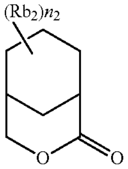

LC1-20

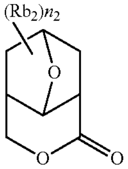

LC1-21

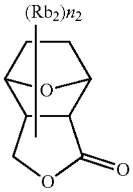

SL1-1

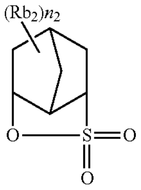

SL1-2

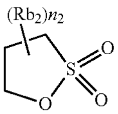

SL1-3

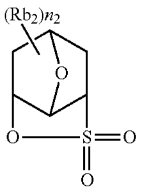

The lactone structure or the sultone structure may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, halogen atoms, a cyano group, and acid-decomposable groups. n2 represents an integer of 0 to 4. When n2 is 2 or more, a plurality of $Rb_2$'s may be different and a plurality of $Rb_2$'s may be linked together to form a ring.

The repeating unit having a group including the lactone structure represented by any one of Formulas (LC1-1) to (LC1-21) or the sultone structure represented by any one of Formulas (SL1-1) to (SL1-3) is, for example, a repeating unit represented by the following Formula (AI).

(AI)

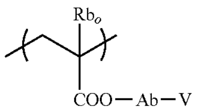

In Formula (AI), $Rb_0$ represents a hydrogen atom, a halogen atom, or an alkyl group having 1 to 4 carbon atoms. Preferred examples of the substituent that the alkyl group of $Rb_0$ may have include a hydroxy group and a halogen atom. Examples of the halogen atom of $Rb_0$ include a fluorine atom, a chlorine atom, a bromine atom, and an iodine atom. $Rb_0$ is preferably a hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent linking group being a combination of the foregoing. In particular, Ab is preferably a single bond or a linking group represented by $-Ab_1-CO_2-$. $Ab_1$ is a linear or branched alkylene group or a monocyclic or polycyclic cycloalkylene group, preferably a methylene group, an ethylene group, a cyclohexylene group, an adamantylene group, or a norbornylene group.

V represents a group formed by withdrawing, from a ring-member atom of the lactone structure represented by any one of Formulas (LC1-1) to (LC1-21), a single hydrogen atom, or a group formed by withdrawing, from a ring-member atom of the sultone structure represented by any one of Formulas (SL1-1) to (SL1-3), a single hydrogen atom.

When the repeating unit having a lactone group or a sultone group has an optical isomer, any optical isomer may be used. A single optical isomer may be used alone, or a plurality of optical isomers may be used in combination. In the case of mainly using a single optical isomer, its optical purity (ee) is preferably 90 or more, more preferably 95 or more.

The carbonate group is preferably a cyclic carbonic acid ester group.

The repeating unit having a cyclic carbonic acid ester group is preferably a repeating unit represented by the following Formula (A-1).

(A-1)

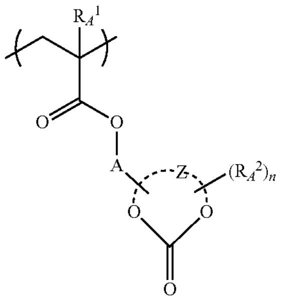

In Formula (A-1), $R_A^1$ represents a hydrogen atom, a halogen atom, or a monovalent organic group (preferably a methyl group). n represents an integer of 0 or more. $R_A^2$ represents a substituent. When n is 2 or more, a plurality of $R_A^2$'s may be the same or different. A represents a single bond or a divalent linking group. The divalent linking group is preferably an alkylene group, a divalent linking group having a monocyclic or polycyclic alicyclic hydrocarbon structure, an ether group, an ester group, a carbonyl group, a carboxyl group, or a divalent linking group being a combination of the foregoing. Z represents an atomic group that forms, together with the group represented by —O—CO—O— in the formula, a monocyclic ring or a polycyclic ring.

The following are examples of the unit Y. In the formulas, Rx represent a hydrogen atom, —$CH_3$, —$CH_2OH$, or —$CF_3$.

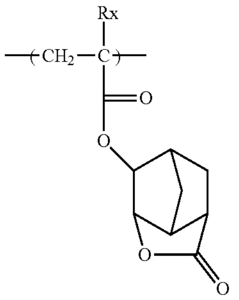
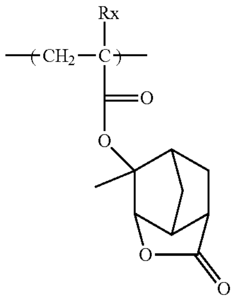

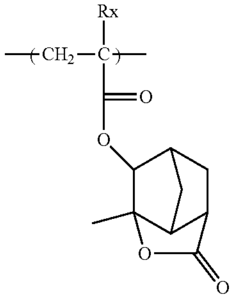
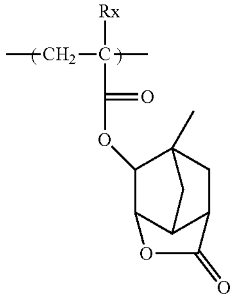

-continued

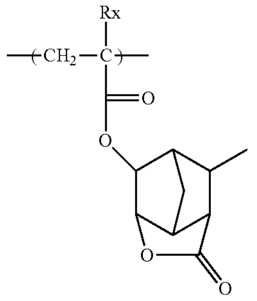
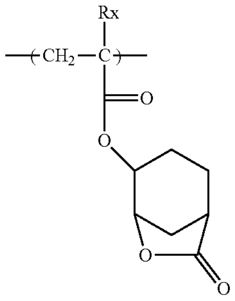

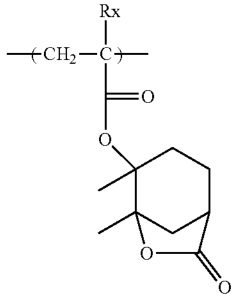
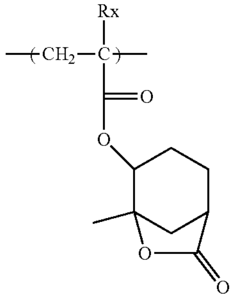

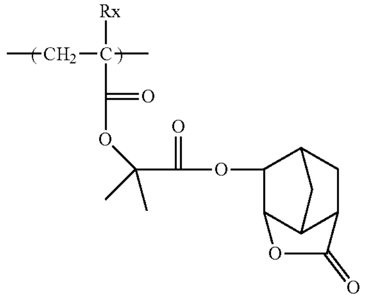

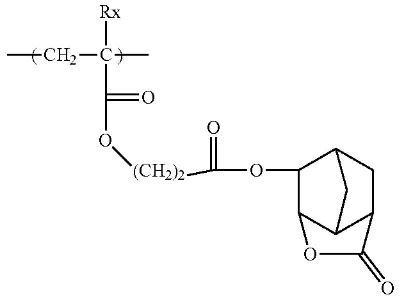

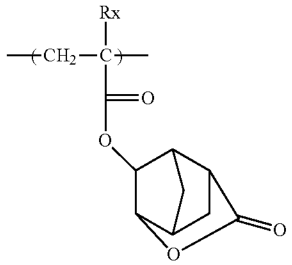

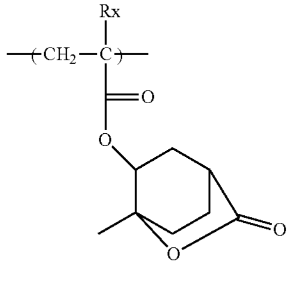

-continued
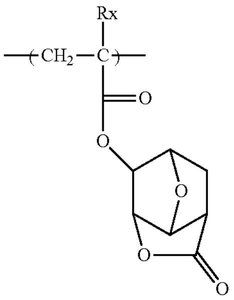
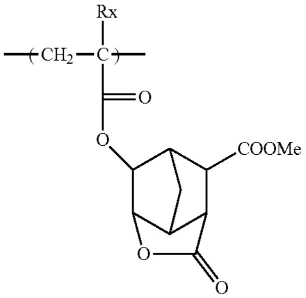
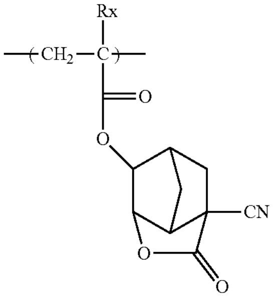
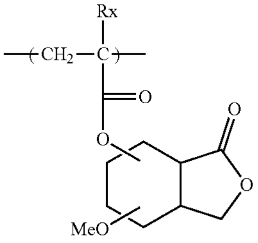
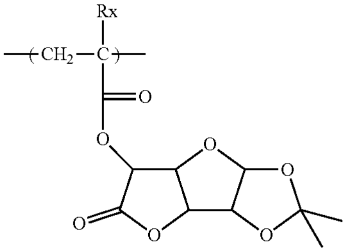
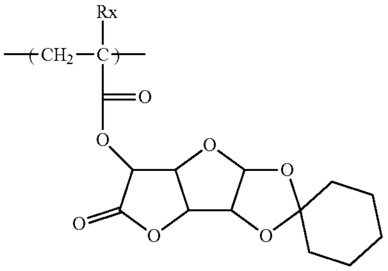
-continued
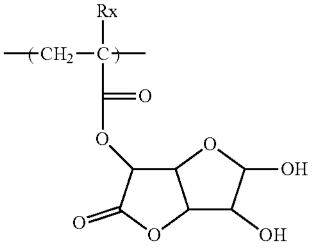
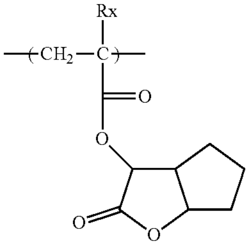
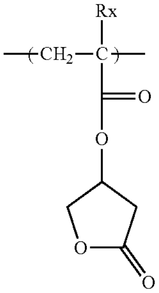
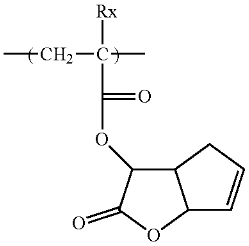
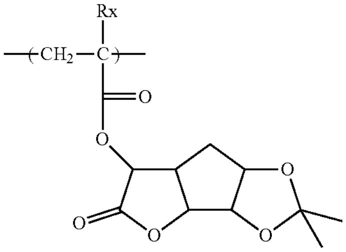
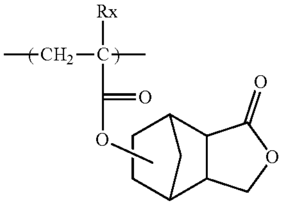
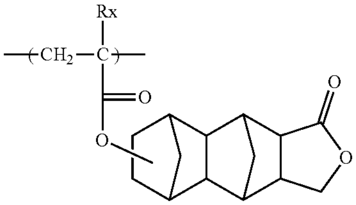

(in the formulas, $R_x$ represent H, $CH_3$, $CH_2OH$, or $CF_3$)
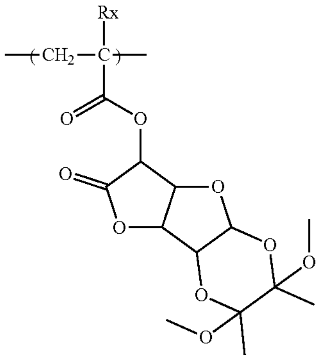
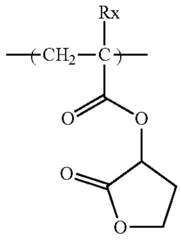
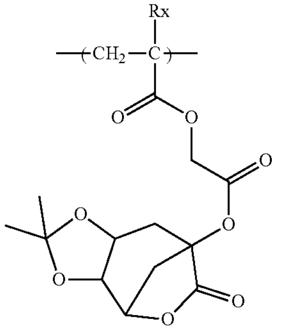
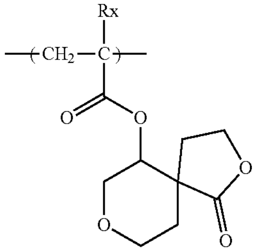
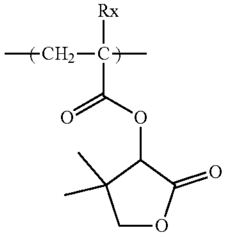
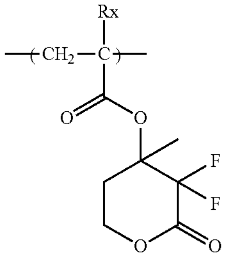
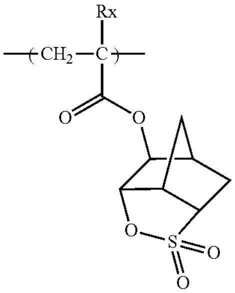
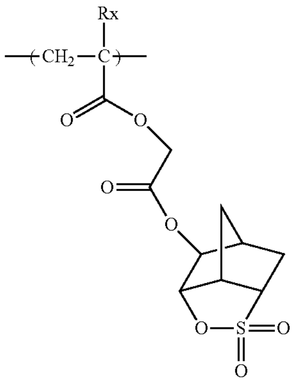
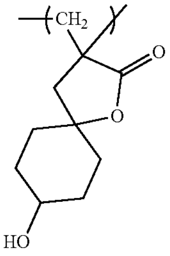
-continued
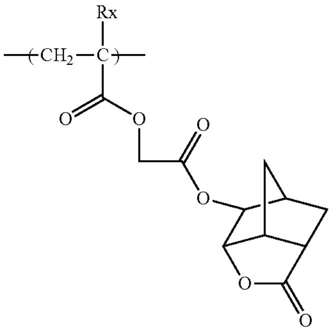
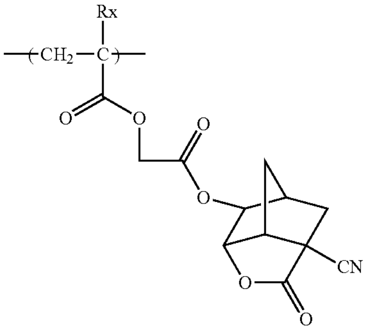
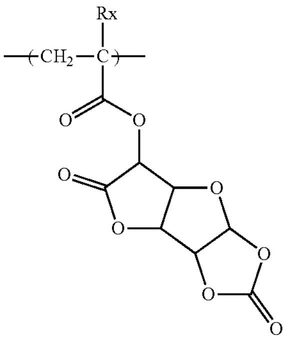
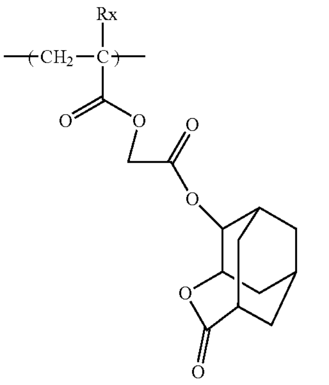
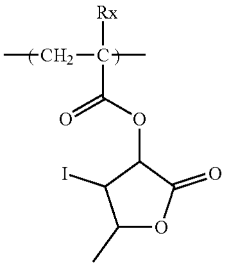

(in the formulas, $R_x$ represent H, $CH_3$, $CH_2OH$, or $CF_3$)

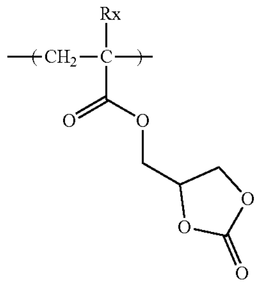

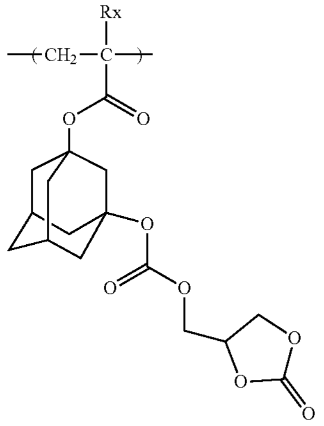

The unit Y content relative to all the repeating units in the resin (A) is preferably 1 mol % or more, more preferably 10 mol % or more. The upper limit value relative to all the repeating units in the resin (A) is preferably 85 mol % or less, more preferably 80 mol % or less, still more preferably 70 mol % or less, particularly preferably 60 mol % or less.

Repeating Unit Having Photoacid Generation Group

The resin (A) may have, as another repeating unit, a repeating unit having a group that generates acid in response to irradiation with an actinic ray or radiation (also referred to as "photoacid generation group").

The repeating unit having a photoacid generation group may be a repeating unit represented by Formula (4).

(4)

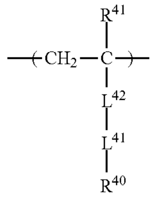

$R^{41}$ represents a hydrogen atom or a methyl group. $L^{41}$ represents a single bond or a divalent linking group. $L^{42}$ represents a divalent linking group. $R^{40}$ represents a moiety that is decomposed in response to irradiation with an actinic ray or radiation to generate acid in the side chain.

The following are examples of the repeating unit having a photoacid generation group.

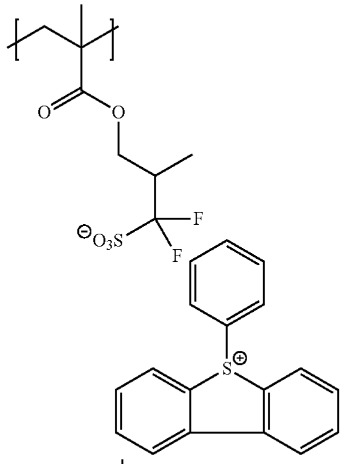

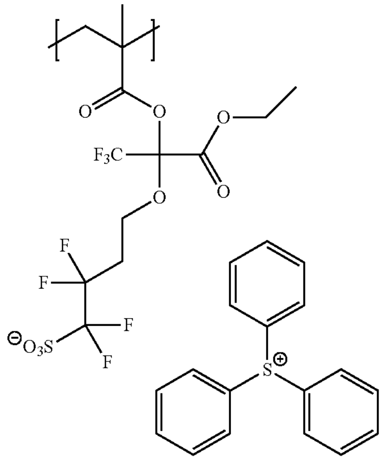

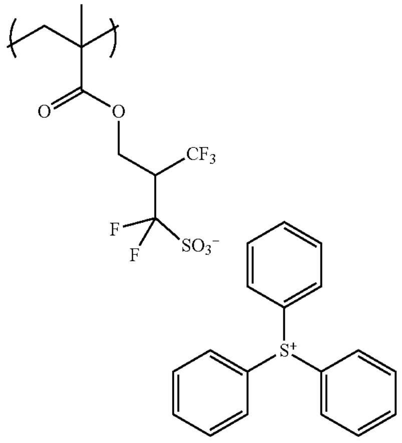

Other examples of the repeating unit represented by Formula (4) include the repeating units described in Paragraphs [0094] to [0105] of JP2014-041327A and the repeating units described in Paragraph [0094] of WO2018/193954A.

The content of the repeating unit having a photoacid generation group relative to all the repeating units in the resin (A) is preferably 1 mol % or more, more preferably 5 mol % or more. The upper limit value relative to all the repeating units in the resin (A) is preferably 40 mol % or less, more preferably 35 mol % or less, still more preferably 30 mol % or less. Repeating unit represented by Formula (V-1) or Formula (V-2) below The resin (A) may have a repeating unit represented by Formula (V-1) below or Formula (V-2) below.

The repeating unit represented by Formula (V-1) below or Formula (V-2) below is preferably a repeating unit different from the above-described repeating units.

(V-1)

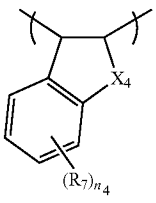

(V-2)

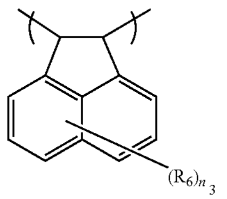

In the formulas, $R_6$ and $R_7$ each independently represent a hydrogen atom, a hydroxy group, an alkyl group, an alkoxy group, an acyloxy group, a cyano group, a nitro group, an amino group, a halogen atom, an ester group (—OCOR or —COOR: R represents an alkyl group or fluorinated alkyl group having 1 to 6 carbon atoms), or a carboxyl group. The alkyl group is preferably a linear, branched, or cyclic alkyl group having 1 to 10 carbon atoms.

$n_3$ represents an integer of 0 to 6.

$n_4$ represents an integer of 0 to 4.

$X_4$ is a methylene group, an oxygen atom, or a sulfur atom.

The following are examples of the repeating unit represented by Formula (V-1) or (V-2).

Examples of the repeating unit represented by Formula (V-1) or (V-2) include the repeating units described in Paragraph [0100] of WO2018/193954A.

Repeating Unit for Lowering Mobility of Main Chains

The resin (A) preferably has, from the viewpoint of suppressing excessive diffusion of the generated acid or pattern collapse during development, a high glass transition temperature (Tg). Tg is preferably more than 90° C., more preferably more than 100° C., still more preferably more than 110° C., particularly preferably more than 125° C. Note that, from the viewpoint of having a high-dissolution rate in developers, Tg is preferably 400° C. or less, more preferably 350° C. or less.

Note that, in this Specification, the glass transition temperatures (Tg) of polymers such as the resin (A) (hereafter, "Tg's of repeating units") are calculated in the following manner. First, Tg's of homopolymers composed only of the repeating units included in such a polymer are calculated by the Bicerano method. Subsequently, the mass ratios (%) of the repeating units relative to all the repeating units in the polymer are calculated. Subsequently, the Fox equation (described in Materials Letters 62 (2008) 3152, for example) is used to calculate Tg's for the mass ratios and the Tg's are summed up to determine the Tg(° C.) of the polymer.

The Bicerano method is described in Prediction of polymer properties, Marcel Dekker Inc, New York (1993). The calculation of Tg by the Bicerano method can be performed using a software for estimating properties of polymers, MDL Polymer (MDL Information Systems, Inc.).

In order to increase the Tg of the resin (A)(preferably, making Tg be more than 90° C.), the mobility of the main chain of the resin (A) is preferably lowered. Examples of the method for lowering the mobility of the main chain of the resin (A) include the following methods (a) to (e): (a) introduction of a bulky substituent into the main chain; (b) introduction of a plurality of substituents into the main chain; (c) introduction of substituents inducing the interaction between resin (A) molecules, into regions near the main chains; (d) formation of the main chain having a ring structure; and (e) linking of a ring structure to the main chain.

Note that the resin (A) preferably has a repeating unit whose homopolymer has a Tg of 130° C. or more.

Note that the repeating unit species whose homopolymer has a Tg of 130° C. or more is not particularly limited and it is at least a repeating unit whose homopolymer has a Tg of 130° C. or more calculated by the Bicerano method. Note that the repeating units represented by Formula (A) to Formula (E) described later may, depending on the functional group species, belong to the repeating unit whose homopolymer has a Tg of 130° C. or more.

An example of specific means for achieving (a) above is a method of introducing, into the resin (A), a repeating unit represented by Formula (A).

(A)

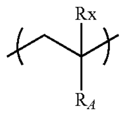

For Formula (A), $R_A$ represents a group including a polycyclic structure. $R_x$ represents a hydrogen atom, a methyl group, or an ethyl group. The group including a polycyclic structure is a group including a plurality of cyclic structures; the plurality of cyclic structures may be fused together or may not be fused together.

Specific examples of the repeating unit represented by Formula (A) include those described in Paragraphs [0107] to [0119] of WO2018/193954A.

An example of specific means for achieving (b) above is a method of introducing, into the resin (A), a repeating unit represented by Formula (B).

(B)

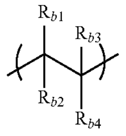

In Formula (B), $R_{b1}$ to $R_{b4}$ each independently represent a hydrogen atom or an organic group; at least two or more of $R_{b1}$ to $R_{b4}$ represent organic groups.

When at least one of the organic groups is a group whose cyclic structure is directly linked to the main chain in the repeating unit, the other organic group species are not particularly limited.

When none of the organic groups is a group whose cyclic structure is directly linked to the main chain in the repeating unit, at least two or more of the organic groups are substituents having three or more constituent atoms (except for hydrogen atoms).

Specific examples of the repeating unit represented by Formula (B) include those described in Paragraphs [0113] to [0115] of WO2018/193954A.

An example of specific means for achieving (c) above is a method of introducing, into the resin (A), a repeating unit represented by Formula (C).

(C)

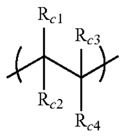

In Formula (C), $R_{c1}$ to $R_{c4}$ each independently represent a hydrogen atom or an organic group; at least one of $R_{c1}$ to $R_{c4}$ is a group including a hydrogen-bond-forming hydrogen atom positioned within three atoms from the carbon atom in the main chain. In particular, from the viewpoint of inducing the interaction between the main chains of resin (A) molecules, it preferably has a hydrogen-bond-forming hydrogen atom positioned within two atoms (closer to the main chain).

Specific examples of the repeating unit represented by Formula (C) include those described in Paragraphs [0119] to [0121] of WO2018/193954A.

An example of specific means for achieving (d) above is a method of introducing, into the resin (A), a repeating unit represented by Formula (D).

(D)

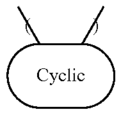

In Formula (D), "Cyclic" denotes a group having a ring structure and forming the main chain. The number of atoms constituting the ring is not particularly limited.

Specific examples of the repeating unit represented by Formula (D) include those described in Paragraphs [0126] to [0127] of WO2018/193954A.

An example of specific means for achieving (e) above is a method of introducing, into the resin (A), a repeating unit represented by Formula (E).

(E)

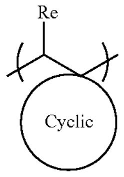

In Formula (E), Re each independently represent a hydrogen atom or an organic group. Examples of the organic group include alkyl groups, cycloalkyl groups, aryl groups, aralkyl groups, and alkenyl groups that may have substituents.

"Cyclic" is a cyclic group including a carbon atom of the main chain. The number of atoms included in the cyclic group is not particularly limited.

Specific examples of the repeating unit represented by Formula (E) include those described in Paragraphs [0131] to [0133] of WO2018/193954A.

Repeating unit having at least one group species selected from the group consisting of lactone group, sultone group, carbonate group, hydroxy group, cyano group, and alkali-soluble group The resin (A) may have a repeating unit having at least one group species selected from the group consisting of a lactone group, a sultone group, a carbonate group, a hydroxy group, a cyano group, and an alkali-soluble group.

In the resin (A), the repeating unit having a lactone group, a sultone group, or a carbonate group may be the repeating unit having been described in <Repeating unit having lactone group, sultone group, or carbonate group>. Preferred contents are also the same as those having been described in <Repeating unit having lactone group, sultone group, or carbonate group>.

The resin (A) may have a repeating unit having a hydroxy group or a cyano group. This results in improvement in adhesiveness to the substrate and affinity for the developer.

The repeating unit having a hydroxy group or a cyano group is preferably a repeating unit having an alicyclic hydrocarbon structure substituted with a hydroxy group or a cyano group The repeating unit having a hydroxy group or a cyano group preferably does not have an acid-decomposable group. Examples of the repeating unit having a hydroxy group or a cyano group include those described in Paragraphs [0081] to [0084] of JP2014-098921A.

The resin (A) may have a repeating unit having an alkali-soluble group.

The alkali-soluble group may be a carboxyl group, a sulfonamide group, a sulfonylimide group, a bissulfonylimide group, or an aliphatic alcohol group substituted, at the α position, with an electron-withdrawing group (for example, a hexafluoroisopropanol group), and is preferably a carboxyl group. When the resin (A) includes the repeating unit having an alkali-soluble group, increased resolution is provided in the contact hole application. Examples of the repeating unit having an alkali-soluble group include those described in Paragraphs [0085] and [0086] of JP2014-098921A.

Repeating Unit Having Alicyclic Hydrocarbon Structure and not Exhibiting Acid Decomposability The resin (A) may have a repeating unit having an alicyclic hydrocarbon structure and not exhibiting acid decomposability. This results in, during liquid immersion exposure, a reduction in leaching of, from the resist film to the immersion liquid, low-molecular-weight components. Examples of the repeating unit having an alicyclic hydrocarbon structure and not exhibiting acid decomposability include repeating units derived from 1-adamantyl (meth)acrylate, diadamantyl (meth)acrylate, tricyclodecanyl (meth)acrylate, or cyclohexyl (meth)acrylate.

Repeating Unit not Having Hydroxy Group or Cyano Group and Represented by Formula (III)

The resin (A) may have a repeating unit not having a hydroxy group or a cyano group and represented by Formula (III).

(III)

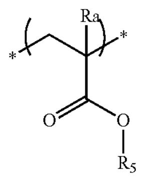

In Formula (III), $R_5$ represents a hydrocarbon group having at least one ring structure and not having a hydroxy group or a cyano group.

Ra represents a hydrogen atom, an alkyl group, or a $—CH_2—O—Ra_2$ group. In the formula, $Ra_2$ represents a hydrogen atom, an alkyl group, or an acyl group.

Examples of the repeating unit not having a hydroxy group or a cyano group and represented by Formula (III) include those described in Paragraphs [0087] to [0094] of JP2014-098921A.

Other Repeating Unit

Furthermore, the resin (A) may have another repeating unit other than the above-described repeating units.

For example, the resin (A) may have a repeating unit selected from the group consisting of a repeating unit having an oxathiane ring group, a repeating unit having an oxazolone ring group, a repeating unit having a dioxane ring group, and a repeating unit having a hydantoin ring group.

The following are specific examples of the other repeating unit other than the above-described repeating units.

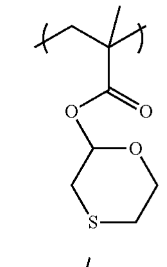
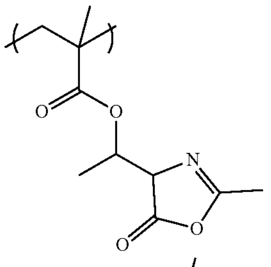
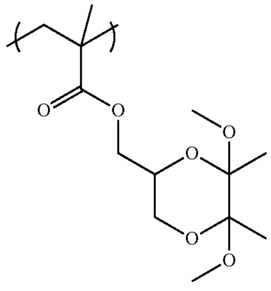
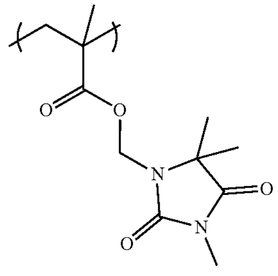

The resin (A) may have, in addition to such repeating structure units, for the purpose of adjusting, for example, dry etching resistance, standard developer suitability, substrate adhesiveness, resist profile, resolution, heat resistance, and sensitivity, various repeating structure units.

For the resin (A), particularly when the composition is used as an ArF actinic ray-sensitive or radiation-sensitive resin composition, all the repeating units are preferably constituted by repeating units derived from compounds having ethylenically unsaturated bonds. In particular, all the repeating units are also preferably constituted by (meth) acrylate-based repeating units. In the case in which all the repeating units are constituted by (meth)acrylate-based repeating units, all the repeating units may be methacrylate-based repeating units, all the repeating units may be acrylate-based repeating units, or all the repeating units may be methacrylate-based repeating units and acrylate-based repeating units; acrylate-based repeating units are preferably 50 mol % or less of all the repeating units.

The resin (A) can be synthesized by standard procedures (for example, radical polymerization).

The resin (A) has a weight-average molecular weight (as a polystyrene equivalent value determined by GPC method) of preferably 30,000 or less, more preferably 1,000 to 30,000, still more preferably 3,000 to 30,000, particularly preferably 5,000 to 15,000.

The resin (A) preferably has a dispersity (molecular weight distribution) of 1 to 5, more preferably 1 to 3, still more preferably 1.2 to 3.0, particularly preferably 1.2 to 2.0. As the dispersity lowers, the resolution becomes higher, the resist profile becomes better, the sidewalls of the resist pattern become smoother, and the roughness performance becomes higher.

In the actinic ray-sensitive or radiation-sensitive resin composition, the resin (A) content relative to the total solid content of the actinic ray-sensitive or radiation-sensitive resin composition is preferably 40.0 to 99.9 mass %, more preferably 60.0 to 90.0 mass %.

Such resins (A) may be used alone or in combination of two or more thereof.

Compound (B) that Generates Acid in Response to Irradiation with Actinic Ray or Radiation The actinic ray-sensitive or radiation-sensitive resin composition may include a compound (B) that generates acid in response to irradiation with an actinic ray or radiation (also referred to as "compound (B)" or "photoacid generator (B)").

In the above-described step (3), in addition to the onium salt (C) and the resin (A), the photoacid generator (B) may be mixed.

The photoacid generator (B) may have the form of a low-molecular-weight compound, or the form of being incorporated into a portion of a polymer (for example, the resin (A) described later). Alternatively, the form of a low-molecular-weight compound and the form of being incorporated into a portion of a polymer (for example, the resin (A) described later) may be used in combination.

When the photoacid generator (B) has the form of a low-molecular-weight compound, the photoacid generator preferably has a molecular weight of 3000 or less, more preferably 2000 or less, still more preferably 1000 or less. The lower limit is not particularly limited, but is preferably 100 or more.

When the photoacid generator (B) has the form of being incorporated into a portion of a polymer, it may be incorporated into a portion of the resin (A) or may be incorporated into a resin different from the resin (A).

In this Specification, the photoacid generator (B) preferably has the form of a low-molecular-weight compound.

The photoacid generator (B) may be, for example, a compound represented by "$M^+X^-$" (onium salt), and is preferably a compound that generates an organic acid by exposure.

Examples of the organic acid include sulfonic acids (such as aliphatic sulfonic acids, aromatic sulfonic acids, and camphorsulfonic acid), carboxylic acids (such as aliphatic carboxylic acids, aromatic carboxylic acids, and aralkyl carboxylic acids), carbonylsulfonylimidic acid, bis(alkylsulfonyl)imidic acids, and tris(alkylsulfonyl)methide acids.

In the compound represented by "$M^+X^-$", $M^+$ represents an organic cation.

The organic cation is the same as, in terms of descriptions, specific examples, and preferred examples, the above-described organic cation of the onium salt (C).

In the compound represented by "$M^+X^-$", $X^-$ represents an organic anion.

The organic anion is not particularly limited, but may be a mono-, di-, or higher valent organic anion.

The organic anion is preferably an anion that has a very low capability of causing a nucleophilic reaction, more preferably a non-nucleophilic anion.

Examples of the non-nucleophilic anion include sulfonate anions (such as aliphatic sulfonate anions, aromatic sulfonate anions, and a camphorsulfonate anion), carboxylate anions (such as aliphatic carboxylate anions, aromatic carboxylate anions, and aralkyl carboxylate anions), a sulfonylimide anion, bis(alkylsulfonyl)imide anions, and tris(alkylsulfonyl)methide anions.

In such an aliphatic sulfonate anion or aliphatic carboxylate anion, the aliphatic moiety may be a linear or branched alkyl group or a cycloalkyl group, and is preferably a linear or branched alkyl group having 1 to 30 carbon atoms, or a cycloalkyl group having 3 to 30 carbon atoms.

The alkyl group may be, for example, a fluoroalkyl group (may have a substituent other than a fluorine atom or may be a perfluoroalkyl group).

In such an aromatic sulfonate anion or aromatic carboxylate anion, the aryl group is preferably an aryl group having 6 to 14 carbon atoms, for example, a phenyl group, a tolyl group, or a naphthyl group.

The above-described alkyl group, cycloalkyl group, and aryl group may have a substituent. The substituent is not particularly limited; examples include a nitro group, halogen atoms such as a fluorine atom and a chlorine atom, a carboxyl group, a hydroxy group, an amino group, a cyano group, alkoxy groups (preferably having 1 to 15 carbon atoms), alkyl groups (preferably having 1 to 10 carbon atoms), cycloalkyl groups (preferably having 3 to 15 carbon atoms), aryl groups (preferably having 6 to 14 carbon atoms), alkoxycarbonyl groups (preferably having 2 to 7 carbon atoms), acyl groups (preferably having 2 to 12 carbon atoms), alkoxycarbonyloxy groups (preferably having 2 to 7 carbon atoms), alkylthio groups (preferably having 1 to 15 carbon atoms), alkylsulfonyl groups (preferably having 1 to 15 carbon atoms), alkyliminosulfonyl groups (preferably having 1 to 15 carbon atoms), and aryloxysulfonyl groups (preferably having 6 to 20 carbon atoms).

In such an aralkyl carboxylate anion, the aralkyl group is preferably an aralkyl group having 7 to 14 carbon atoms.

Examples of the aralkyl group having 7 to 14 carbon atoms include a benzyl group, a phenethyl group, a naphthylmethyl group, a naphthylethyl group, and a naphthylbutyl group.

The sulfonylimide anion may be, for example, a saccharin anion.

In such a bis(alkylsulfonyl)imide anion or a tris(alkylsulfonyl)methide anion, the alkyl groups are preferably an alkyl group having 1 to 5 carbon atoms. In the alkyl group, a substituent may be a halogen atom, an alkyl group substituted with a halogen atom, an alkoxy group, an alkylthio group, an alkyloxysulfonyl group, an aryloxysulfonyl group, or a cycloalkylaryloxysulfonyl group, and is preferably a fluorine atom or an alkyl group substituted with a fluorine atom.

In the bis(alkylsulfonyl)imide anion, the alkyl groups may be linked together to form a ring structure. This results in an increase in the acid strength.

Other examples of the non-nucleophilic anion include phosphorus fluoride (for example, $PF_6^-$), boron fluoride (for example, $BF_4^-$), and antimony fluoride (for example, $SbF_6^-$).

The non-nucleophilic anion is preferably an aliphatic sulfonate anion in which at least the α position of sulfonic acid is substituted with a fluorine atom, an aromatic sulfonate anion substituted with a fluorine atom or a group having a fluorine atom, a bis(alkylsulfonyl)imide anion in which the alkyl groups are substituted with fluorine atoms, or a tris(alkylsulfonyl)methide anion in which the alkyl groups are substituted with fluorine atoms. In particular, the anion is more preferably a perfluoroaliphatic sulfonate anion (preferably having 4 to 8 carbon atoms) or a benzenesulfonate anion having a fluorine atom, still more preferably a nonafluorobutanesulfonate anion, a perfluorooctanesulfonate anion, a pentafluorobenzenesulfonate anion, or a 3,5-bis(trifluoromethyl)benzenesulfonate anion.

The non-nucleophilic anion is also preferably an anion represented by the following Formula (AN1).

(AN1)

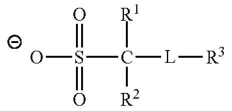

In Formula (AN1), Rt and $R^2$ each independently represent a hydrogen atom or a substituent.

The substituent is not particularly limited, but is preferably a group that is not electron-withdrawing groups. Examples of the group that is not electron-withdrawing groups include hydrocarbon groups, a hydroxy group, oxyhydrocarbon groups, oxycarbonylhydrocarbon groups, an amino group, hydrocarbon-substituted amino groups, and hydrocarbon-substituted amide groups.

Such groups that are not electron-withdrawing groups are each independently preferably —R', —OH, —OR', —OCOR', —$NH_2$, —$NR'_2$, —NHR', or —NHCOR'. R' are monovalent hydrocarbon groups.

Examples of the monovalent hydrocarbon groups represented by R' above include monovalent linear or branched hydrocarbon groups such as alkyl groups such as a methyl group, an ethyl group, a propyl group, and a butyl group; alkenyl groups such as an ethenyl group, a propenyl group, and a butenyl group; and alkynyl groups such as an ethynyl group, a propynyl group, and a butynyl group; monovalent alicyclic hydrocarbon groups such as cycloalkyl groups such as a cyclopropyl group, a cyclobutyl group, a cyclopentyl group, a cyclohexyl group, a norbornyl group, and an adamantyl group; and cycloalkenyl groups such as a cyclopropenyl group, a cyclobutenyl group, a cyclopentenyl group, and a norbornenyl group; and monovalent aromatic hydrocarbon groups such as aryl groups such as a phenyl group, a tolyl group, a xylyl group, a mesityl group, a naphthyl group, a methylnaphthyl group, an anthryl group, and methylanthryl group; and aralkyl groups such as a benzyl group, a phenethyl group, a phenylpropyl group, a naphthylmethyl group, and an anthrylmethyl group.

In particular, $R^1$ and $R^2$ are each independently preferably a hydrocarbon group (preferably a cycloalkyl group) or a hydrogen atom.

L represents a divalent linking group.

When there are a plurality of L's, L's may be the same or different.

The divalent linking group may be, for example, —O—CO—O—, —COO—, —CONH—, —CO—, —O—, —S—, —SO—, —$SO_2$—, an alkylene group (preferably having 1 to 6 carbon atoms), a cycloalkylene group (preferably having 3 to 15 carbon atoms), an alkenylene group (preferably having 2 to 6 carbon atoms), or a divalent linking group provided by combining a plurality of the foregoing. In particular, the divalent linking group is preferably —O—CO—O—, —COO—, —CONH—, —CO—, —O—, —$SO_2$—, —O—CO—O-alkylene group-, —COO-alkylene group-, or —CONH-alkylene group-, more preferably —O—CO—O—, —O—CO—O-alkylene group-, —COO—, —CONH—, —$SO_2$—, or —COO-alkylene group-.

Lis preferably, for example, a group represented by the following Formula (AN1-1).

$$*^a\text{-}(CR^{2a}{}_2)_X\text{-}Q\text{-}(CR^{2b}{}_2)_Y\text{-}*^b \qquad \text{(AN1-1)}$$

In Formula (AN1-1), $*^3$ represents the bonding site to $R^3$ in Formula (AN1).

$*^b$ represents the bonding site to —$C(R^1)(R^2)$— in Formula (AN1).

X and Y each independently represent an integer of 0 to 10, and is preferably an integer of 0 to 3.

$R^{2a}$ and $R^{2b}$ each independently represent a hydrogen atom or a substituent.

When there are a plurality of $R^{2a}$'s and a plurality of $R^{2b}$'s, the plurality of $R^{2a}$'s and the plurality of $R^{2b}$'s may be individually the same or different.

Note that, when Y is 1 or more, in Formula (AN1), in $CR^{2b}{}_2$ directly bonded to —$C(R^1)(R^2)$—, $R^{2b}$ is not a fluorine atom.

Q represents $*^A$—O—CO—O—$*^B$, *A-CO—$*^B$, $*^A$—CO—O—$*^B$, $*^A$—O—CO—$*^B$, $*^A$—O—$*^B$, $*^A$—S—$*^B$, or $*^A$—$SO_2$—$*^B$.

Note that, when X+Y in Formula (AN1-1) is 1 or more, and $R^{2a}$ and $R^{2b}$ in Formula (AN1-1) are all hydrogen atoms, Q represents $*^A$—O—CO—O—$*^B$, $*^A$—CO—$*^B$, $*^A$—O—CO—$*^B$, $*^A$—O— $*^B$, $*^A$—S—$*^B$, or $*^A$—$SO_2$—$*^B$.

$*^A$ represent a bonding site on the $R^3$ side in Formula (AN1). $*^B$ represent a bonding site on the —$SO_3^-$ side in Formula (AN1).

In Formula (AN1), $R^3$ represents an organic group.

The organic group is not particularly limited as long as it has 1 or more carbon atoms, and may be a linear group (for example, a linear alkyl group), a branched group (for example, a branched alkyl group such as a t-butyl group), or a cyclic group. The organic group may or may not have a substituent. The organic group may or may not have a heteroatom (such as an oxygen atom, a sulfur atom, and/or a nitrogen atom).

In particular, $R^3$ is preferably an organic group having a ring structure. The ring structure may be monocyclic or polycyclic, and may have a substituent. In the organic group including a ring structure, the ring is preferably directly bonded to L in Formula (AN1).

The organic group having a ring structure, for example, may or may not have a heteroatom (such as an oxygen atom, a sulfur atom, and/or a nitrogen atom). The heteroatom may substitute one or more carbon atoms forming the ring structure.

The organic group having a ring structure is preferably, for example, a hydrocarbon group having a ring structure, a lactone ring group, or a sultone ring group. In particular, the organic group having a ring structure is preferably a hydrocarbon group having a ring structure.

The hydrocarbon group having a ring structure is preferably a monocyclic or polycyclic cycloalkyl group. Such groups may have a substituent.

The cycloalkyl group may be monocyclic (such as a cyclohexyl group) or polycyclic (such as an adamantyl group), and preferably has 5 to 12 carbon atoms.

The lactone group and the sultone group are preferably, for example, a group in which, in any one of the above-described structures represented by Formula (LC1-1) to (LC1-21) and structures represented by Formulas (SL1-1) to (SL1-3), from a ring-member atom forming the lactone structure or the sultone structure, a single hydrogen atom has been removed.

The non-nucleophilic anion may be a benzenesulfonate anion, and is preferably a benzenesulfonate anion substituted with a branched alkyl group or a cycloalkyl group.

The non-nucleophilic anion is also preferably an anion represented by the following Formula (AN2).

(AN2)

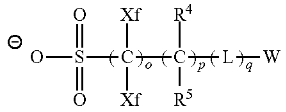

In Formula (AN2), o represents an integer of 1 to 3. p represents an integer of 0 to 10. q represents an integer of 0 to 10.

Xf's represent a hydrogen atom, a fluorine atom, an alkyl group substituted with at least one fluorine atom, or an organic group not having fluorine atoms. The alkyl group preferably has 1 to 10 carbon atoms, more preferably 1 to 4 carbon atoms. The alkyl group substituted with at least one fluorine atom is preferably a perfluoroalkyl group.

Xf's are preferably a fluorine atom or a perfluoroalkyl group having 1 to 4 carbon atoms, more preferably a fluorine atom or $CF_3$; still more preferably, both Xf's are fluorine atoms.

$R^4$ and $R^5$ each independently represent a hydrogen atom, a fluorine atom, an alkyl group, or an alkyl group substituted with at least one fluorine atom. When there are a plurality of $R^4$'s and $R^5$'s, $R^4$'s and $R^5$'s may be individually the same or different.

In $R^4$ and $R^5$, the alkyl group preferably has 1 to 4 carbon atoms. The alkyl group may have a substituent. $R^4$ and $R^5$ are preferably a hydrogen atom.

L represents a divalent linking group. L has the same definition as Lin Formula (AN1).

W represents an organic group including a ring structure and, in particular, preferably a cyclic organic group.

The cyclic organic group may be, for example, an alicyclic group, an aryl group, or a heterocyclic group.

The alicyclic group may be monocyclic or polycyclic. Examples of the monocyclic alicyclic group include monocyclic cycloalkyl groups such as a cyclopentyl group, a cyclohexyl group, and a cyclooctyl group. Examples of the polycyclic alicyclic group include polycyclic cycloalkyl groups such as a norbornyl group, a tricyclodecanyl group, a tetracyclodecanyl group, a tetracyclododecanyl group, and an adamantyl group. In particular, preferred are alicyclic groups having a bulky structure having 7 or more carbon atoms such as a norbornyl group, a tricyclodecanyl group, a tetracyclodecanyl group, a tetracyclododecanyl group, and an adamantyl group.

The aryl group may be monocyclic or polycyclic. Examples of the aryl group include a phenyl group, a naphthyl group, a phenanthryl group, and an anthryl group.

The heterocyclic group may be monocyclic or polycyclic. In particular, in the case of a polycyclic heterocyclic group, diffusion of acid can be further suppressed. The heterocyclic group may have aromaticity or may not have aromaticity. Examples of the heterocycle having aromaticity include a furan ring, a thiophene ring, a benzofuran ring, a benzothiophene ring, a dibenzofuran ring, a dibenzothiophene ring, and a pyridine ring. Examples of the heterocycle not having aromaticity include a tetrahydropyran ring, a lactone ring, a sultone ring, and a decahydroisoquinoline ring. In the heterocyclic group, the heterocycle is preferably a furan ring, a thiophene ring, a pyridine ring, or a decahydroisoquinoline ring.

The cyclic organic group may have a substituent. The substituent may be, for example, an alkyl group (linear or branched, preferably having 1 to 12 carbon atoms), a cycloalkyl group (having a monocycle, a polycycle, or a spiro ring, preferably having 3 to 20 carbon atoms), an aryl group (preferably having 6 to 14 carbon atoms), a hydroxy group, an alkoxy group, an ester group, an amide group, a urethane group, a ureido group, a thioether group, a sulfonamide group, or a sulfonic acid ester group. Note that a carbon forming the cyclic organic group (carbon contributing to formation of the ring) may be a carbonyl carbon.

The anion represented by Formula (AN2) is preferably $SO_3^-$—$CF_2$—$CH_2$—OCO-$(L)_{q'}$-W, $SO_3^-$—$CF_2$—CHF—$CH_2$—OCO-$(L)_{q'}$-W, $SO_3^-$—$CF_2$—COO-$(L)_{q'}$-W, $SO_3^-$—$CF_2$—$CF_2$—$CH_2$—$CH_2$-$(L)_q$-W, or $SO_3^-$—$CF_2$—CH$(CF_3)$—OCO-$(L)_{q'}$-W, where L, q, and W are the same as in Formula (AN2), and q' represent an integer of 0 to 10.

The non-nucleophilic anion is also preferably an aromatic sulfonate anion represented by the following Formula (AN3).

(AN3)

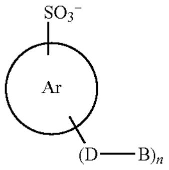

In Formula (AN3), Ar represents an aryl group (such as a phenyl group), and may further have a substituent other than the sulfonate anion and the -(D-B) group. Examples of the substituent that Ar may further have include a fluorine atom and a hydroxy group.

n represents an integer of 0 or more. n is preferably 1 to 4, more preferably 2 to 3, still more preferably 3.

D represents a single bond or a divalent linking group. The divalent linking group may be an ether group, a thioether group, a carbonyl group, a sulfoxide group, a sulfo group, a sulfonic acid ester group, an ester group, or a group of a combination of two or more of the foregoing.

B represents a hydrocarbon group.

B is preferably an aliphatic hydrocarbon group, more preferably an isopropyl group, a cyclohexyl group, or an aryl group that may further have a substituent (such as a tricyclohexylphenyl group).

The non-nucleophilic anion is also preferably a disulfonamide anion.

The disulfonamide anion is, for example, an anion represented by N—$(SO_2$—$R^q)_2$.

$R^q$'s represent an alkyl group that may have a substituent, and are preferably a fluoroalkyl group, more preferably a perfluoroalkyl group. Two $R^q$'s may be linked together to form a ring. The group formed by linking together two $R^q$'s is preferably an alkylene group that may have a substituent, preferably a fluoroalkylene group, more preferably a perfluoroalkylene group. The alkylene group preferably has 2 to 4 carbon atoms.

Other examples of the non-nucleophilic anion include anions represented by the following Formulas (d1-1) to (d1-4).

(d1-1)

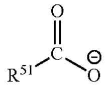

(d1-2)

$Z^{2c}$—$SO_3^{\ominus}$ (d1-3)

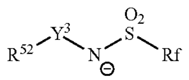

(d1-4)

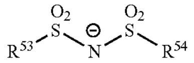

In Formula (d1-1), $R^{51}$ represents a hydrocarbon group that may have a substituent (such as a hydroxy group) (for example, an aryl group such as a phenyl group).

In Formula (d1-2), $Z^{2c}$ represents a hydrocarbon group that has 1 to 30 carbon atoms and that may have a substituent (note that the carbon atom adjacent to S is not substituted with a fluorine atom).

In $Z^{2c}$, the hydrocarbon group may be linear or branched, and may have a ring structure. In the hydrocarbon group, a carbon atom (preferably, in a case where the hydrocarbon group has a ring structure, a carbon atom serving as a ring-member atom) may be a carbonyl carbon (—CO—). The hydrocarbon group may be, for example, a group that has a norbornyl group that may have a substituent. A carbon atom forming the norbornyl group may be a carbonyl carbon.

In Formula (d1-2), "$Z^{2c}$—$SO_3^-$" is preferably different from the anions represented by Formulas (AN1) to (AN3) above. For example, $Z^{2c}$ is preferably not aryl groups. For example, in $Z^{2c}$, the atoms at the α position and the β position relative to —$SO_3^-$ are preferably atoms other than carbon atoms having, as a substituent, a fluorine atom. For example, in $Z^{2c}$, the atom at the α position and/or the atom at the β position relative to —$SO_3^-$ is preferably a ring-member atom in a ring group.

In Formula (d1-3), $R^{52}$ represents an organic group (preferably a hydrocarbon group having a fluorine atom), $Y^3$ represents a linear, branched, or cyclic alkylene group, an arylene group, or a carbonyl group, and Rf represents a hydrocarbon group.

In Formula (d1-4), $R^{53}$ and $R^{54}$ each independently represent an organic group (preferably a hydrocarbon group having a fluorine atom). $R^{53}$ and $R^{54}$ may be linked together to form a ring.

Such organic anions may be used alone or in combination of two or more thereof.

The photoacid generator is also preferably at least one selected from the group consisting of compounds (I) to (II).

Compound (I)

The compound (I) is a compound having one or more of the following moiety X and one or more of the following moiety Y and is a compound that is irradiated with an actinic ray or radiation to generate an acid including the following first acidic moiety derived from the following moiety X and the following second acidic moiety derived from the following moiety Y.

Moiety X: a moiety that is constituted by an anionic moiety $A_1^-$ and a cationic moiety $M_1^+$ and is irradiated with an actinic ray or radiation to form the first acidic moiety represented by $HA_1$ Moiety Y: a moiety that is constituted by an anionic moiety $A_2^-$ and a cationic moiety $M_2^+$ and is irradiated with an actinic ray or radiation to form the second acidic moiety represented by $HA_2$ The compound (I) satisfies the following condition I.

Condition I: a compound PI in which, in the compound (I), the cationic moiety $M_1^+$ of the moiety X and the cationic moiety $M_2^+$ of the moiety Y are replaced by $H^+$ has an acid dissociation constant a1 derived from an acidic moiety represented by $HA_1$ in which the cationic moiety $M_1^+$ of the moiety X is replaced by $H^+$ and an acid dissociation constant a2 derived from an acidic moiety represented by $HA_2$ in which the cationic moiety $M_2^+$ of the moiety Y is replaced by $H^+$, and the acid dissociation constant a2 is larger than the acid dissociation constant a1.

Hereinafter, the condition I will be more specifically described.

When the compound (I) is, for example, a compound that generates an acid having a single first acidic moiety derived from the moiety X and a single second acidic moiety derived from the moiety Y, the compound PI corresponds to "compound having $HA_1$ and $HA_2$".

The acid dissociation constant a1 and the acid dissociation constant a2 of the compound PI are more specifically as follows: in determination of the acid dissociation constants of the compound PI, the pKa determined when the compound PI is turned into "compound having $A_1^-$ and $HA_2$" is the acid dissociation constant a1 and the pKa determined when the "compound having $A_1^-$ and $HA_2$" is turned into "compound having $A_1^-$ and $A_2$" is the acid dissociation constant a2.

When the compound (I) is, for example, a compound that generates an acid having two first acidic moieties derived from the moiety X and a single second acidic moiety derived from the moiety Y, the compound PI corresponds to "compound having two $HA_1$ and a single $HA_2$".

In determination of the acid dissociation constants of the compound PI, the acid dissociation constant determined when the compound PI is turned into "compound having a single $A_1^-$, a single $HA_1$, and a single $HA_2$" and the acid dissociation constant determined when the "compound having a single $A_1^-$, a single $HA_1^-$, and a single $HA_2$" is turned into "compound having two $A_1^-$ and a single $HA_2$" correspond to the above-described acid dissociation constant a1. The acid dissociation constant determined when the "compound having two $A_1^-$ and a single $HA_2$" is turned into "compound having two $A_1^-$ and $A_2^-$" corresponds to the acid dissociation constant a2. Thus, in the case of the compound PI having a plurality of acid dissociation constants derived from acidic moieties represented by $HA_1$ in which the cationic moiety $M_1^+$ in the moiety X is replaced by $H^+$, the value of the acid dissociation constant a2 is larger than the maximum value of the plurality of acid dissociation constants a1. Note that, when the acid dissociation constant determined when the compound PI is turned into "compound having a single $A_1^-$, a single $HA_1$, and a single $HA_2$" is defined as aa and the acid dissociation constant determined when the "compound having a single $A_1^-$, a single $HA_1$, and a single $HA_2$" is turned into "compound having two $A_1^-$ and a single $HA_2$" is defined as ab, the relation of aa and ab satisfies aa<ab.

The acid dissociation constant a1 and the acid dissociation constant a2 can be determined by the above-described method of measuring an acid dissociation constant.

The compound PI corresponds to an acid generated upon irradiation of the compound (I) with an actinic ray or radiation.

When the compound (1) has two or more moieties X, the moieties X may be the same or different. The two or more $A_1^-$ and the two or more $M_1^-$ may be individually the same or different.

In the compound (I), the $A_1^-$ and the $A_2^-$, and the $M_1^+$ and the $M_2^+$ may be individually the same or different; but, the $A_1^-$ and the $A_2^-$ are preferably different.

In the compound PI, the difference (absolute value) between the acid dissociation constant a1 (in the case of a plurality of acid dissociation constants a1, the maximum value thereof) and the acid dissociation constant a2 is preferably 0.1 or more, more preferably 0.5 or more, still more preferably 1.0 or more. Note that the upper limit value of the difference (absolute value) between the acid dissociation constant a1 (in the case of a plurality of acid dissociation constants a1, the maximum value thereof) and the acid dissociation constant a2 is not particularly limited, but is, for example, 16 or less.

In the compound PI, the acid dissociation constant a2 is preferably 20 or less, more preferably 15 or less. Note that the lower limit value of the acid dissociation constant a2 is preferably −4.0 or more.

In the compound PI, the acid dissociation constant a1 is preferably 2.0 or less, more preferably 0 or less. Note that the lower limit value of the acid dissociation constant a1 is preferably −20.0 or more.

The anionic moiety $A_1^-$ and the anionic moiety $A_2^-$ are moieties including a negatively charged atom or atomic group and are, for example, moieties selected from the group consisting of Formulas (AA-1) to (AA-3) and Formulas (BB-1) to (BB-6) below.

The anionic moiety $A_1^-$ is preferably one that forms an acidic moiety having a smaller acid dissociation constant, in particular, more preferably any one of Formulas (AA-1) to (AA-3), still more preferably any one of Formulas (AA-1) and (AA-3).

The anionic moiety $A_2^-$ is preferably one that forms an acidic moiety having a larger acid dissociation constant than the anionic moiety $A_1^-$, more preferably any one of Formulas (BB-1) to (BB-6), still more preferably any one of Formulas (BB-1) and (BB-4).

Note that, in Formulas (AA-1) to (AA-3) and Formulas (BB-1) to (BB-6) below, * represent a bonding site.

In Formula (AA-2), $R^A$ represent a monovalent organic group. The monovalent organic groups represented by $R_A$ are not particularly limited, but may be, for example, a cyano group, a trifluoromethyl group, or a methanesulfonyl group.

AA-1

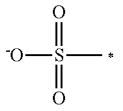

AA-2

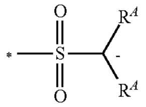

AA-3

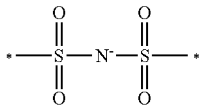

BB-1

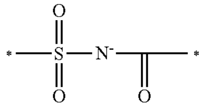

BB-2

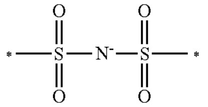

BB-3

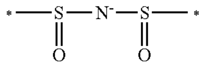

BB-4

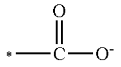

BB-5

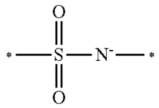

BB-6

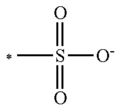

The cationic moiety $M_1^-$ and the cationic moiety $M_2^+$ are moieties including a positively charged atom or atomic group and are, for example, singly charged organic cations. Note that such an organic cation may be, for example, the above-described organic cation represented by $M^+$.

The compound (I) is not particularly limited in terms of specific structures; examples include compounds represented by Formula (Ia-1) to Formula (Ia-5) described later.

Compound Represented by Formula (Ia-1)

Hereinafter, first, the compound represented by Formula (Ia-1) will be described.

$$M_{11}^+A_{11}^--L_1-A_{12}^-M_{12}^+ \quad \text{(Ia-1)}$$

The compound represented by Formula (Ia-1) is irradiated with an actinic ray or radiation to generate an acid represented by $HA_{11}$-$L_1$-$A_{12}H$.

In Formula (Ia-1), $M_{11}^+$ and $M_{12}^+$ each independently represent an organic cation.

$A_{11}^-$ and $A_{12}^-$ each independently represent a monovalent anionic functional group.

$L_1$ represents a divalent linking group.

$M_{11}^+$ and $M_{12}^+$ may be the same or different.

$A_{11}^-$ and $A_{12}^-$ may be the same or different, but are preferably different from each other.

Note that, in a compound PIa ($HA_{11}$-$L_1$-$A_{12}H$) in which, in Formula (Ia-1) above, the cations represented by $M_{11}^+$ and $M_{12}^+$ are replaced by $H^+$, the acid dissociation constant a2 derived from the acidic moiety represented by $A_{12}H$ is larger than the acid dissociation constant a1 derived from the acidic moiety represented by $HA_{11}$. Note that preferred values of the acid dissociation constant a1 and the acid dissociation constant a2 are the same as those described above. The compound PIa is the same as the acid generated from the compound represented by Formula (Ia-1) in response to irradiation with an actinic ray or radiation.

At least one of $M_{11}^+$, $M_{12}^+$, $A_{11}^+$, $A_{12}^+$, or $L_1$ may have, as a substituent, an acid-decomposable group.

In Formula (Ia-1), the organic cations represented by $M_1^+$ and $M_2^+$ are the same as those described above.

The monovalent anionic functional group represented by $A_{11}^-$ means a monovalent group including the above-described anionic moiety $A_1^-$. The monovalent anionic functional group represented by $A_{12}^-$ means a monovalent group including the above-described anionic moiety $A_2^-$.

The monovalent anionic functional groups represented by $A_{11}^-$ and $A_{12}^-$ are preferably monovalent anionic functional groups including the anionic moiety of any one of Formulas (AA-1) to (AA-3) and Formulas (BB-1) to (BB-6) above, more preferably monovalent anionic functional groups selected from the group consisting of Formulas (AX-1) to (AX-3) and Formulas (BX-1) to (BX-7). In particular, the monovalent anionic functional group represented by $A_{11}^-$ is preferably the monovalent anionic functional group represented by any one of Formulas (AX-1) to (AX-3). In particular, the monovalent anionic functional group represented by $A_{12}^-$ is preferably the monovalent anionic functional group represented by any one of Formulas (BX-1) to (BX-7), more preferably the monovalent anionic functional group represented by any one of Formulas (BX-1) to (BX-6).

AX-1

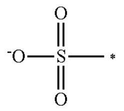

AX-2

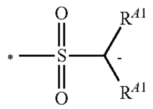

AX-3

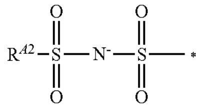

BX-1

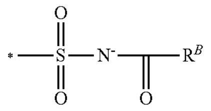

BX-2

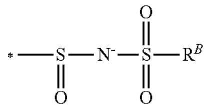

BX-3

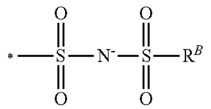

-continued

BX-4

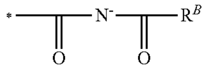

BX-5

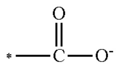

BX-6

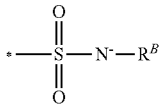

BX-7

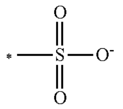

In Formula (AX-1) to (AX-3), $R^{A1}$ and $R^{A2}$ each independently represent a monovalent organic group. * represent a bonding site.

The monovalent organic groups represented by $R^{A1}$ are not particularly limited, but may be, for example, a cyano group, a trifluoromethyl group, or a methanesulfonyl group.

The monovalent organic group represented by $R^{A2}$ is preferably a linear, branched, or cyclic alkyl group or an aryl group.

The number of carbon atoms of the alkyl group is preferably 1 to 15, more preferably 1 to 10, still more preferably 1 to 6.

The alkyl group may have a substituent. The substituent is preferably a fluorine atom or a cyano group, more preferably a fluorine atom. When the alkyl group has, as a substituent, a fluorine atom, it may be a perfluoroalkyl group.

The aryl group is preferably a phenyl group or a naphthyl group, more preferably a phenyl group.

The aryl group may have a substituent. The substituent is preferably a fluorine atom, an iodine atom, a perfluoroalkyl group (for example, preferably having 1 to 10 carbon atoms, more preferably 1 to 6 carbon atoms), or a cyano group, more preferably a fluorine atom, an iodine atom, or a perfluoroalkyl group.

In Formulas (BX-1) to (BX-4) and Formula (BX-6), $R^B$ represent a monovalent organic group. * represent a bonding site.

The monovalent organic groups represented by $R^B$ are preferably a linear, branched, or cyclic alkyl group or an aryl group.

The number of carbon atoms of the alkyl group is preferably 1 to 15, more preferably 1 to 10, still more preferably 1 to 6.

The alkyl group may have a substituent. The substituent is not particularly limited, but the substituent is preferably a fluorine atom or a cyano group, more preferably a fluorine atom. When the alkyl group has, as a substituent, a fluorine atom, it may be a perfluoroalkyl group.

Note that, in the alkyl group, when a carbon atom serving as a bonding site has a substituent, it is also preferably a substituent other than a fluorine atom and a cyano group. In the alkyl group, the carbon atom serving as the bonding site corresponds to, for example, in the case of Formulas (BX-1) and (BX-4), the carbon atom directly bonded to —CO— clearly described in the formula of such an alkyl group; in the case of Formulas (BX-2) and (BX-3), the carbon atom directly bonded to $—SO_2—$ clearly described in the formula of such an alkyl group; in the case of Formula (BX-6), the carbon atom directly bonded to $N^-$ clearly described in the formula of the alkyl group.

In the alkyl group, a carbon atom may be replaced by a carbonyl carbon.

The aryl group is preferably a phenyl group or a naphthyl group, more preferably a phenyl group.

The aryl group may have a substituent. The substituent is preferably a fluorine atom, an iodine atom, a perfluoroalkyl group (for example, preferably having 1 to 10 carbon atoms, more preferably 1 to 6 carbon atoms), a cyano group, an alkyl group (for example, preferably having 1 to 10 carbon atoms, more preferably 1 to 6 carbon atoms), an alkoxy group (for example, preferably having 1 to 10 carbon atoms, more preferably 1 to 6 carbon atoms), or an alkoxycarbonyl group (for example, preferably having 2 to 10 carbon atoms, more preferably 2 to 6 carbon atoms), more preferably a fluorine atom, an iodine atom, a perfluoroalkyl group, an alkyl group, an alkoxy group, or an alkoxycarbonyl group.

In Formula (Ia-1), the divalent linking group represented by $L_1$ is not particularly limited; examples include —CO—, —NR—, —O—, —S—, —SO—, $—SO_2—$, an alkylene group (preferably has 1 to 6 carbon atoms and may be linear or branched), a cycloalkylene group (preferably having 3 to 15 carbon atoms), an alkenylene group (preferably having 2 to 6 carbon atoms), a divalent aliphatic heterocyclic group (preferably a five- to ten-membered ring having at least one N atom, O atom, S atom, or Se atom within the ring structure, more preferably a five- to seven-membered ring, still more preferably a five- to six-membered ring), a divalent aromatic heterocyclic group (preferably a five- to ten-membered ring having at least one N atom, 0 atom, S atom, or Se atom within the ring structure, more preferably a five- to seven-membered ring, still more preferably a five- to six-membered ring), a divalent aromatic hydrocarbon cyclic group (preferably a six- to ten-membered ring, more preferably a six-membered ring), and a divalent linking group provided by combining a plurality of the foregoing. R above may be a hydrogen atom or a monovalent organic group. The monovalent organic group is not particularly limited, but is preferably, for example, an alkyl group (preferably having 1 to 6 carbon atoms).

The alkylene group, the cycloalkylene group, the alkenylene group, the divalent aliphatic heterocyclic group, the divalent aromatic heterocyclic group, and the divalent aromatic hydrocarbon cyclic group may have a substituent. Examples of the substituent include halogen atoms (preferably a fluorine atom).

In particular, the divalent linking group represented by $L_1$ is preferably a divalent linking group represented by Formula (L1).

(L1)

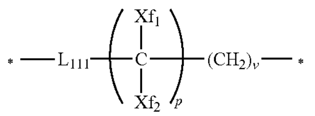

In Formula (L1), $L_{111}$ represents a single bond or a divalent linking group.

The divalent linking group represented by $L_{111}$ is not particularly limited and examples include —CO—, —NH—, —O—, —SO—, $—SO_2—$, an alkylene group that may have a substituent (preferably has 1 to 6 carbon atoms more preferably, and may be linear or branched), a cycloalkylene group that may have a substituent (preferably having 3 to 15 carbon atoms), an aryl group that may have a substituent (preferably having 6 to 10 carbon atoms), and a divalent linking group provided by combining a plurality of the foregoing. The substituent is not particularly limited, but may be, for example, a halogen atom.

p represents an integer of 0 to 3, preferably represents an integer of 1 to 3.

v represents an integer of 0 or 1.

$Xf_1$ each independently represent a fluorine atom or an alkyl group substituted with at least one fluorine atom. The alkyl group preferably has 1 to 10 carbon atoms, more preferably 1 to 4 carbon atoms. The alkyl group substituted with at least one fluorine atom is preferably a perfluoroalkyl group.

$Xf_2$ each independently represent a hydrogen atom, an alkyl group that may have, as a substituent, a fluorine atom, or a fluorine atom. The alkyl group preferably has 1 to 10 carbon atoms, more preferably 1 to 4 carbon atoms. In particular, $Xf_2$ preferably represent a fluorine atom or an alkyl group substituted with at least one fluorine atom, more preferably a fluorine atom or a perfluoroalkyl group.

In particular, $Xf_1$ and $Xf_2$ are each independently preferably a fluorine atom or a perfluoroalkyl group having 1 to 4 carbon atoms, more preferably a fluorine atom or $CF_3$. In particular, $Xf_1$ and $Xf_2$ are each still more preferably a fluorine atom.

* represent a bonding site.

When, in Formula (Ia-1), $L_{11}$ represents a divalent linking group represented by Formula ($L_1$), the $L_{111}$-side direct bond (*) in Formula (L1) is preferably bonded to $A_{12}^-$ in Formula (Ia-1).

Compounds Represented by Formulas (Ia-2) to (Ia-4)

Hereinafter, compounds represented by Formulas (Ia-2) to (Ia-4) will be described.

(Ia-2)

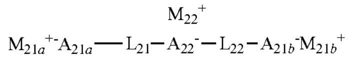

(Ia-3)

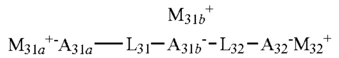

(Ia-4)

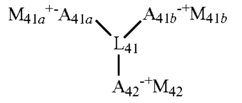

In Formula (Ia-2), $A_{21a}^-$ and $A_{21b}^-$ each independently represent a monovalent anionic functional group. For $A_{21a}^-$ and $A_{21b}^-$, the monovalent anionic functional group means a monovalent group including the above-described anionic moiety $A_1^-$. For $A_{21a}^-$ and $A_{21b}^-$, the monovalent anionic functional group is not particularly limited, but may be, for example, a monovalent anionic functional group selected from the group consisting of the above-described Formulas (AX-1) to (AX-3).

$A_{22}^-$ represents a divalent anionic functional group. The divalent anionic functional group represented by $A_{22}^-$ means a divalent linking group including the above-described anionic moiety $A_2^-$. For the divalent anionic functional group represented by $A_{22}^-$, examples include divalent anionic functional groups represented by the following Formulas (BX-8) to (BX-11).

BX-8

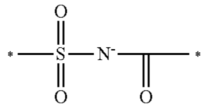

BX-9

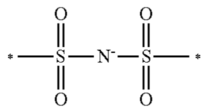

BX-10

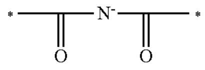

BX-11

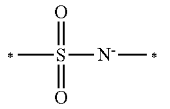

$M_{21a}^+$, $M_{21b}^+$, and $M_{22}^+$ each independently represent an organic cation. For $M_{21a}^+$, $M_{21b}^+$, and $M_{22}^+$, the organic cation has the same definition and preferred examples as in the above-described $M_1^+$.

$L_{21}$ and $L_{22}$ each independently represent a divalent organic group.

In a compound PIa-2 in which, in Formula (Ia-2) above, the organic cations represented by $M_{21a}^+$, $M_{21b}^+$, and $M_{22}^+$ are replaced by $H^+$, the acid dissociation constant a2 derived from the acidic moiety represented by $A_{22}H$ is larger than the acid dissociation constant a1-1 derived from $A_{21a}H$ and the acid dissociation constant a1-2 derived from the acidic moiety represented by $A_{21b}H$. Note that the acid dissociation constant a1-1 and the acid dissociation constant a1-2 correspond to the above-described acid dissociation constant a1.

Note that $A_{21a}^+$ and $A_{21b}^+$ may be the same or different. $M_{21a}^+$, $M_{21b}^+$, and $M_{22}^+$ may be the same or different.

At least one of $M_{21a}^+$, $M_{21b}^+$, $M_{22}^+$, $A_{21a}^-$, $A_{21b}^-$, $L_{21}$, or $L_{22}$ may have, as a substituent, an acid-decomposable group.

In Formula (Ia-3), A31a and A32- each independently represent a monovalent anionic functional group. Note that the monovalent anionic functional group represented by $A_{31a}^-$ has the same definition and preferred examples as in the above-described $A_{21a}^-$ and $A_{21b}^-$ in Formula (Ia-2).

The monovalent anionic functional group represented by $A_{32}^-$ means a monovalent group including the above-described anionic moiety $A_2^-$. The monovalent anionic functional group represented by $A_{32}^-$ is not particularly limited, but may be, for example, a monovalent anionic functional group selected from the group consisting of the above-described Formulas (BX-1) to (BX-7).

$A_{31}^-$ represents a divalent anionic functional group. The divalent anionic functional group represented by $A_{31b}^-$ means a divalent linking group including the above-described anionic moiety $A_1^-$. The divalent anionic functional group represented by $A_{31b}^-$ may be, for example, a divalent anionic functional group represented by the following Formula (AX-4).

AX-4

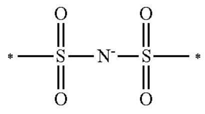

$M_{31a}^+$, $M_{31b}^+$, and $M_{32}^+$ each independently represent a monovalent organic cation. For $M_{31a}^+$, $M_{31b}^+$, and $M_{32}^+$, the organic cation has the same definitions and preferred examples as in the above-described $M_1^+$.

$L_{31}$ and $L_{32}$ each independently represent a divalent organic group.

In a compound PIa-3 in which, in Formula (Ia-3) above, the organic cations represented by $M_{31a}^+$, $M_{31b}^+$, and $M_{32}^+$ are replaced by $H^+$, the acid dissociation constant a2 derived from the acidic moiety represented by $A_{32}H$ is larger than the acid dissociation constant a1-3 derived from the acidic moiety represented by $A_{31a}H$ and the acid dissociation constant a1-4 derived from the acidic moiety represented by $A_{31b}H$. Note that the acid dissociation constant a1-3 and the acid dissociation constant a1-4 correspond to the above-described acid dissociation constant a1. Note that $A_{31a}^-$ and $A_{32}^-$ may be the same or different. $M_{31a}^+$, $M_{31b}^+$, and $M_{32}^+$ may be the same or different.

At least one of $M_{31a}^+$, $M_{31b}^+$, $M_{32}^+$, $A_{31a}^-$, $A_{32}^-$, $L_{31}$, or $L_{32}$ may have, as a substituent, an acid-decomposable group.

In Formula (Ia-4), $A_{41a}^-$, $A_{41b}^-$, and $A_{42}^-$ each independently represent a monovalent anionic functional group. Note that, for $A_{41a}^-$ and $A_{41b}^-$, the monovalent anionic functional group has the same definition as in the above-described $A_{21a}^-$ and $A_{21b}^-$ in Formula (Ia-2). The monovalent anionic functional group represented by $A_{42}^-$ has the same definition and preferred examples as in the above-described $A_{32}^-$ in Formula (Ia-3).

$M_{41a}^+$, $M_{41b}^+$, and $M2^+$ each independently represent an organic cation.

$L_{41}$ represents a trivalent organic group.

In a compound PIa-4 in which, in Formula (Ia-4) above, the organic cations represented by $M_{41a}^+$, $M_{41b}^+$, and $M_{42}^+$ are replaced by $H^+$, the acid dissociation constant a2 derived from the acidic moiety represented by $A_{42}H$ is larger than the acid dissociation constant a1-5 derived from the acidic moiety represented by $A_{41a}H$ and the acid dissociation constant a1-6 derived from the acidic moiety represented by $A_{41b}H$. Note that the acid dissociation constant a1-5 and the acid dissociation constant a1-6 correspond to the above-described acid dissociation constant a1.

Note that $A_{41a}^-$, $A_{41b}^-$, and $A_{42}^-$ may be the same or different. $M_{41a}^+$, $M_{41b}^+$, and $M_{42}^+$ may be the same or different.

At least one of $M_{41a}^+$, $M_{41a}^+$, $M_{42}^+$, $A_{41a}^-$, $A_{41b}^-$, $A_{42}^-$, or $L_{41}$ may have, as a substituent, an acid-decomposable group.

For $L_{21}$ and $L_{22}$ in Formula (Ia-2) and $L_{31}$ and $L_{32}$ in Formula (Ia-3), the divalent organic group is not particularly limited and may be, for example, —CO—, —NR—, —O—, —S—, —SO—, —$SO_2$—, an alkylene group (preferably has 1 to 6 carbon atoms and may be linear or branched), a cycloalkylene group (preferably having 3 to 15 carbon atoms), an alkenylene group (preferably having 2 to 6 carbon atoms), a divalent aliphatic heterocyclic group (preferably a five- to ten-membered ring having at least one N atom, O atom, S atom, or Se atom within the ring structure, more preferably a five- to seven-membered ring, still more preferably a five- to six-membered ring), a divalent aromatic heterocyclic group (preferably a five- to ten-membered ring having at least one N atom, O atom, S atom, or Se atom within the ring structure, more preferably a five- to seven-membered ring, still more preferably a five- to six-membered ring), a divalent aromatic hydrocarbon cyclic group (preferably a six- to ten-membered ring, more preferably a six-membered ring), or a divalent organic group provided by combining a plurality of the foregoing. In —NR— above, R may be a hydrogen atom or a monovalent organic group. The monovalent organic group is not particularly limited, but is preferably, for example, an alkyl group (preferably having 1 to 6 carbon atoms).

The alkylene group, the cycloalkylene group, the alkenylene group, the divalent aliphatic heterocyclic group, the divalent aromatic heterocyclic group, and the divalent aromatic hydrocarbon cyclic group may have a substituent. Examples of the substituent include halogen atoms (preferably a fluorine atom).

For $L_{21}$ and $L_{22}$ in Formula (Ia-2) and $L_{31}$ and $L_{32}$ in Formula (Ia-3), the divalent organic group is also preferably, for example, a divalent organic group represented by the following Formula (L2).

(L2)

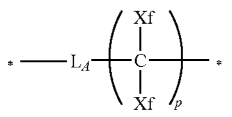

In Formula (L2), q represents an integer of 1 to 3. * represent a bonding site.

Xf each independently represent a fluorine atom or an alkyl group substituted with at least one fluorine atom. The alkyl group preferably has 1 to 10 carbon atoms, more preferably 1 to 4 carbon atoms. The alkyl group substituted with at least one fluorine atom is preferably a perfluoroalkyl group.

Xf are preferably a fluorine atom or a perfluoroalkyl group having 1 to 4 carbon atoms, more preferably a fluorine atom or $CF_3$. In particular, still more preferably, both of Xf are fluorine atoms.

$L_A$ represents a single bond or a divalent linking group.

The divalent linking group represented by $L_A$ is not particularly limited, but may be, for example, —CO—, —O—, —SO—, —$SO_2$—, an alkylene group (preferably has 1 to 6 carbon atoms and may be linear or branched), a cycloalkylene group (preferably having 3 to 15 carbon atoms), a divalent aromatic hydrocarbon cyclic group (preferably a six- to ten-membered ring, more preferably a six-membered ring), or a divalent linking group provided by combining a plurality of the foregoing.

The alkylene group, the cycloalkylene group, and the divalent aromatic hydrocarbon cyclic group may have a substituent. Examples of the substituent include halogen atoms (preferably a fluorine atom).

Examples of the divalent organic group represented by Formula ($L_2$) include *—$CF_2$—*, *—$CF_2$—$CF_2$—*, *—$CF_2$—$CF_2$—$CF_2$—*, *-Ph-O—$SO_2$—$CF_2$—*, *-Ph-O—$SO_2$—$CF_2$—$CF_2$—*, *-Ph-O—$SO_2$—$CF_2$—$CF_2$—$CF_2$—*, and *-Ph-OCO—$CF_2$—*. Note that Ph are a phenylene group that may have a substituent, preferably a 1,4-phenylene group. The substituent is not particularly limited, but is preferably an alkyl group (for example, preferably having 1 to 10 carbon atoms, more preferably 1 to 6 carbon atoms), an alkoxy group (for example, preferably having 1 to 10 carbon atoms, more preferably 1 to 6 carbon atoms), or an alkoxycarbonyl group (for example, preferably having 2 to 10 carbon atoms, more preferably 2 to 6 carbon atoms).

When $L_{21}$ and $L_{22}$ in Formula (Ia-2) represent the divalent organic group represented by Formula ($L_2$), the $L_A$-side direct bond (*) in Formula ($L_2$) is preferably bonded to $A_{21a}^-$ and $A_{21b}^-$ in Formula (Ia-2).

When $L_{31}$ and $L_{32}$ in Formula (Ia-3) represent the divalent organic group represented by Formula (L2), the $L_A$-side direct bond (*) in Formula (L2) is preferably bonded to $A_{31a}^-$ and $A_{32}^-$ in Formula (Ia-3).

Compound Represented by Formula (Ia-5)

Hereinafter, Formula (Ia-5) will be described.

(Ia-5)

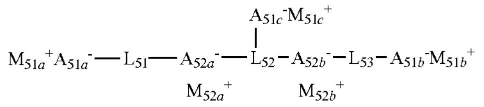

In Formula (Ia-5), $A_{51a}^-$, $A_{51b}^-$, and $A_{51a}^-$ each independently represent a monovalent anionic functional group. For $A_{51a}^-$, $A_{51b}^-$, and $A_{51c}^-$, the monovalent anionic functional group means a monovalent group including the above-described anionic moiety $A_1^+$. For $A_{51a}^-$, $A_{51b}^-$, and $A_{51c}^-$, the monovalent anionic functional group is not particularly limited, but may be, for example, a monovalent anionic functional group selected from the group consisting of the above-described Formulas (AX-1) to (AX-3).

$A_{52a}^-$ and $A_{52b}^-$ represent a divalent anionic functional group. For $A_{52a}^+$ and $A_{52b}^-$, the divalent anionic functional group means a divalent linking group including the above-described anionic moiety $A_2^-$. The divalent anionic functional group represented by $A_{22}^-$ may be, for example, a divalent anionic functional group selected from the group consisting of the above-described Formulas (BX-8) to (BX-11).

$M_{51a}^+$, $M_{51b}^+$, $M_{51c}^+$, $M_{52a}^+$, and $M_{52b}^+$ each independently represent an organic cation. For $M_{51a}^+$, $M_{51b}^+$, $M_{51c}^+$, $M_{52a}^+$, and $M_{52b}^+$, the organic cation has the same definition and preferred examples as in the above-described $M_1$*.

$L_{51}$ and $L_{53}$ each independently represent a divalent organic group. For $L_{51}$ and $L_{53}$, the divalent organic group has the same definition and preferred examples as in the above-described $L_{21}$ and $L_{22}$ in Formula (Ia-2).

$L_{52}$ represents a trivalent organic group. The trivalent organic group represented by $L_{52}$ has the same definition and preferred examples as in the above-described $L_{41}$ in Formula (Ia-4).

In a compound PIa-5 in which, in Formula (Ia-5) above, the organic cations represented by $M_{51a}^+$, $M_{51b}^+$, $M_{51c}^+$, $M_{52a}^+$, and $M_{52b}^+$ are replaced by $H^+$, the acid dissociation constant a2-1 derived from the acidic moiety represented by $A_{52a}H$ and the acid dissociation constant a2-2 derived from the acidic moiety represented by $A_{52b}H$ are larger than the acid dissociation constant a1-1 derived from $A_{51a}H$, the acid dissociation constant a1-2 derived from the acidic moiety represented by $A_{51b}H$, and the acid dissociation constant a1-3 derived from the acidic moiety represented by $A_{51c}H$. Note that the acid dissociation constants a1-1 to a1-3 correspond to the above-described acid dissociation constant a1, and the acid dissociation constants a2-1 and a2-2 correspond to the above-described acid dissociation constant a2.

Note that $A_{51a}^-$, $A_{51b}^-$, and $A_{51c}^-$ may be the same or different. $A_{52a}^-$ and $A_{52b}^-$ may be the same or different. $M_{51a}^+$, $M_{51b}^+$, $M_{51c}^+$, $M_{52a}^+$, and $M_{52b}^+$ may be the same or different. At least one of $M_{51b}^+$, $M_{52c}^+$, $M_{52a}^+$, $M_{52b}^+$, $A_{51a}^-$, $A_{51b}^-$, $A_{51c}^-$, $L_{51}$, $L_{52}$, or $L_{53}$ may have, as a substituent, an acid-decomposable group.

Compound (II)

A compound (II) is a compound having two or more moieties X above and one or more moieties Z below and is an acid generation compound including a compound that is irradiated with an actinic ray or radiation to generate an acid including two or more first acidic moieties above derived from the moiety X and the moiety Z.

Moiety Z: a nonionic moiety that can neutralize acid

In the compound (11), the moiety X, $A_1^-$, and $M_1^+$ have the same definitions and preferred examples as the above-described moiety X, $A_1^-$, and $M_1^+$ in the compound (I).

In a compound PI in which, in the compound (II), the cationic moiety $M_1^+$ in the moiety X is replaced by $H^+$, the acid dissociation constant a1 derived from the acidic moiety represented by $HA_1$ in which the above-described cationic moiety $M_1^+$ in the moiety X is replaced by $H^+$ has the same preferred range as in the acid dissociation constant a1 in the compound PI.

When the compound (II) is, for example, a compound that generates an acid having two first acidic moieties derived from the moiety X and the moiety Z, the compound PH corresponds to "compound having two $HA_1$". When the acid dissociation constant of this compound PI is determined, the acid dissociation constant determined when the compound PII is turned into "compound having a single $A_1^-$ and a single $HA_1$" and the acid dissociation constant determined when the "compound having a single $A_1^-$ and a single $HA_1$" is turned into "compound having two $A_1^-$" correspond to the acid dissociation constant a1.

The acid dissociation constant a1 can be determined by the above-described method of measuring an acid dissociation constant.

The compound PII corresponds to an acid generated upon irradiation of the compound (II) with an actinic ray or radiation.

Note that the two or more moieties X may be the same or different. The two or more $A_1^-$ and the two or more $M_1^+$ may be individually the same or different.

The nonionic moiety that can neutralize acid in the moiety Z is not particularly limited, and is preferably, for example, a moiety including a group that can electrostatically interact with a proton or a functional group having an electron.

The group that can electrostatically interact with a proton or the functional group having an electron may be a functional group having a macrocyclic structure such as a cyclic polyether or a functional group having a nitrogen atom having an unshared electron pair not contributing to n conjugation. The nitrogen atom having an unshared electron pair not contributing to a conjugation is, for example, nitrogen atoms having moieties represented by the following formulas.

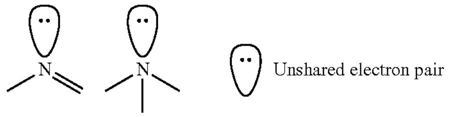

The moiety of the group that can electrostatically interact with a proton or the functional group having an electron is, for example, a crown ether moiety, an azacrown ether moiety, a primary to tertiary amine moiety, a pyridine moiety, an imidazole moiety, or a pyrazine moiety; in particular, preferably a primary to tertiary amine moiety.

The compound (II) is not particularly limited; examples include compounds represented by the following Formula (IIa-1) and the following Formula (IIa-2).

(IIa-1)

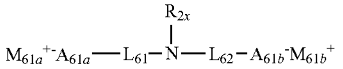

(IIa-2)

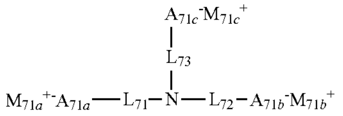

In Formula (IIa-1) above, $A_{61a}^-$ and $A_{61b}^-$ have the same definitions and preferred examples as in the above-described $A_{11}^-$ in Formula (Ia-1). $M_{61a}^+$ and $M_{61b}^+$ have the same definitions and preferred examples as in the above-described $M_{11}^+$ in Formula (Ia-1).

In Formula (IIa-1) above, $L_{61}$ and $L_{62}$ have the same definitions and preferred examples as in the above-described $L_1$ in Formula (Ia-1).

In Formula (IIa-1), $R_{2X}$ represents a monovalent organic group. The monovalent organic group represented by $R_{2X}$ is not particularly limited and may be an alkyl group (preferably has 1 to 10 carbon atoms and may be linear or branched), a cycloalkyl group (preferably having 3 to 15 carbon atoms), or an alkenyl group (preferably having 2 to 6 carbon atoms). In the monovalent organic group represented by $R_{2X}$, $—CH_2—$ included in the alkyl group, cycloalkyl group, or alkenyl group may be substituted with one or a combination of two or more selected from the group consisting of —CO—, —NH—, —O—, —S—, —SO—, and $—SO_2—$.

The alkylene group, the cycloalkylene group, and the alkenylene group may have a substituent. The substituent is not particularly limited, but may be, for example, a halogen atom (preferably a fluorine atom).

In a compound PIIa-1 in which, in Formula (IIa-1) above, the organic cations represented by $M_{61a}^+$ and $M_{61b}^+$ are replaced by $H^+$, the acid dissociation constant a1-7 derived from the acidic moiety represented by $A_{61a}H$ and the acid dissociation constant a1-8 derived from the acidic moiety represented by $A_{61b}H$ correspond to the above-described acid dissociation constant a1.

The compound PIIa-1 in which, in the compound (IIa-1), the cationic moieties $M_{61a}^+$ and $M_{61b}^+$ in the moieties X are replaced by H corresponds to $HA_{61a}$-$L_{62}$-$N(R_{2X})$-$L_{62}$-$A_{61b}H$. The compound PIIa-1 is the same as the acid generated from the compound represented by Formula (IIa-1) in response to irradiation with an actinic ray or radiation.

At least one of $M_{61a}^+$, $M_{61b}^+$, $A_{61a}^-$, $A_{61b}^-$, $L_{62}$, $L_{62}$, or $R_{2X}$ may have, as a substituent, an acid-decomposable group.

In Formula (IIa-2) above, $A_{71a}^-$, $A_{71b}^-$, and $A_{71c}^-$ have the same definitions and preferred examples as in the above-described $A_{11}^-$ in Formula (Ia-1). $M_{71a}^+$, $M_{71b}^+$, and $M_{71c}^+$ have the same definitions and preferred examples as in the above-described $M_{11}^+$ in Formula (Ia-1).

In Formula (IIa-2) above, $L_{71}$, $L_{72}$, and $L_{73}$ have the same definitions and preferred examples as in the above-described $L_1$ in Formula (Ia-1).

In a compound PIIa-2 in which, in Formula (IIa-2) above, the organic cations represented by $M_{71a}^+$, $M_{71b}^+$, and $M_{71c}^+$ are replaced by $H^+$, the acid dissociation constant a1-9 derived from the acidic moiety represented by $A_{71a}H$, the acid dissociation constant a1-10 derived from the acidic moiety represented by $A_{71b}H$, and the acid dissociation constant a1-II derived from the acidic moiety represented by $A_{71c}H$ correspond to the above-described acid dissociation constant a1.

Note that the compound PIIa-2 in which, in the compound (Ha-1), the cationic moieties $M_{71a}^+$, $M_{71b}^+$, and $M_{71c}^+$ in the moieties X are replaced by $H^+$ corresponds to $HA_{71a}$-$L_{71}$-$N(L_{73}$-$A_{71c}H)$-$L_{72}$-$A_{71b}H$. The compound PIIa-2 is the same as the acid generated from the compound represented by Formula (IIa-2) in response to irradiation with an actinic ray or radiation.

At least one of $M_{71a}^+$, $M_{71b}^+$, $M_{71c}^+$, $A_{71a}^-$, $A_{71b}^-$, $A_{71c}^-$, $L_{71}$, $L_{72}$, or $L_{73}$ may have, as a substituent, an acid-decomposable group.

Examples of non-cation moieties that the compound (I) and the compound (II) can have will be described below.

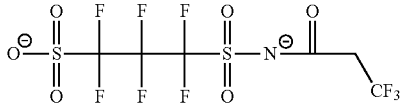

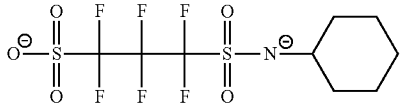

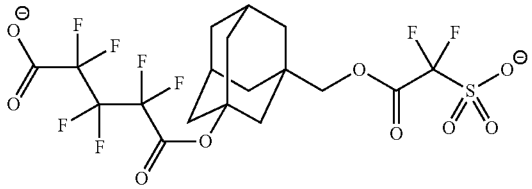

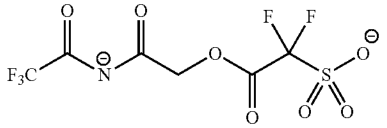

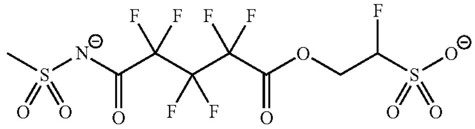

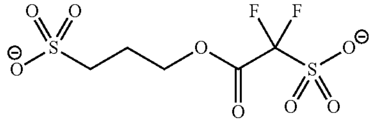

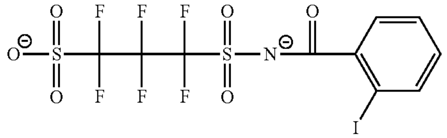

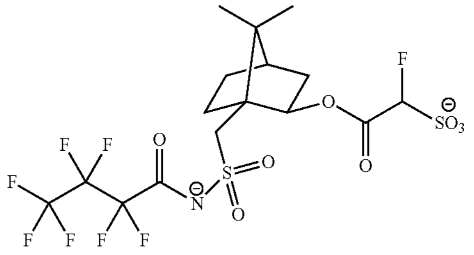

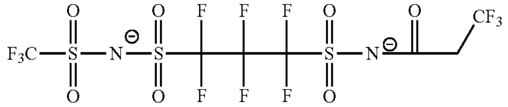

-continued
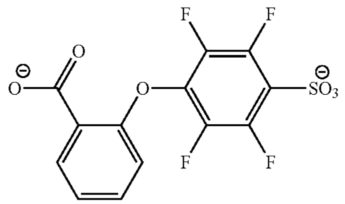
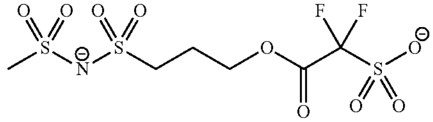
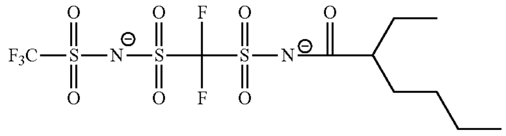
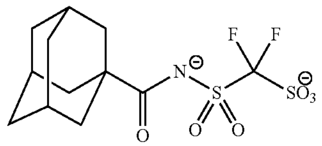
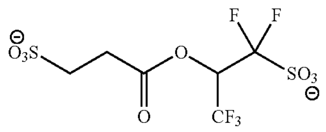
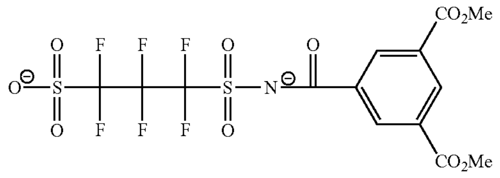
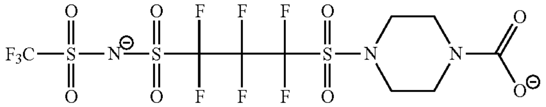
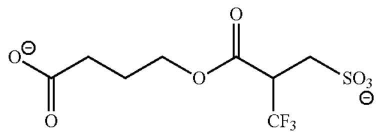
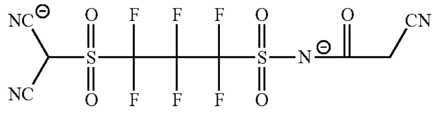
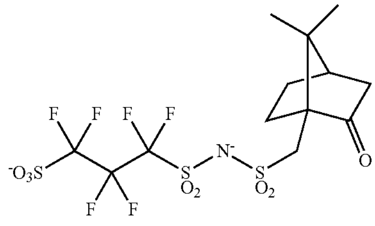
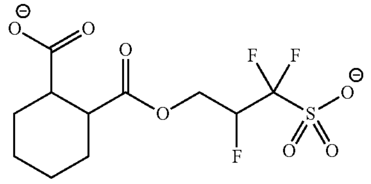
-continued
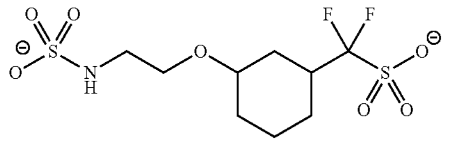
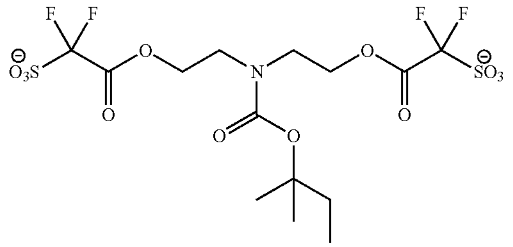
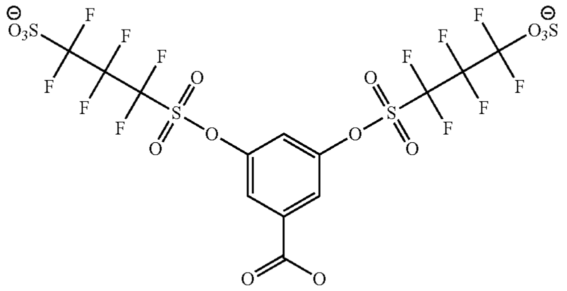
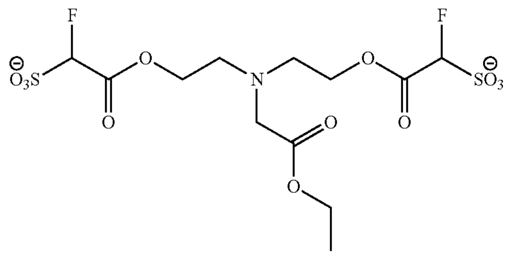
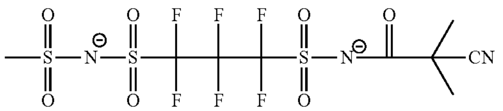
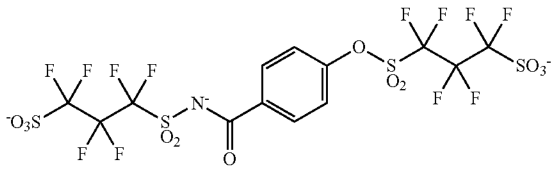
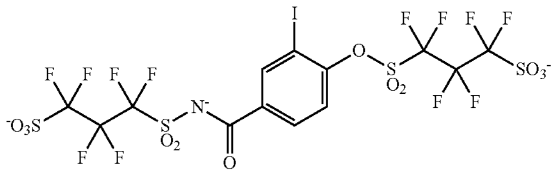
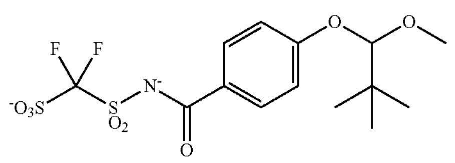

-continued
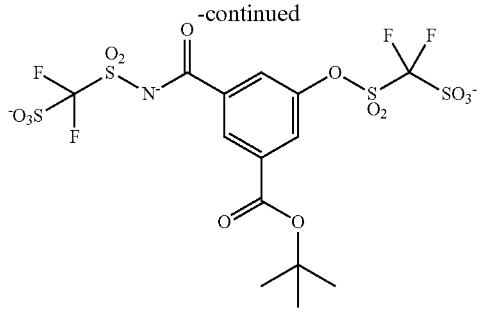
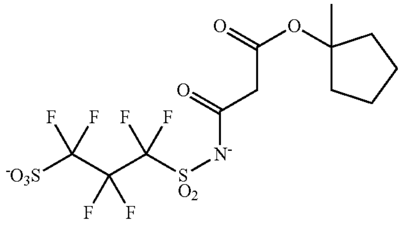
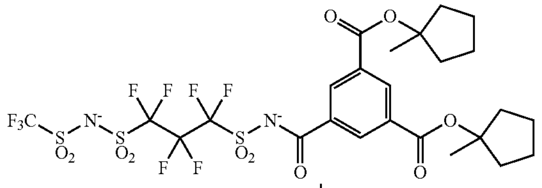
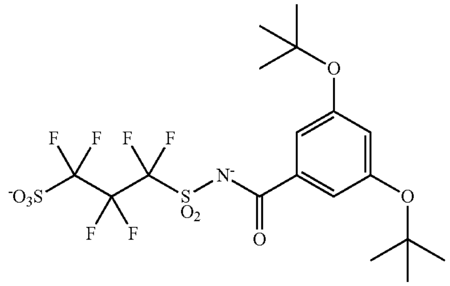
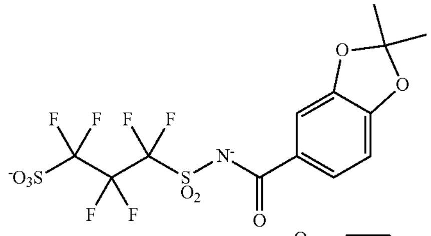
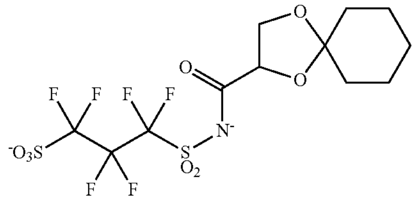
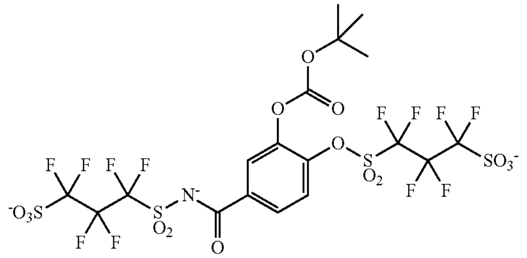
The following are non-limiting specific examples of the photoacid generator.
X-1
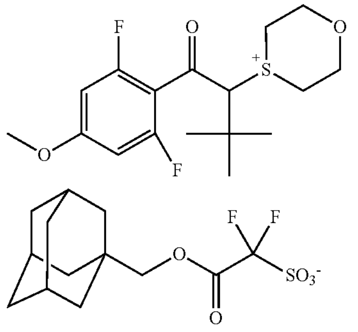
X-2
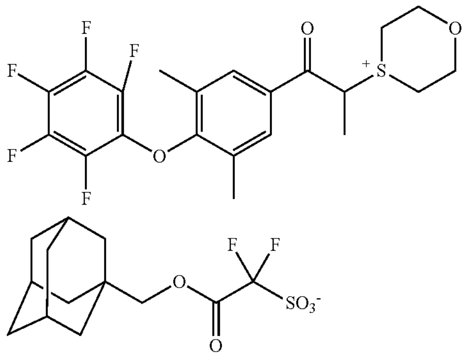
X-3
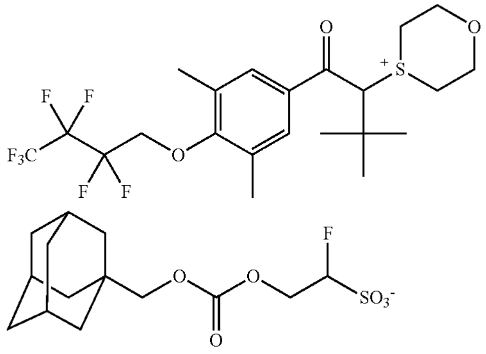
X-4
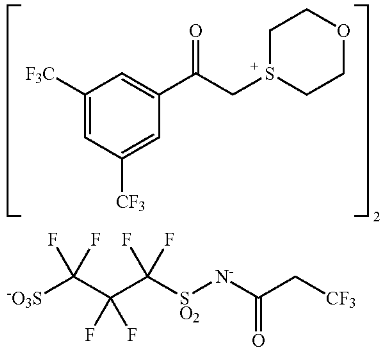
X-5
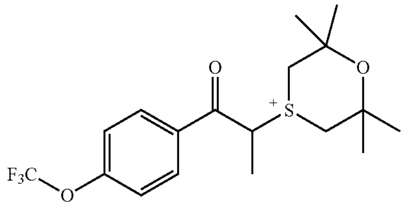

-continued
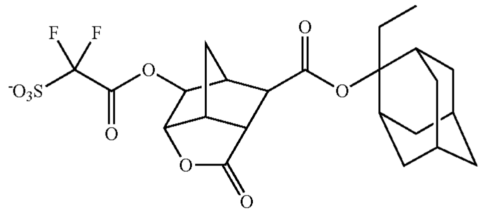
X-6
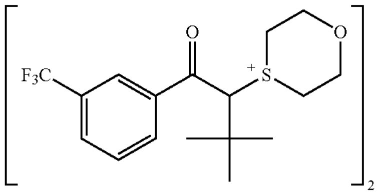
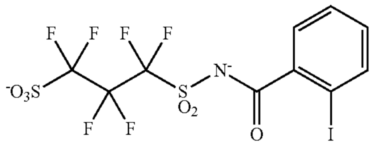
X-7
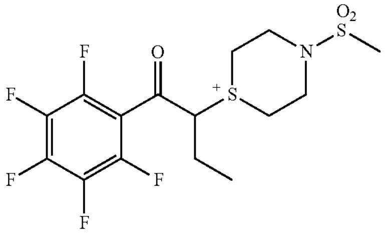
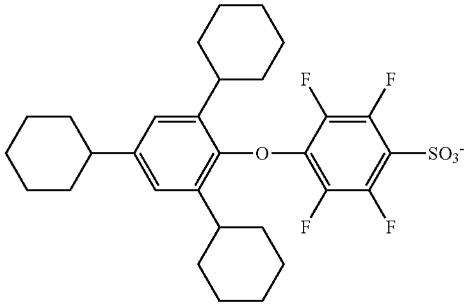
X-8
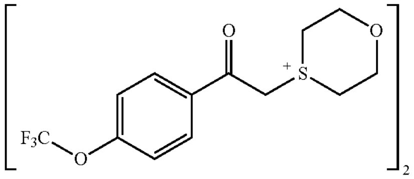
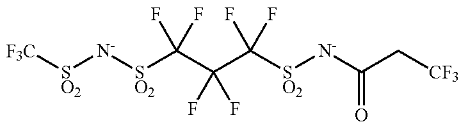
X-9
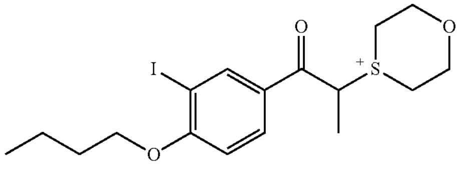
-continued
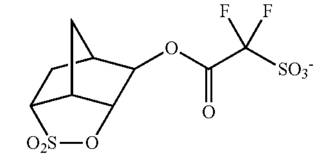
X-10
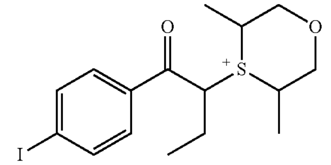
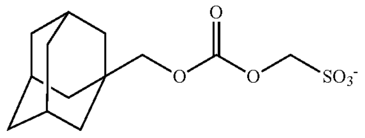
X-11
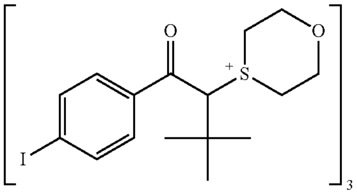
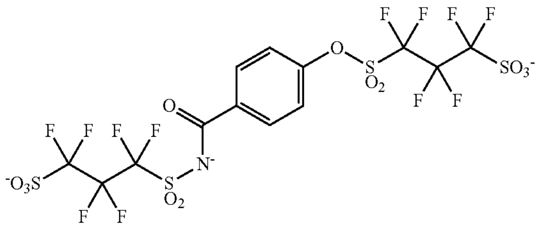
X-12
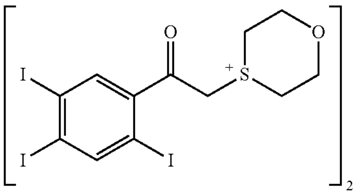
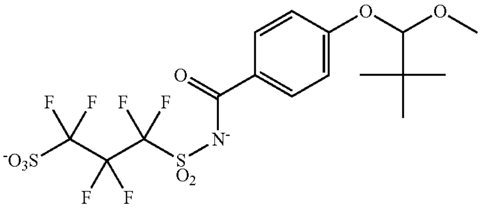
X-13
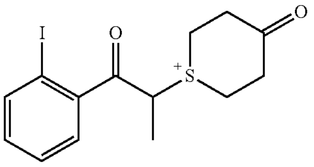
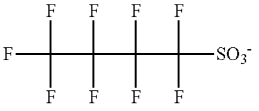

-continued
X-14
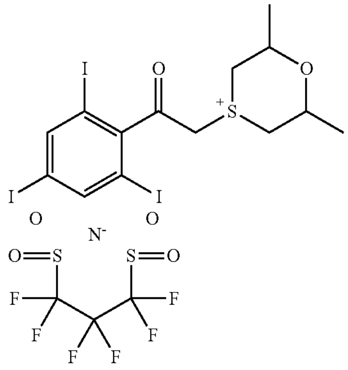
X-15
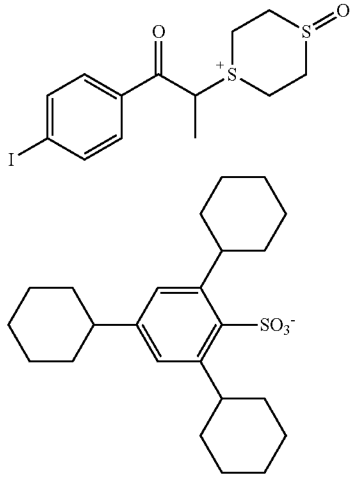
X-16
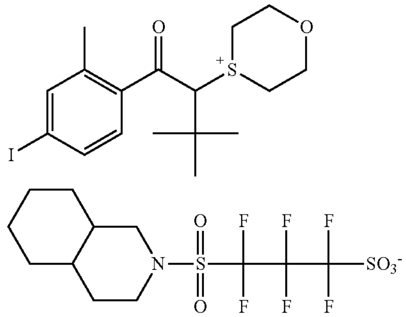
X-17
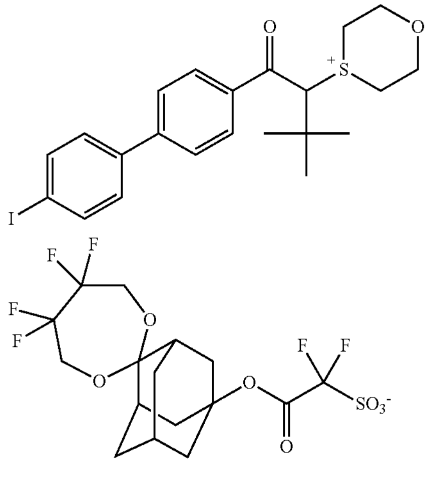
-continued
X-18
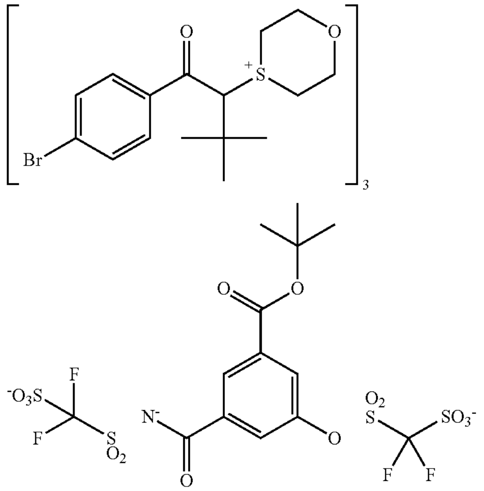
X-19
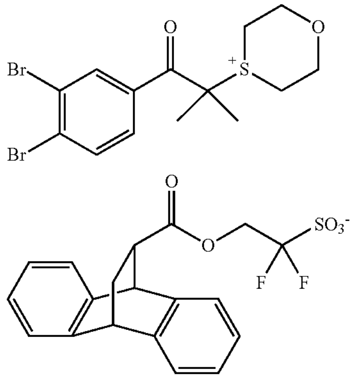
X-20
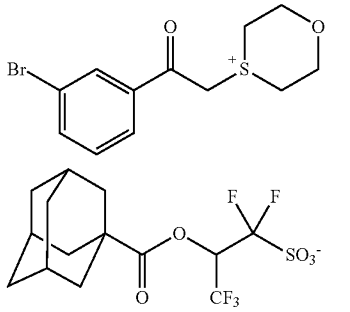
X-21
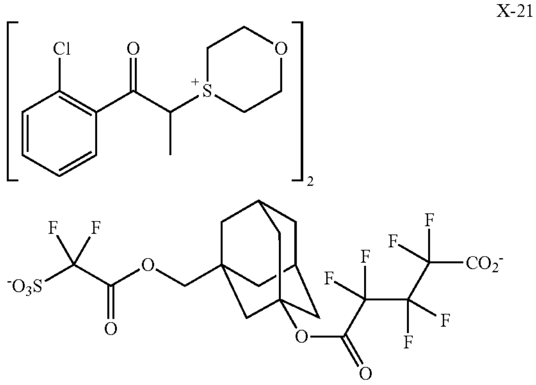

-continued

X-22

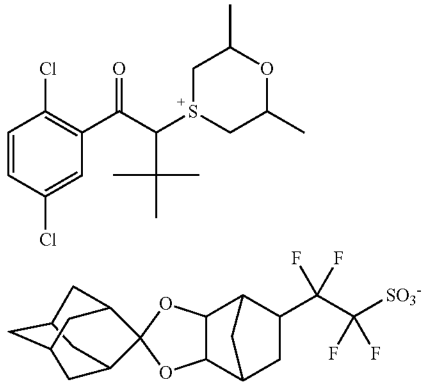

X-23

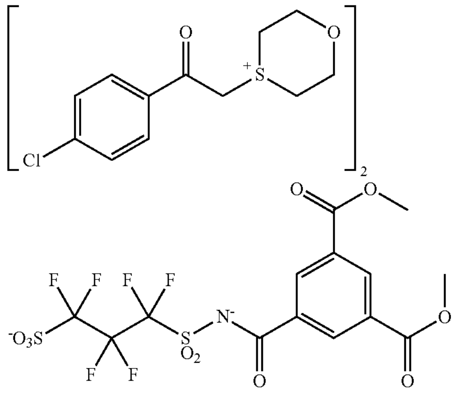

X-24

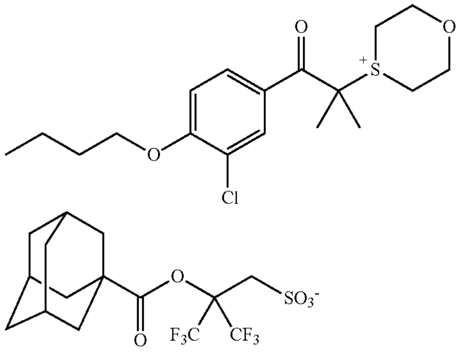

When the actinic ray-sensitive or radiation-sensitive resin composition includes the photoacid generator (B), its content is not particularly limited, but is, from the viewpoint of forming a pattern having a more square profile, relative to the total solid content of the actinic ray-sensitive or radiation-sensitive resin composition, preferably 0.5 mass % or more, more preferably 1.0 mass % or more. The content relative to the total solid content of the actinic ray-sensitive or radiation-sensitive resin composition is preferably 50.0 mass % or less, more preferably 30.0 mass % or less, still more preferably 25.0 mass % or less.

In the actinic ray-sensitive or radiation-sensitive resin composition, when the mass-based content of the onium salt (C) is defined as $A_C$ and the mass-based content of the photoacid generator (B) is defined as $A_B$, $A_C$:$A_B$ is preferably 1:4 to 4:1, more preferably 1:3 to 3:1, still more preferably 1:2 to 2:1.

Such photoacid generators (B) may be used alone or in combination of two or more thereof.

Acid Diffusion Control Agent Other than Onium Salt (C)

As described above, the onium salt (C) can function as an acid diffusion control agent.

The actinic ray-sensitive or radiation-sensitive resin composition may include an acid diffusion control agent other than the onium salt (C).

In the above-described step (3), in addition to the onium salt (C) and the resin (A), an acid diffusion control agent other than the onium salt (C) may be mixed.

The species of the acid diffusion control agent other than the onium salt (C) is not particularly limited; examples include basic compounds, low-molecular-weight compounds having a nitrogen atom and having a group that leaves due to the action of acid, basic compounds that undergo reduction or loss of the basicity in response to irradiation with an actinic ray or radiation, and onium salt compounds having, in the cationic moiety, a nitrogen atom.

Specific examples of the basic compounds include the compounds described in Paragraphs [0132] to [0136] in WO2020/066824A; specific examples of the basic compounds that undergo reduction or loss of the basicity in response to irradiation with an actinic ray or radiation include the compounds described in Paragraphs [0137] to [0155] in WO2020/066824A; specific examples of the low-molecular-weight compounds having a nitrogen atom and having a group that leaves due to the action of acid include the compounds described in Paragraphs [0156] to [0163] in WO2020/066824A; specific examples of the onium salt compound having, in the cationic moiety, a nitrogen atom include the compounds described in Paragraph [0164] in WO2020/066824A.

In addition to those described above, for example, the publicly known compounds disclosed in Paragraphs [0627] to [0664] in US2016/0070167A1, Paragraphs [0095] to [0187] in US2015/0004544A1, Paragraphs [0403] to [0423] in US2016/0237190A1, and Paragraphs [0259] to [0328] in US2016/0274458A1 are suitably usable as acid diffusion control agents.

When the actinic ray-sensitive or radiation-sensitive resin composition includes an acid diffusion control agent other than the onium salt (C), the content of the acid diffusion control agent other than the onium salt (C)(in the case of a plurality of species, the total thereof) relative to the total solid content of the actinic ray-sensitive or radiation-sensitive resin composition is preferably 0.01 to 10 mass %.

In the actinic ray-sensitive or radiation-sensitive resin composition, such acid diffusion control agents other than the onium salt (C) may be used alone or in combination of two or more thereof.

Hydrophobic Resin (D)

The actinic ray-sensitive or radiation-sensitive resin composition may further include a hydrophobic resin different from the resin (A).

In the above-described step (3), in addition to the onium salt (C) and the resin (A), a hydrophobic resin may be mixed.

The hydrophobic resin is preferably designed so as to be localized in the surface of a resist film; however, unlike surfactants, the hydrophobic resin does not necessarily need to have intramolecularly a hydrophilic group, and does not necessarily contribute to homogeneous mixing of a polar substance and a nonpolar substance.

Advantages due to addition of the hydrophobic resin may be control of static and dynamic contact angles (for water) at the surface of the resist film, and suppression of outgassing.

The hydrophobic resin, from the viewpoint of localization in the surface layer of the film, preferably has one or more, more preferably two or more, selected from the group consisting of a fluorine atom, a silicon atom, and a $CH_3$ moiety included in the side chain moiety of the resin. The hydrophobic resin preferably has a hydrocarbon group having 5 or more carbon atoms. The resin may have such a group in the main chain or, as a substituent, in a side chain.

Examples of the hydrophobic resin include the compounds described in Paragraphs [0275] to [0279] in WO2020/004306A.

When the actinic ray-sensitive or radiation-sensitive resin composition includes a hydrophobic resin, the content of the hydrophobic resin relative to the total solid content of the actinic ray-sensitive or radiation-sensitive resin composition is preferably 0.01 to 20.0 mass %, more preferably 0.1 to 15.0 mass %.

Surfactant (E)

The actinic ray-sensitive or radiation-sensitive resin composition may include a surfactant. In the case of including a surfactant, a pattern having higher adhesiveness and a less number of development defects can be formed.

In the above-described step (3), in addition to the onium salt (C) and the resin (A), a surfactant may be mixed.

The surfactant is preferably a fluorine-based and/or silicon-based surfactant.

Examples of the fluorine-based and/or silicon-based surfactant include the surfactants disclosed in Paragraphs [0218] and [0219] of WO2018/19395A.

Such surfactants may be used alone or in combination of two or more thereof.

When the actinic ray-sensitive or radiation-sensitive resin composition includes a surfactant, the surfactant content relative to the total solid content of the actinic ray-sensitive or radiation-sensitive resin composition is preferably 0.0001 to 2.0 mass %, more preferably 0.0005 to 1.0 mass %, still more preferably 0.1 to 1.0 mass %.

Solvent (F)

The actinic ray-sensitive or radiation-sensitive resin composition preferably includes a solvent.

The solvent preferably includes at least one of (M1) propylene glycol monoalkyl ether carboxylate or (M2) at least one selected from the group consisting of propylene glycol monoalkyl ether, lactate, acetate, alkoxypropionate, chain ketone, cyclic ketone, lactone, and alkylene carbonate. Note that the solvent may further include a component other than the components (M1) and (M2).

The above-described solvents and the above-described resin are preferably combined from the viewpoint of improvement in the coatability of the actinic ray-sensitive or radiation-sensitive resin composition and a reduction in the number of development defects of the pattern. The above-described solvents are well-balanced in terms of solubility of the above-described resin, boiling point, and viscosity, to thereby suppress, for example, unevenness of the film thickness of the resist film and generation of deposit during spin-coating.

Details of the component (M1) and the component (M2) are described in Paragraphs [0218] to [0226] in WO2020/004306A, and these contents are incorporated herein by reference.

When the solvent further includes a component other than the components (M1) and (M2), the content of the component other than the components (M1) and (M2) relative to the total amount of the solvent is preferably 5 to 30 mass %.

In the actinic ray-sensitive or radiation-sensitive resin composition, the content of the solvent is preferably set such that the concentration of solid content becomes 0.5 to 30 mass %, more preferably 1 to 20 mass %. In such a case, the actinic ray-sensitive or radiation-sensitive resin composition has further improved coatability.

Other Additives

The actinic ray-sensitive or radiation-sensitive resin composition may further include a dissolution inhibition compound, a dye, a plasticizer, a photosensitizer, a light absorbent, and/or a compound that improves solubility in developers (for example, a phenol compound having a molecular weight of 1000 or less or an alicyclic or aliphatic compound including a carboxy group).

The "dissolution inhibition compound" is a compound that is decomposed by the action of acid to undergo a decrease in the degree of solubility in organic-based developers, and has a molecular weight of 3000 or less.

The actinic ray-sensitive or radiation-sensitive resin composition in this Specification is suitably used as an EUV exposure photosensitive composition.

The EUV light has a wavelength of 13.5 nm, which is a shorter wavelength than in the ArF (wavelength: 193 nm) light and the like, and hence provides, upon exposure at the same sensitivity, a smaller number of incident photons. Thus, "photon shot noise", which is random variations in the number of photons, exerts a strong effect, which leads to degradation of LER and bridge defects. In order to reduce the photon shot noise, a method of increasing the exposure amount to increase the number of incident photons may be employed; however, there is a tradeoff between this method and higher sensitivity in demand.

When a value A determined by Formula (1) below is large, the resist composition forms a resist film having high absorption efficiency for EUV light and electron beams, which is effective for a reduction in the photon shot noise. The value A denotes, for the resist film, the absorption efficiency for EUV light and electron beams based on mass proportions.

$$A=([H]\times0.04+[C]\times1.0+[N]\times2.1+[O]\times3.6+[F]\times5.6+[S]\times1.5+[1]\times39.5)/([H]\times1+[C]\times12+[N]\times14+[O]\times16+[F]\times19+[S]\times32+[I]\times127) \quad \text{Formula (1):}$$

The value A is preferably 0.120 or more. The upper limit is not particularly limited; however, when the value A is excessively large, the resist film has lower transmittance for EUV light and electron beams and the optical image profile in the resist film deteriorates, so that a good pattern profile is less likely to be provided; thus, the value A is preferably 0.240 or less, more preferably 0.220 or less.

Note that, in Formula (1), [H] represents, relative to all the atoms of the whole solid content in the actinic ray-sensitive or radiation-sensitive resin composition, the molar ratio of hydrogen atoms derived from the whole solid content, [C] represents, relative to all the atoms of the whole solid content in the actinic ray-sensitive or radiation-sensitive resin composition, the molar ratio of carbon atoms derived from the whole solid content, [N] represents, relative to all the atoms of the whole solid content in the actinic ray-sensitive or radiation-sensitive resin composition, the molar ratio of nitrogen atoms derived from the whole solid content, [O] represents, relative to all the atoms of the whole solid content in the actinic ray-sensitive or radiation-sensitive resin composition, the molar ratio of oxygen atoms derived from the whole solid content, [F] represents, relative to all the atoms of the whole solid content in the actinic ray-sensitive or radiation-sensitive resin composition, the molar ratio of fluorine atoms derived from the whole solid content, [S] represents, relative to all the atoms of the whole solid content in the actinic ray-sensitive or radiation-sensitive resin composition, the molar ratio of sulfur atoms derived from the whole solid content, and [I] represents, relative to all the atoms of the whole solid content in the actinic ray-sensitive or radiation-sensitive resin composition, the molar ratio of iodine atoms derived from the whole solid content.

For example, when the resist composition includes an acid-decomposable resin, a photoacid generator, an acid diffusion control agent, and a solvent, the acid-decomposable resin, the photoacid generator, and the acid diffusion control agent correspond to the solid content. Thus, all the atoms of the whole solid content correspond to the total of all the atoms derived from the resin, all the atoms derived from the photoacid generator, and all the atoms derived from the acid diffusion control agent. For example, [H] represents, relative to all the atoms of the whole solid content, the molar ratio of hydrogen atoms derived from the whole solid content: on the basis of the above-described example, [H] represents the molar ratio of, relative to the total of all the atoms derived from the acid-decomposable resin, all the atoms derived from the photoacid generator, and all the atoms derived from the acid diffusion control agent, the total of the hydrogen atoms derived from the acid-decomposable resin, the hydrogen atoms derived from the photoacid generator, and the hydrogen atoms derived from the acid diffusion control agent.

The value A can be determined by, when the structures and contents of constituent components of the whole solid content in the resist composition are known, calculating the ratio of the numbers of atoms contained. Even when the constituent components are not known, for a resist film formed by evaporating the solvent component of the resist composition, an analysis method such as elemental analysis can be used to thereby determine the ratio of the numbers of constituent atoms.

Method for Forming Resist Film and Pattern

The pattern forming method using the actinic ray-sensitive or radiation-sensitive resin composition is not particularly limited in terms of procedures, but preferably has the following steps.

Step 1: a step of using an actinic ray-sensitive or radiation-sensitive resin composition produced by a method for producing an actinic ray-sensitive or radiation-sensitive resin composition according to the present invention, to form a resist film on a substrate Step 2: a step of exposing the resist film Step 3: a step of developing the exposed resist film using a developer Hereinafter, procedures of the steps will be described in detail.

Step 1: Resist Film Formation Step

The step 1 is a step of using the actinic ray-sensitive or radiation-sensitive resin composition to form a resist film on a substrate.

The definition of the actinic ray-sensitive or radiation-sensitive resin composition is the same as that described above.

The process of using the actinic ray-sensitive or radiation-sensitive resin composition to form, on a substrate, a resist film may be, for example, a process of applying the actinic ray-sensitive or radiation-sensitive resin composition onto the substrate.

Note that, prior to the application, the actinic ray-sensitive or radiation-sensitive resin composition is preferably, as needed, subjected to filtration through a filter. The filter preferably has a pore size of 0.1 μm or less, more preferably 0.05 μm or less, still more preferably 0.03 μm or less. The filter is preferably formed of polytetrafluoroethylene, polyethylene, or nylon.

The actinic ray-sensitive or radiation-sensitive resin composition can be applied onto a substrate (for example, formed of silicon and covered with silicon dioxide) as with substrates used for producing integrated circuit elements, by an appropriate coating process using a spinner or a coater, for example. The coating process is preferably spin-coating using a spinner. The spin-coating using a spinner is preferably performed at a rotation rate of 1000 to 3000 rpm.

After the application of the actinic ray-sensitive or radiation-sensitive resin composition, the substrate may be dried to form a resist film. Note that, as needed, as underlayers of the resist film, various underlying films (an inorganic film, an organic film, or an antireflection film) may be formed.

The drying process may be, for example, a process of performing heating to achieve drying. The heating can be performed using means included in an ordinary exposure device and/or an ordinary development device, or may alternatively be performed using a hot plate, for example. The heating temperature is preferably 80 to 150° C., more preferably 80 to 140° C., still more preferably 80 to 130° C. The heating time is preferably 30 to 1000 seconds, more preferably 60 to 800 seconds, still more preferably 60 to 600 seconds.

The film thickness of the resist film is not particularly limited, but is, from the viewpoint of enabling formation of more precise fine patterns, preferably 10 to 120 nm. In particular, in the case of EUV exposure, the film thickness of the resist film is more preferably 10 to 65 nm, still more preferably 15 to 50 nm. In the case of ArF liquid immersion exposure, the film thickness of the resist film is more preferably 10 to 120 nm, still more preferably 15 to 90 nm.

Note that, as an overlying layer of the resist film, a topcoat composition may be used to form a topcoat.

The topcoat composition preferably does not mix with the resist film, and can be uniformly applied, as an overlying layer of the resist film. The topcoat is not particularly limited; a publicly known topcoat can be formed by a publicly known process; for example, on the basis of descriptions of Paragraphs [0072] to [0082] in JP2014-059543A, a topcoat can be formed.

For example, a topcoat including a basic compound and described in JP2013-61648A is preferably formed on the resist film. Specific examples of the basic compound that can be included in the topcoat include basic compounds that may be included in the actinic ray-sensitive or radiation-sensitive resin composition.

The topcoat also preferably includes a compound including at least one group or bond selected from the group consisting of an ether bond, a thioether bond, a hydroxy group, a thiol group, a carbonyl bond, and an ester bond.

Step 2: Exposure Step

The step 2 is a step of exposing the resist film.

The exposure process may be a process of irradiating the formed resist film, through a predetermined mask, with an actinic ray or radiation.

Examples of the actinic ray or radiation include infrared light, visible light, ultraviolet light, far-ultraviolet light, extreme ultraviolet light, X-rays, and an electron beam; the actinic ray or radiation is preferably far-ultraviolet light having wavelengths of 250 nm or less, more preferably 220 nm or less, particularly preferably 1 to 200 nm; specific examples include KrF excimer laser (248 nm), ArF excimer laser (193 nm), $F_2$ excimer laser (157 nm), EUV (13.5 nm), X-rays, and an electron beam.

After the exposure, before development, baking (heating) is preferably performed. The baking accelerates the reaction in the exposed regions, to provide higher sensitivity and a better pattern profile.

The heating temperature is preferably 80 to 150° C., more preferably 80 to 140° C., still more preferably 80 to 130° C.

The heating time is preferably 10 to 1000 seconds, more preferably 10 to 180 seconds, still more preferably 30 to 120 seconds.

The heating can be performed using means included in an ordinary exposure device and/or an ordinary development device, and may alternatively be performed using a hot plate, for example.

This step is also referred to as post-exposure baking.

Step 3: Development Step

The step 3 is a step of using a developer, to develop the exposed resist film, to form a pattern.

The developer may be an alkali developer or a developer containing an organic solvent (hereafter, also referred to as organic-based developer).

Examples of the development process include a process of immersing, for a predetermined time, the substrate in a tank filled with the developer (dipping process), a process of puddling, with the developer, the surface of the substrate using surface tension and leaving the developer at rest for a predetermined time to achieve development (puddling process), a process of spraying the developer to the surface of the substrate (spraying process), and a process of scanning, at a constant rate, over the substrate rotated at a constant rate, a developer ejection nozzle to continuously eject the developer (dynamic dispensing process).

After the step of performing development, a step of performing exchange with another solvent to stop the development may be performed.

The development time is not particularly limited as long as the resin in the unexposed regions is sufficiently dissolved in the time, and is preferably 10 to 300 seconds, more preferably 20 to 120 seconds.

The temperature of the developer is preferably 0 to 50° C., more preferably 15 to 35° C.

As the alkali developer, an alkali aqueous solution including an alkali is preferably used. The type of the alkali aqueous solution is not particularly limited, but may be, for example, an alkali aqueous solution including a quaternary ammonium salt represented by tetramethylammonium hydroxide, an inorganic alkali, a primary amine, a secondary amine, a tertiary amine, an alcoholamine, or a cyclic amine. In particular, the alkali developer is preferably an aqueous solution of a quaternary ammonium salt represented by tetramethylammonium hydroxide (TMAH). To the alkali developer, an appropriate amount of an alcohol, a surfactant, or the like may be added. The alkali developer ordinarily preferably has an alkali concentration of 0.1 to 20 mass %. The alkali developer ordinarily preferably has a pH of 10.0 to 15.0.

The organic-based developer is preferably a developer containing at least one organic solvent selected from the group consisting of ketone-based solvents, ester-based solvents, alcohol-based solvents, amide-based solvents, ether-based solvents, and hydrocarbon-based solvents.

Such solvents may be mixed together, or such a solvent may be mixed with a solvent other than those described above or water. The developer as a whole has a moisture content of preferably less than 50 mass %, more preferably less than 20 mass %, still more preferably less than 10 mass %, particularly preferably contains substantially no moisture.

In the organic-based developer, the content of the organic solvent relative to the total amount of the developer is preferably 50 mass % or more and 100 mass % or less, more preferably 80 mass % or more and 100 mass % or less, still more preferably 90 mass % or more and 100 mass % or less, particularly preferably 95 mass % or more and 100 mass % or less.

Other Step

The pattern forming method preferably includes a step of, after the step 3, using a rinse liquid to perform rinsing.

After the development step using an alkali developer, in the rinsing step, the rinse liquid employed may be, for example, pure water. Note that, to the pure water, an appropriate amount of surfactant may be added.

To the rinse liquid, an appropriate amount of surfactant may be added.

After the development step using an organic-based developer, in the rinsing step, the rinse liquid employed is not particularly limited as long as it does not dissolve the pattern, and may be a solution including an ordinary organic solvent. The rinse liquid employed is preferably a rinse liquid containing at least one organic solvent selected from the group consisting of hydrocarbon-based solvents, ketone-based solvents, ester-based solvents, alcohol-based solvents, amide-based solvents, and ether-based solvents.

The process of performing the rinsing step is not particularly limited; examples include a process of continuously ejecting, onto the substrate rotated at a constant rate, the rinse liquid (spin-coating process), a process of immersing, in a tank filled with the rinse liquid, the substrate for a predetermined time (dipping process), and a process of spraying, to the surface of the substrate, the rinse liquid (spraying process).

The pattern forming method may include a heating step (Post Bake) performed after the rinsing step. In this step, baking removes the developer and the rinse liquid remaining between and within the patterns. In addition, this step also provides an effect of annealing the resist pattern to address the rough surface of the pattern. The heating step after the rinsing step is performed ordinarily at 40 to 250° C. (preferably 90 to 200° C.) for ordinarily 10 seconds to 3 minutes (preferably 30 seconds to 120 seconds).

The formed pattern may be used as a mask for subjecting the substrate to etching treatment. Specifically, the pattern formed in the step 3 may be used as a mask for processing the substrate (or the underlayer film and the substrate), to form a pattern in the substrate.

The process of processing the substrate (or the underlayer film and the substrate) is not particularly limited, but is preferably a process of using the pattern formed in the step 3 as a mask for subjecting the substrate (or the underlayer film and the substrate) to dry etching, to form a pattern in the substrate. The dry etching is preferably oxygen plasma etching.

The actinic ray-sensitive or radiation-sensitive resin composition and various materials used in the pattern forming method of this Specification (for example, the solvent, the developer, the rinse liquid, the antireflection film-forming composition, and the topcoat-forming composition) preferably do not include impurities such as metal. The content of impurities included in such materials is preferably 1 mass ppm (parts per million) or less, more preferably 10 mass ppb (parts per billion) or less, still more preferably 100 mass ppt (parts per trillion) or less, particularly preferably 10 mass ppt or less, most preferably 1 mass ppt or less. The lower limit is not particularly limited, but is preferably 0 mass ppt or more. Examples of the metallic impurities include Na, K, Ca, Fe, Cu, Mg, Al, Li, Cr, Ni, Sn, Ag, As, Au, Ba, Cd, Co, Pb, Ti, V, W, and Zn.

The process of removing, from the various materials, impurities such as metal may be, for example, filtration using a filter. The details of filtration using a filter are described in Paragraph [0321] in WO2020/004306A.

Examples of the process of reducing the amount of impurities such as metal included in the various materials include a process of selecting, as raw materials constituting the various materials, raw materials having lower metal content, a process of subjecting raw materials constituting the various materials to filtration using a filter, and a process of performing distillation under conditions under which contamination is minimized by, for example, lining the interior of the apparatuses with TEFLON (registered trademark).

Instead of the filtration using a filter, an adsorption material may be used to remove impurities; alternatively, the filtration using a filter may be combined with the use of an adsorption material. Such adsorption materials can be publicly known adsorption materials, and examples include inorganic adsorption materials such as silica gel and zeolite, and organic adsorption materials such as active carbon. In order to reduce the amount of impurities such as metal included in the various materials, ingress of metallic impurities in the production steps needs to be prevented. Whether or not metallic impurities are sufficiently removed from the production apparatuses can be determined by measuring the content of metallic components included in the washing liquid having been used for washing the production apparatuses. The content of metallic components included in the washing liquid having been used is preferably 100 mass ppt or less, more preferably 10 mass ppt or less, still more preferably 1 mass ppt or less. The lower limit is not particularly limited, but is preferably 0 mass ppt or more.

To organic treatment liquids such as the rinse liquid, in order to prevent electrostatic buildup and the subsequent electrostatic discharge causing failure of the chemical solution pipe and various parts (such as a filter, an O-ring, and a tube), a conductive compound may be added. The conductive compound is not particularly limited, but may be, for example, methanol. The amount of addition is not particularly limited, but is, from the viewpoint of maintaining preferred development performance or rinsing performance, preferably 10 mass % or less, more preferably 5 mass % or less. The lower limit is not particularly limited, but is preferably 0.01 mass % or more.

Examples of the chemical solution pipe include various pipes formed of SUS (stainless steel), or coated with polyethylene, polypropylene, or a fluororesin (such as polytetrafluoroethylene or a perfluoroalkoxy resin) treated so as to be antistatic. Similarly for the filter and the O-ring, polyethylene, polypropylene, or a fluororesin (such as polytetrafluoroethylene or a perfluoroalkoxy resin) treated so as to be antistatic can be used.

Method for Producing Electronic Device

This Specification also relates to a method for producing an electronic device, the method including the above-described pattern forming method, and an electronic device produced by the production method.

The electronic device of this Specification may be suitably mounted on electric or electronic devices (such as household appliances, OA (Office Automation), media-related devices, optical devices, and communication devices).

Method for Producing Onium Salt

The present invention also relates to a method for producing an onium salt, the method including a step (1) of passing a solution including an acid compound (CA) having a pKa of 2.0 or more through a column packed with an ion-exchange resin, and a step (2) of using the acid compound (CA) having passed through the column to produce an onium salt (C).

EXAMPLES

Hereinafter, the present invention will be described further in detail with reference to Examples. In the following Examples, materials, usage amounts, ratios, details of treatments, orders of treatments, and the like can be appropriately changed without departing from the spirit and scope of the present invention. Thus, the scope of the present invention should not be construed as being limited to the following Examples.

The following are compounds used in Examples and Comparative Examples.

Acid Compounds

As acid compounds, the following CH-1 to CH-10 and XH-1 were used. Me represents a methyl group.

CH-1

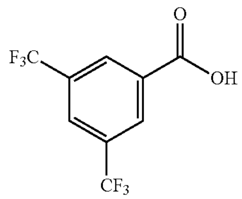

CH-2

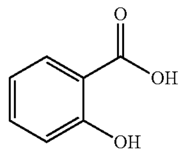

CH-3

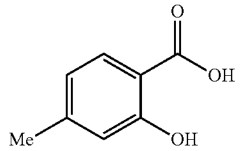

CH-4

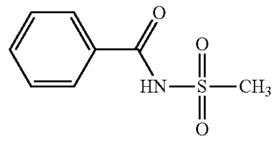

CH-5

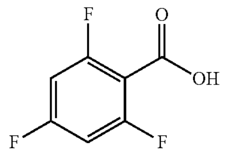

CH-6

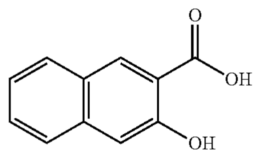

-continued

CH-7

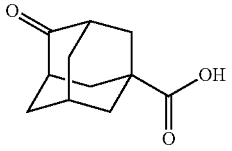

CH-8

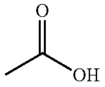

CH-9

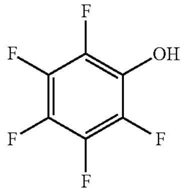

CH-10

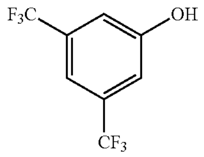

XH-1

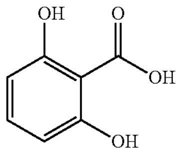

The pKa of CH-1 to CH-10 and XH-1 will be described in the following Table 1.

TABLE 1

| Acid compound | pKa |
|---|---|
| CH-1 | 3.34 |
| CH-2 | 3.01 |
| CH-3 | 3.17 |
| CH-4 | 4.86 |
| CH-5 | 2.28 |
| CH-6 | 3.02 |
| CH-7 | 4.42 |
| CH-8 | 4.79 |
| CH-9 | 5.50 |
| CH-10 | 7.96 |
| XH-1 | 1.30 |

As described in Table 1, CH-1 to CH-10 are the acid compounds (CA) having a pKa of 2.0 or more while XH-1 is not the acid compound (CA).

Resin (A)

As the resin (A), resins A-1 to A-15 were used.

Table 2 describes, for each of repeating units included in the resins, content (mol %), weight-average molecular weight (Mw), and dispersity (Mw/Mn). The content of each repeating unit is the ratio (molar ratio) of the repeating unit to all the repeating units included in each resin. The repeating units are described using the structures of the corresponding monomers.

The weight-average molecular weight (Mw) and dispersity (Mw/Mn) of the resin were measured by GPC (carrier: tetrahydrofuran (THF)) (polystyrene-equivalent molecular weight). The contents of the repeating units were measured by $^{13}$C-NMR (nuclear magnetic resonance).

M-1

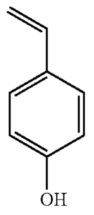

M-2

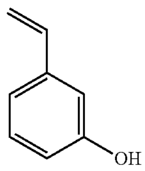

M-3

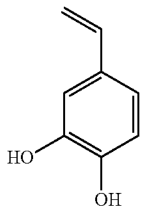

M-4

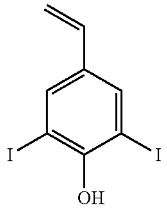

M-5

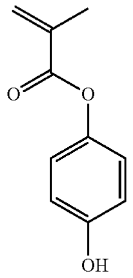

MP-1

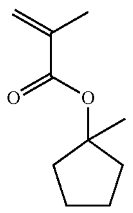

-continued
MP-2
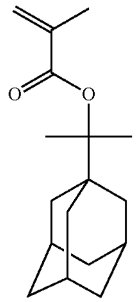
MP-3
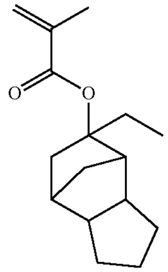
MP-4
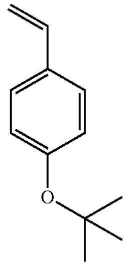
MP-5
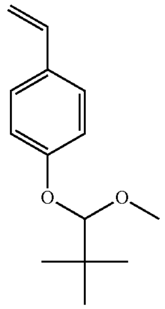
MP-6
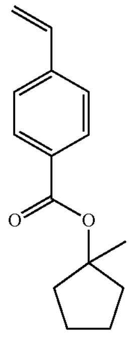
-continued
MP-7
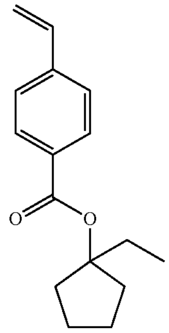
MP-8
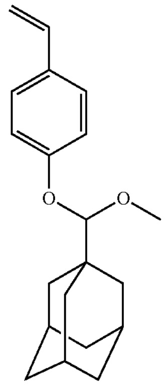
MS-1
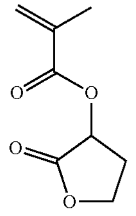
MS-2
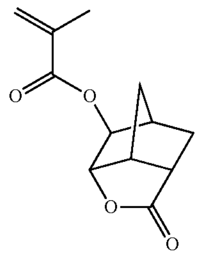
MS-3
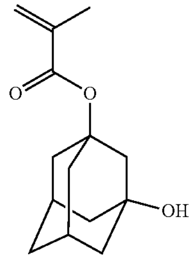

-continued
MA-1
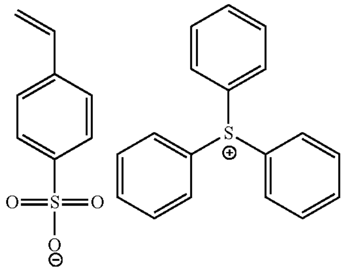
MA-2
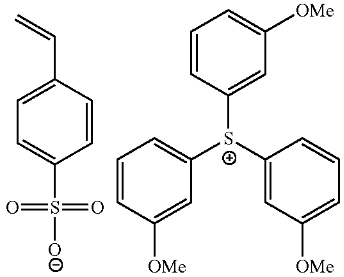
TABLE 2
| Resin (A) | Content of repeating unit 1 (mol %) | | Content of repeating unit 2 (mol %) | | Content of repeating unit 3 (mol %) | | Content of repeating unit 4 (mol %) | | Mw | Mw/Mn |
|---|---|---|---|---|---|---|---|---|---|---|
| A-1 | M-1 | 70 | MP-1 | 30 | — | — | — | — | 7000 | 1.70 |
| A-2 | M-1 | 65 | MP-2 | 30 | — | — | MA-1 | 5 | 8000 | 1.60 |
| A-3 | M-1 | 55 | MP-3 | 30 | — | — | MA-1 | 15 | 8000 | 1.75 |
| A-4 | M-2 | 55 | MP-4 | 45 | — | — | — | — | 8000 | 1.60 |
| A-5 | M-3 | 50 | MP-5 | 35 | MS-1 | 15 | — | — | 9000 | 1.75 |
| A-6 | M-4 | 70 | MP-6 | 30 | — | — | — | — | 8000 | 1.65 |
| A-7 | M-5 | 60 | MP-7 | 30 | MS-2 | 10 | — | — | 11000 | 1.60 |
| A-8 | M-1 | 40 | MP-1 | 40 | MS-3 | 10 | MA-2 | 10 | 10000 | 1.65 |
| A-9 | M-1 | 60 | MP-5 | 40 | — | — | — | — | 8000 | 1.60 |
| A-10 | M-1 | 60 | MP-7 | 35 | — | — | MA-1 | 5 | 12000 | 1.65 |
| A-11 | M-2 | 60 | MP-6 | 40 | — | — | — | — | 5000 | 1.65 |
| A-12 | M-1 | 75 | MP-8 | 25 | — | — | — | — | 4500 | 1.65 |
| A-13 | M-1 | 85 | MP-8 | 15 | — | — | — | — | 4500 | 1.65 |
| A-14 | M-1 | 85 | MP-1 | 15 | — | — | — | — | 7000 | 1.70 |
| A-15 | M-1 | 70 | MP-6 | 30 | — | — | — | — | 7000 | 1.60 |
Photoacid Generator (B)
As the photoacid generator (B), compounds B-1 to B-7 were used.
B-1
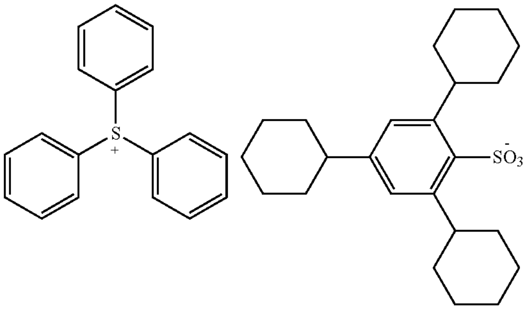
-continued
B-2
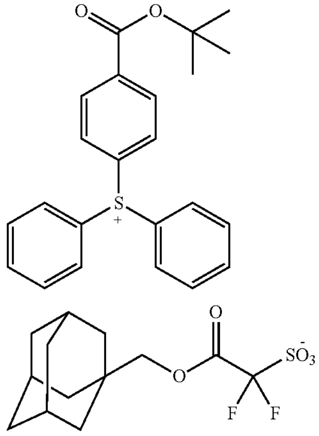

-continued

B-3

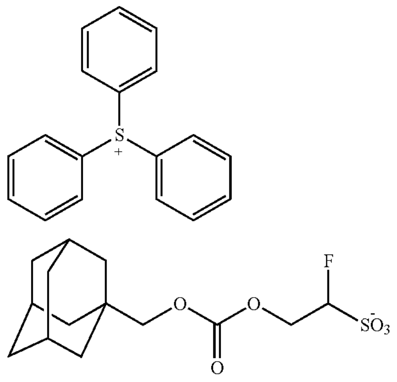

B-4

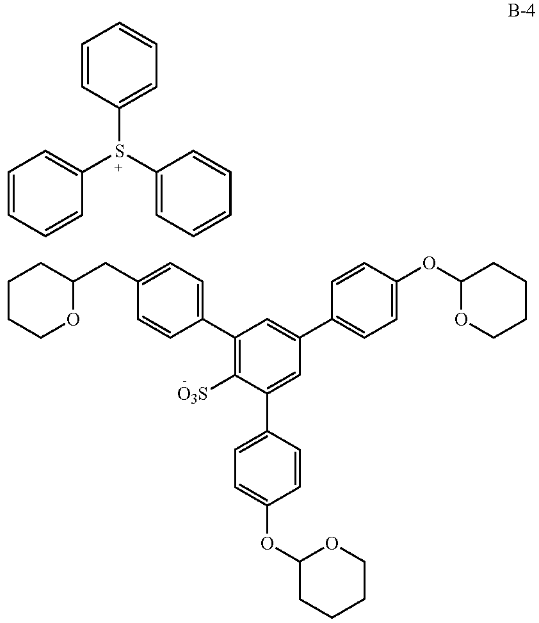

B-5

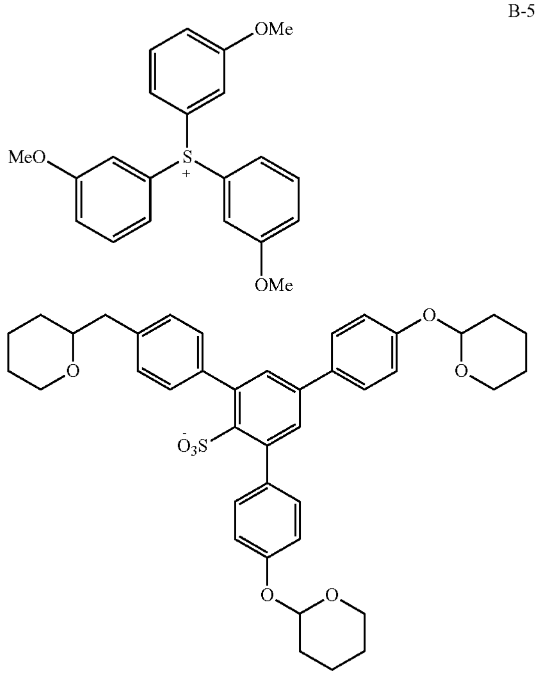

-continued

B-6

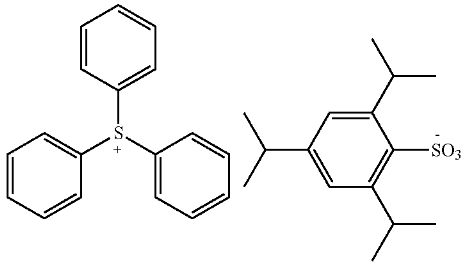

B-7

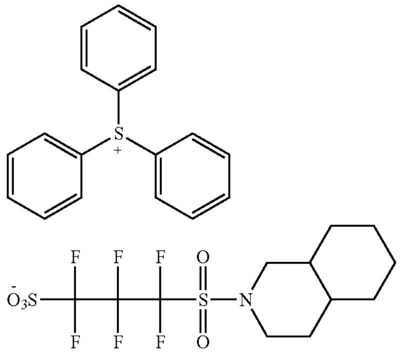

Hydrophobic Resin

As a hydrophobic resin, the following D-1 was used. Content (mol %) for each of repeating units included in D-1, weight-average molecular weight (Mw), and dispersity (Mw/Mn) are shown. The content of repeating unit is the ratio (molar ratio) of each repeating unit to all repeating units.

D-1

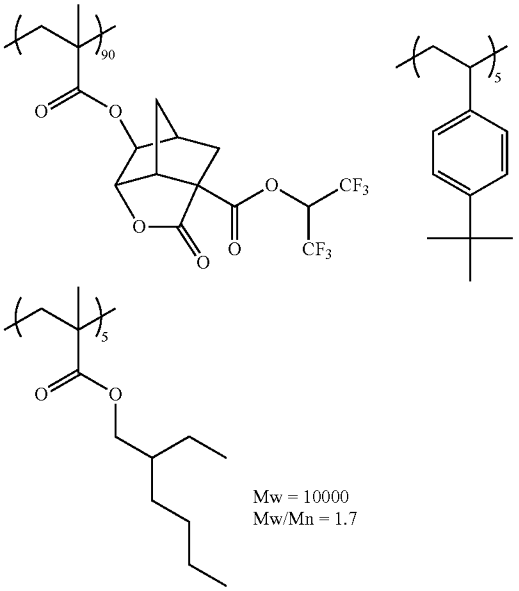

Mw = 10000
Mw/Mn = 1.7

Surfactants

As surfactants, the following W-1 to W-4 were used.

W-1: MEGAFACE R08 (manufactured by DIC Corporation)

W-2: MEGAFACE F176 (manufactured by DIC Corporation)

W-3: Troysol S-366 (manufactured by Troy Chemical Industries, Inc.)

W-4: PF656 (manufactured by OMNOVA Solutions Inc.)

Solvents

The following are solvents used.

S-1: propylene glycol monomethyl ether acetate (PGMEA)

S-2: propylene glycol monomethyl ether (PGME)

S-3: cyclohexanone

S-4: ethyl lactate (EL)

S-5: γ-butyrolactone

Onium Salts (Acid Diffusion Control Agents)

The following are the structures of onium salts. Me represent a methyl group.

C-1

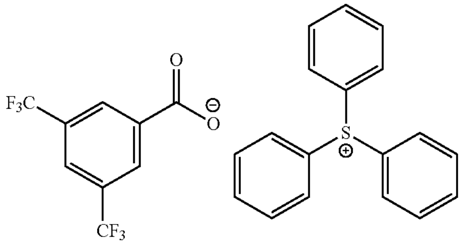

C-2

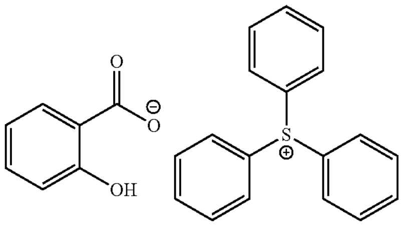

C-3

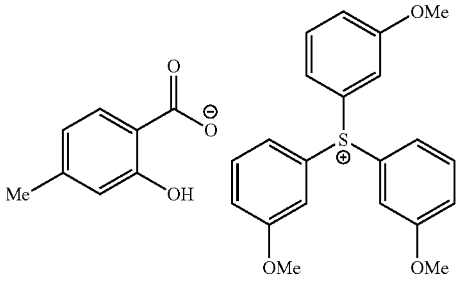

C-4

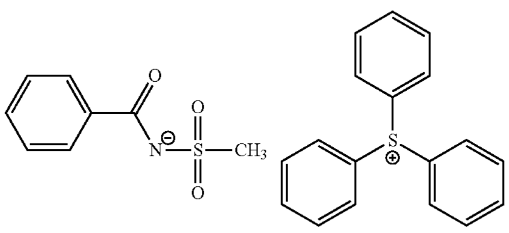

C-5

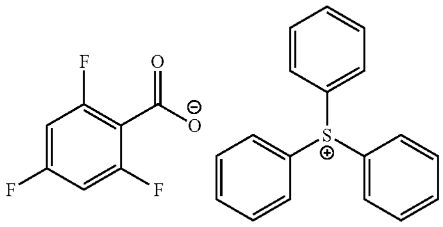

-continued

C-6

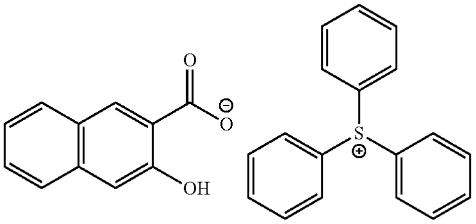

C-7

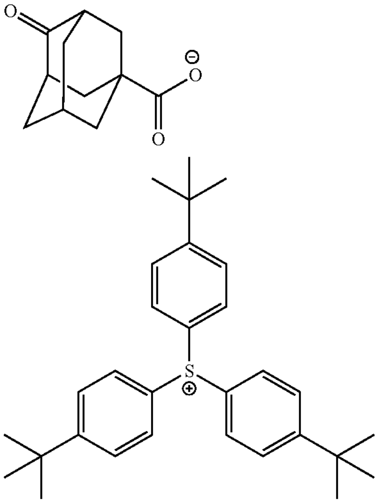

C-8

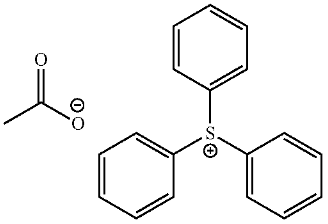

C-9

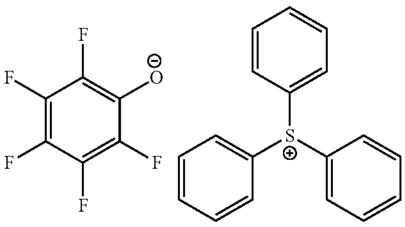

C-10

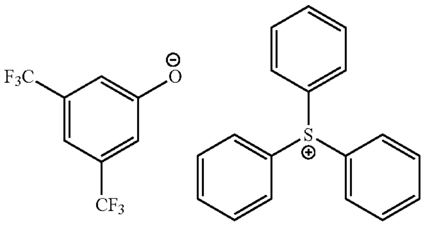

-continued

X-1

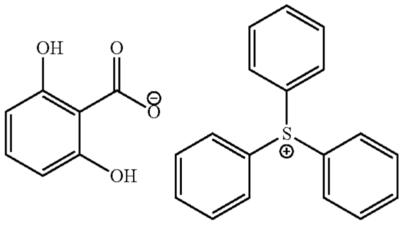

C-11

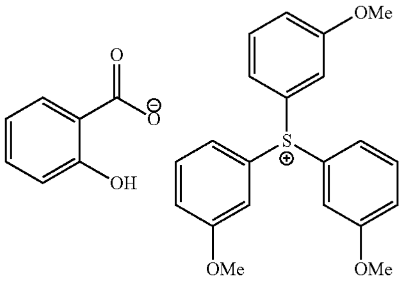

In Examples 1 to 42 and Comparative Example 3, a step (1) of passing a solution including an acid compound through a column packed with an ion-exchange resin and a step (2) of using the acid compound having been passed through the column to produce an onium salt were performed to produce onium salts.

As an example, procedures performed in Example 5 will be described.

Step (1): Purification of Acid Compound

A glass column was packed with 300 g of an ion-exchange resin (DIAION SK112L: manufactured by Mitsubishi Chemical Corporation) having been washed. Note that washing and packing of the ion-exchange resin were performed in the following manner. Into 500 ml of 0.1 mol/L hydrochloric acid, 300 g of the ion-exchange resin was placed and left for 30 minutes and packed into a glass column. Subsequently, 1000 g of distilled water was passed to exchange hydrochloric acid with distilled water, and 1000 g of methanol was further passed to exchange distilled water with methanol.

A solution provided by dissolving 30.0 g of the acid compound (CH-2) in 240 g of methanol was passed, at 23° C. at atmospheric pressure, through the column packed with the ion-exchange resin; subsequently 500 g of methanol was passed. The resultant solution was distilled under a reduced pressure to remove methanol; subsequently, 240 g of diisopropyl ether and 60 g of 1 mol/L hydrochloric acid were added, and a separation procedure was performed. To the organic layer, 60 g of distilled water was added, and a separation procedure was repeated four times. The solvent of the organic layer was distilled off under a reduced pressure; subsequently, 900 g of heptane was added and stirring at 23° C. was performed. This was filtered to obtain 25.0 g of the acid compound (CH-2).

Step (2): Production of Onium Salt

To 20.0 g of the acid compound (CH-2) obtained in the step (1), 532 g of methylene chloride was added. Subsequently, 246 g of a 20 mass % aqueous solution of triphenylsulfonium hydrogencarbonate was added, and stirring at 23° C. was performed for 30 minutes. The aqueous layer was removed; subsequently, 80 g of distilled water was added and a separation procedure was repeated four times. The solvent of the organic layer was distilled off under a reduced pressure; to the resultant solid, 796 g of acetonitrile was added and heated at 60° C. to achieve dissolution. Diisopropyl ether (223 g) was added and stirring at 23° C. was performed, the resultant solid was filtered, to obtain 41.6 g of the onium salt (C-2).

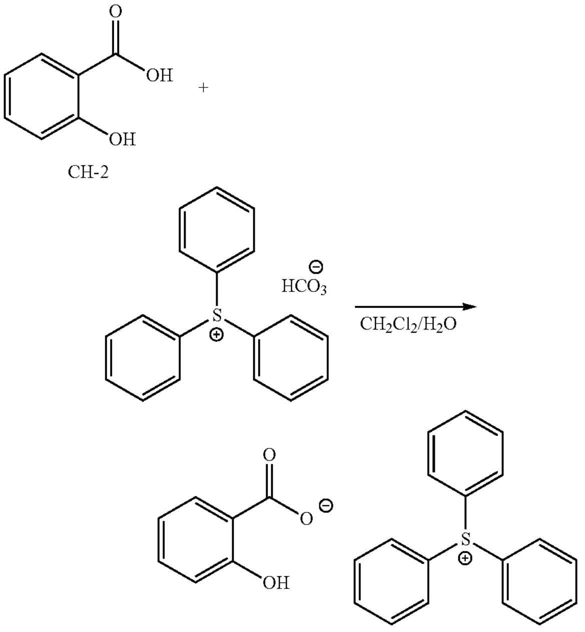

CH-2

C-2

Example 19, 22, 23, 26, 27, 29 to 32, 35, 38 to 40, and 42 were performed as with Example 5.

In Example 36, onium salts were produced as in Example 5 except that the triphenylsulfonium hydrogencarbonate was replaced by salts constituted by the the sulfonium cations of the onium salts (C-11) to be produced and a hydrogencarbonate ion.

In Example 37, onium salts were produced as in Example 5 except that in addition to the triphenylsulfonium hydrogencarbonate, salts constituted by the sulfonium cations of C-11 and a hydrogencarbonate ion were used.

In Examples 1, 2, 4, 6, 8 to 18, 20, 21, 24, 25, 28, 33, 34, and 41 and Comparative Example 3, onium salts were produced as in Example 5 except that the acid compound (CH-2) was replaced by acid compounds described in Table 3 and Table 4 below, and DIAION SK112L was replaced by ion-exchange resins described in Table 3 and Table 4 below.

In Examples 3, 7, 14, and 18, onium salts were produced as in Example 5 except that the acid compound (CH-2) was replaced by acid compounds described in Table 3 below, DIAION SK112L was replaced by ion-exchange resins described in Table 3 below, and the triphenylsulfonium hydrogencarbonate was replaced by salts constituted by the sulfonium cations of the onium salts (C-3 and C-7) to be produced and a hydrogencarbonate ion.

In Comparative Example 1, the purification using the ion-exchange resin in Example 1 was not performed.

In Comparative Example 2, instead of the purification using the ion-exchange resin in Example 1, washing using acid was performed. The washing using acid was performed in the following manner. The acid compound (CH-1) (30.0 g) was dissolved in 240 g of diisopropyl ether; subsequently, 60 g of 0.1 mol/L hydrochloric acid was added and a separation procedure was performed. This was repeated twice; subsequently, to the organic layer, 60 g of distilled water was added and a separation procedure was repeated four times. The solvent of the organic layer was distilled off under a reduced pressure; subsequently, 900 g of heptane was added and stirring at 23° C. was performed. This was filtered to obtain 25.0 g of the acid compound (CH-1).

In Comparative Example 4, instead of the purification of the acid compound using the ion-exchange resin in Example 1, purification of the onium salt (C-1) using an ion-exchange resin was performed.

The acid compounds used and the onium salts produced in Examples and Comparative Examples are described in Table 3 and Table 4 below. Table 3 and Table 4 also describes the types of the ion-exchange resins used, values (X1−X2) obtained by subtracting, from the pKa (X1) of an acid compound, the pKa (X2) of the ion-exchange group of an ion-exchange resin, and whether or not the step (1) (purification of an acid compound using an ion-exchange resin) was performed.

TABLE 3

| | Acid compound used | Ion-exchange resin used | pKa difference (X1 − X2) between acid compound and ion-exchange group | Step (1) purification of acid compound using ion-exchange resin | Onium salt produced |
|---|---|---|---|---|---|
| Example 1 | CH-1 | DIAION SK1BH | 3.8 | Performed | C-1 |
| Example 2 | CH-5 | DIAION SK1BH | 2.7 | Performed | C-5 |
| Example 3 | CH-3 | DIAION SK1BH | 3.6 | Performed | C-3 |
| Example 4 | CH-4 | Diaion WK10 | −0.10 | Performed | C-4 |
| Example 5 | CH-2 | DIAION SK112L | 3.5 | Performed | C-2 |
| Example 6 | CH-6 | DIAION SK1BH | 3.5 | Performed | C-6 |
| Example 7 | CH-7 | DIAION SK1BH | 4.9 | Performed | C-7 |
| Example 8 | CH-8 | DIAION SK1BH | 5.2 | Performed | C-8 |
| Example 9 | CH-9 | Diaion WK10 | 0.6 | Performed | C-9 |
| Example 10 | CH-10 | Diaion WK10 | 3.0 | Performed | C-10 |
| Comparative Example 1 | CH-1 | None | — | None | C-1 |
| Comparative Example 2 | CH-1 | None (washing using acid) | — | None (washing using acid) | C-1 |
| Comparative Example 3 | XH-1 | DIAION SK1BH | 1.8 | Performed | X-1 |
| Comparative Example 4 | CH-1 | DIAION SK1BH | 3.8 | None (purification of C-1) | C-1 |
| Example 11 | CH-10 | Diaion WK10 | 3.0 | Performed | C-10 |
| Example 12 | CH-9 | Diaion WK10 | 0.6 | Performed | C-9 |
| Example 13 | CH-8 | DIAION SK1BH | 5.2 | Performed | C-8 |
| Example 14 | CH-7 | DIAION SK1BH | 4.9 | Performed | C-7 |
| Example 15 | CH-6 | DIAION SK1BH | 3.5 | Performed | C-6 |
| Example 16 | CH-5 | DIAION SK1BH | 2.7 | Performed | C-5 |
| Example 17 | CH-4 | Diaion WK10 | −0.10 | Performed | C-4 |
| Example 18 | CH-3 | DIAION SK1BH | 3.6 | Performed | C-3 |
| Example 19 | CH-2 | DIAION SK112L | 3.5 | Performed | C-2 |
| Example 20 | CH-1 | DIAION SK1BH | 3.8 | Performed | C-1 |

TABLE 4

| | Acid compound used | Ion-exchange resin used | pKa difference (X1 − X2) between acid compound and ion-exchange group | Step (1) purification of acid compound using ion-exchange resin | Onium salt produced |
|---|---|---|---|---|---|
| Example 21 | CH-1 | DIAION SK1BH | 3.8 | Performed | C-1 |
| Example 22 | CH-2 | DIAION SK112L | 3.5 | Performed | C-2 |
| Example 23 | CH-2 | DIAION SK112L | 3.5 | Performed | C-2 |
| Example 24 | CH-3 | DIAION SK1BH | 3.6 | Performed | C-3 |
| Example 25 | CH-4 | Diaion WK10 | −0.10 | Performed | C-4 |
| Example 26 | CH-2 | DIAION SK112L | 3.5 | Performed | C-2 |
| Example 27 | CH-2 | DIAION SK112L | 3.5 | Performed | C-2 |
| Example 28 | CH-6 | DIAION SK1BH | 3.5 | Performed | C-6 |
| Example 29 | CH-2 | DIAION SK112L | 3.5 | Performed | C-2 |
| Example 30 | CH-2 | DIAION SK112L | 3.5 | Performed | C-2 |
| Example 31 | CH-2 | DIAION SK112L | 3.5 | Performed | C-2 |
| Example 32 | CH-2 | DIAION SK112L | 3.5 | Performed | C-2 |
| Example 33 | CH-6 | DIAION SK1BH | 3.5 | Performed | C-6 |
| Example 34 | CH-2/CH-6 | DIAION SK112L/ DIAION SK1BH | 3.5/3.5 | Performed | C-2/C-6 |
| Example 35 | CH-2 | DIAION SK112L | 3.5 | Performed | C-2 |
| Example 36 | CH-2 | DIAION SK112L | 3.5 | Performed | C-11 |
| Example 37 | CH-2 | DIAION SK112L | 3.5 | Performed | C-2/C-11 |
| Example 38 | CH-2 | DIAION SK112L | 3.5 | Performed | C-2 |
| Example 39 | CH-2 | DIAION SK112L | 3.5 | Performed | C-2 |
| Example 40 | CH-2 | DIAION SK112L | 3.5 | Performed | C-2 |
| Example 41 | CH-1 | DIAION SK1BH | 3.8 | Performed | C-1 |
| Example 42 | CH-2 | DIAION SK112L | 3.5 | Performed | C-2 |

The types of the ion-exchange groups of the ion-exchange resins used and the pKa and the degree of crosslinking of the ion-exchange groups are described in Table 5 below. The ion-exchange resins are all manufactured by Mitsubishi Chemical Corporation.

TABLE 5

| Product name | Type of ion-exchange group | pKa of ion-exchange group | Degree of crosslinking |
|---|---|---|---|
| DIAION SK1BH | Sulfonic group | −0.45 | 10% |
| Diaion WK10 | Carboxylic group | 4.94 | 10% |
| DIAION SK112L | Sulfonic group | −0.45 | 12% |

Step (3): Preparation of Resist Composition

Components described in Table 6 and Table 7 were dissolved in a solvent described in Table 6 and Table 7 to prepare a solution; this was filtered through a polyethylene filter having a pore size of 0.03 m to prepare a resist composition.

In Table 6 and Table 7, the contents (mass %) of the resin (A), the photoacid generator (B), the onium salt (acid diffusion control agent), and the surfactant mean mass-based content ratios relative to the total solid content of the resist composition. As such onium salts, onium salts produced by the above-described methods were used.

Such resist compositions were prepared to have a solid content concentration of 3.0 mass %.

TABLE 6

| | | Resin (A) | | Photoacid generator (B) | | Onium salt | | Surfactant | | Solvent | |
|---|---|---|---|---|---|---|---|---|---|---|---|
| | Resist composition | Type | Content (mass %) | Type | Content (mass %) | Type | Content (mass %) | Type | Content (mass %) | Type | Mixing ratio (mass ratio) |
| Example 1 | R-1 | A-1 | 80.0 | B-1 | 10.0 | C-1 | 10.0 | — | — | S-1/S-2/S-4 | 20/20/60 |
| Example 2 | R-2 | A-2 | 80.0 | — | — | C-5 | 20.0 | — | — | S-1/S-2/S-4 | 20/20/60 |
| Example 3 | R-3 | A-3 | 80.0 | — | — | C-3 | 20.0 | — | — | S-1/S-2/S-4 | 20/20/60 |
| Example 4 | R-4 | A-4 | 75.0 | B-1 | 15.0 | C-4 | 10.0 | — | — | S-1/S-2/S-4 | 20/20/60 |
| Example 5 | R-5 | A-5 | 59.9 | B-1 | 20.0 | C-2 | 20.0 | W-1 | 0.10 | S-1/S-2/S-4 | 20/20/60 |
| Example 6 | R-6 | A-6 | 79.9 | B-2 | 10.0 | C-6 | 10.0 | W-2 | 0.10 | S-1/S-2/S-3 | 40/40/20 |
| Example 7 | R-7 | A-7 | 84.9 | B-3 | 10.0 | C-7 | 5.0 | W-3 | 0.10 | S-1/S-2/S-3 | 40/40/20 |
| Example 8 | R-8 | A-8 | 74.9 | — | — | C-8 | 25.0 | W-4 | 0.10 | S-1/S-2/S-5 | 50/40/10 |
| Example 9 | R-9 | A-9 | 80.0 | B-4 | 10.0 | C-9 | 10.0 | — | — | S-1/S-2/S-5 | 50/40/10 |
| Example 10 | R-10 | A-10 | 80.0 | B-1 | 5.0 | C-10 | 15.0 | — | — | S-1/S-2/S-4 | 20/20/60 |
| Comparative Example 1 | R-11 | A-1 | 80.0 | B-1 | 10.0 | C-1 | 10.0 | — | — | S-1/S-2/S-4 | 20/20/60 |
| Comparative Example 2 | R-12 | A-1 | 80.0 | B-1 | 10.0 | C-1 | 10.0 | — | — | S-1/S-2/S-4 | 20/20/60 |
| Comparative Example 3 | R-13 | A-1 | 80.0 | B-1 | 10.0 | X-1 | 10.0 | — | — | S-1/S-2/S-4 | 20/20/60 |
| Comparative Example 4 | R-14 | A-1 | 80.0 | B-1 | 10.0 | C-1 | 10.0 | — | — | S-1/S-2/S-4 | 20/20/60 |
| Example 11 | R-15 | A-6 | 75.0 | B-1 | 10.0 | C-10 | 15.0 | — | — | S-1/S-2 | 80/20 |
| Example 12 | R-16 | A-7 | 80.0 | B-2 | 10.0 | C-9 | 10.0 | — | — | S-1/S-2 | 80/20 |
| Example 13 | R-17 | A-8 | 65.0 | B-3 | 10.0 | C-8 | 25.0 | — | — | S-1/S-2 | 80/20 |
| Example 14 | R-18 | A-9 | 85.0 | B-4 | 10.0 | C-7 | 5.0 | — | — | S-1/S-2 | 80/20 |
| Example 15 | R-19 | A-10 | 90.0 | — | — | C-6 | 10.0 | — | — | S-1/S-2 | 80/20 |
| Example 16 | R-20 | A-6 | 70.0 | B-1 | 10.0 | C-5 | 20.0 | — | — | S-1/S-2 | 80/20 |
| Example 17 | R-21 | A-7 | 80.0 | B-2 | 10.0 | C-4 | 10.0 | — | — | S-1/S-2 | 80/20 |
| Example 18 | R-22 | A-8 | 70.0 | B-3 | 10.0 | C-3 | 20.0 | — | — | S-1/S-2 | 80/20 |
| Example 19 | R-23 | A-9 | 80.0 | B-4 | 10.0 | C-2 | 10.0 | — | — | S-1/S-2 | 80/20 |
| Example 20 | R-24 | A-10 | 90.0 | — | — | C-1 | 10.0 | — | — | S-1/S-2 | 80/20 |

TABLE 7

| | | Resin (A) | | Photoacid generator (B) | | Onium salt | |
|---|---|---|---|---|---|---|---|
| | Resist composition | Type | Content (mass %) | Type | Content (mass %) | Type | Content (mass %) |
| Example 21 | R-25 | A-11 | 75.0 | B-2 | 15.0 | C-1 | 10.0 |
| Example 22 | R-26 | A-10 | 80.0 | — | — | C-2 | 20.0 |
| Example 23 | R-27 | A-12 | 80.0 | B-4 | 10.0 | C-2 | 10.0 |
| Example 24 | R-28 | A-4 | 80.0 | B-4 | 10.0 | C-3 | 10.0 |
| Example 25 | R-29 | A-11 | 85.0 | B-2 | 10.0 | C-4 | 5.0 |
| Example 26 | R-30 | A-1 | 80.0 | B-4 | 10.0 | C-2 | 10.0 |
| Example 27 | R-31 | A-12 | 70.0 | B-4 | 10.0 | C-2 | 10.0 |
| Example 28 | R-32 | A-12 | 80.0 | B-4 | 10.0 | C-6 | 10.0 |
| Example 29 | R-33 | A-9 | 70.0 | B-4 | 15.0 | C-2 | 15.0 |
| Example 30 | R-34 | A-12 | 70.0 | B-4 | 15.0 | C-2 | 15.0 |
| Example 31 | R-35 | A-1 | 70.0 | B-4 | 15.0 | C-2 | 15.0 |
| Example 32 | R-36 | A-1 | 60.0 | B-4 | 15.0 | C-2 | 15.0 |
| Example 33 | R-37 | A-12 | 70.0 | B-4 | 15.0 | C-6 | 15.0 |
| Example 34 | R-38 | A-12 | 80.0 | B-4 | 10.0 | C-2/C-6 | 5.0/5.0 |
| Example 35 | R-39 | A-15 | 80.0 | B-4 | 10.0 | C-2 | 10.0 |
| Example 36 | R-40 | A-15 | 80.0 | B-5 | 10.0 | C-11 | 10.0 |

TABLE 7-continued

| | | | | | | | |
|---|---|---|---|---|---|---|---|
| Example 37 | R-41 | A-15 | 80.0 | B-5 | 10.0 | C-2/C-11 | 5.0/5.0 |
| Example 38 | R-42 | A-15 | 80.0 | B-4/B-6 | 5.0/5.0 | C-2 | 10.0 |
| Example 39 | R-43 | A-15 | 80.0 | B-4/B-7 | 5.0/5.0 | C-2 | 10.0 |
| Example 40 | R-44 | A-12/A-13 | 50.0/30.0 | B-4 | 10.0 | C-2 | 10.0 |
| Example 41 | R-45 | A-1/A-14 | 40.0/40.0 | B-1 | 10.0 | C-1 | 10.0 |
| Example 42 | R-46 | A-1/A-14 | 40.0/40.0 | B-4 | 10.0 | C-2 | 10.0 |

| | Hydrophobic resin | | Surfactant | | Solvent | |
|---|---|---|---|---|---|---|
| | Type | Content (mass %) | Type | Content (mass %) | Type | Mixing ratio (mass ratio) |
| Example 21 | — | — | — | — | S-1/S-2/S-4 | 20/20/60 |
| Example 22 | — | — | — | — | S-1/S-2/S-4 | 20/20/60 |
| Example 23 | — | — | — | — | S-1/S-2 | 80/20 |
| Example 24 | — | — | — | — | S-1/S-2 | 80/20 |
| Example 25 | — | — | — | — | S-1/S-2 | 80/20 |
| Example 26 | — | — | — | — | S-1/S-2 | 80/20 |
| Example 27 | D-1 | 10.0 | — | — | S-1/S-2 | 80/20 |
| Example 28 | — | — | — | — | S-1/S-2 | 80/20 |
| Example 29 | — | — | — | — | S-1/S-2/S-5 | 60/30/10 |
| Example 30 | — | — | — | — | S-1/S-2/S-5 | 60/30/10 |
| Example 31 | — | — | — | — | S-1/S-2/S-5 | 60/30/10 |
| Example 32 | D-1 | 10.0 | — | — | S-1/S-2/S-5 | 60/30/10 |
| Example 33 | — | — | — | — | S-1/S-2/S-5 | 60/30/10 |
| Example 34 | — | — | — | — | S-1/S-2/S-5 | 60/30/10 |
| Example 35 | — | — | — | — | S-1/S-2/S-5 | 60/30/10 |
| Example 36 | — | — | — | — | S-1/S-2/S-5 | 60/30/10 |
| Example 37 | — | — | — | — | S-1/S-2/S-5 | 60/30/10 |
| Example 38 | — | — | — | — | S-1/S-2/S-5 | 60/30/10 |
| Example 39 | — | — | — | — | S-1/S-2/S-5 | 60/30/10 |
| Example 40 | — | — | — | — | S-1/S-2 | 80/20 |
| Example 41 | — | — | — | — | S-1/S-2 | 80/20 |
| Example 42 | — | — | — | — | S-1/S-2 | 80/20 |

Application of Resist Composition

An 8-inch wafer on which Cr oxynitride was vapor-deposited (wafer used for an ordinary photo mask blank and having been subjected to the shielding-film treatment) was prepared.

Onto the 8-inch wafer, a spin-coater Mark 8 manufactured by Tokyo Electron Ltd. was used to apply the resist composition; drying at 120° C. for 600 seconds on a hot plate was performed, to obtain a resist film having a film thickness of 100 nm. Thus, a resist-coated wafer was obtained.

EB Exposure and Development

The resist film obtained above was irradiated to form a pattern using an electron-beam lithography apparatus (manufactured by ADVANTEST CORPORATION; F7000S, acceleration voltage: 50 keV). After the irradiation, heating at 100° C. for 600 seconds on a hot plate was performed; immersion using a 2.38 mass % aqueous solution of tetramethylammonium hydroxide (TMAH) for 60 seconds was performed; subsequently, rinsing with water for 30 seconds and drying were performed. In this way, on the 8-inch wafer, a resist pattern was formed.

Note that the exposure using the electron-beam irradiation apparatus (F7000S) was performed as a single-beam process; however, exposure by a multi-beam process of simultaneous scanning using a plurality of single beams is also expected to provide similar evaluation results.

Etching

The 8-inch wafer on which the resist pattern was formed was subjected to dry etching to form a hard mask pattern. In the dry etching, as the etching gas, a fluorine-based gas ($SF_6$) was used and the etching time was set to 20 seconds.

Evaluation

The obtained pattern was evaluated in the following manner in terms of post-etching LWR performance.

Sensitivity

The irradiation energy for resolving a 1:1 line and space pattern having a line width of 50 nm was defined as sensitivity (Eop).

Post-Etching LWR Performance

The post-etching LWR (line width roughness) was determined in the following manner: for the line and space pattern (line:space=1:1) formed at the Eop and having a line width of 50 nm, at randomly selected 50 points in a 0.5 μm region in the longitudinal direction, line widths were measured; the standard deviation (σ) thereof was determined and 3σ (nm) was calculated. The smaller the value of 3σ, the higher the post-etching LWR performance. The values of 3σ are described in Table 8 and Table 9.

TABLE 8

| | Post-etching LWR performance 3σ [nm] |
|---|---|
| Example 1 | 4.2 |
| Example 2 | 4.4 |
| Example 3 | 4.2 |
| Example 4 | 4.5 |
| Example 5 | 4.3 |
| Example 6 | 4.1 |
| Example 7 | 4.2 |
| Example 8 | 4.2 |
| Example 9 | 4.4 |
| Example 10 | 4.2 |
| Comparative Example 1 | 6.0 |
| Comparative Example 2 | 5.4 |
| Comparative Example 3 | 6.2 |
| Comparative Example 4 | 8.0 |
| Example 11 | 4.3 |
| Example 12 | 4.4 |
| Example 13 | 4.1 |
| Example 14 | 4.3 |
| Example 15 | 4.1 |

TABLE 8-continued

| | Post-etching LWR performance 3σ [nm] |
|---|---|
| Example 16 | 4.3 |
| Example 17 | 4.5 |
| Example 18 | 4.1 |
| Example 19 | 4.2 |
| Example 20 | 4.1 |

TABLE 9

| | Post-etching LWR performance 3σ [nm] |
|---|---|
| Example 21 | 4.1 |
| Example 22 | 4.2 |
| Example 23 | 4.1 |
| Example 24 | 4.1 |
| Example 25 | 4.5 |
| Example 26 | 4.1 |
| Example 27 | 4.0 |
| Example 28 | 4.1 |
| Example 29 | 4.1 |
| Example 30 | 4.0 |
| Example 31 | 4.1 |
| Example 32 | 4.2 |
| Example 33 | 4.0 |
| Example 34 | 4.0 |
| Example 35 | 4.1 |
| Example 36 | 4.1 |
| Example 37 | 4.0 |
| Example 38 | 4.1 |
| Example 39 | 4.0 |
| Example 40 | 4.1 |
| Example 41 | 4.2 |
| Example 42 | 4.2 |

As is clear from the results in Table 8 and Table 9, Examples 1 to 42 have higher post-etching LWR performance than Comparative Examples 1 to 4.

What is claimed is:

1. A method for producing an actinic ray-sensitive or radiation-sensitive resin composition, the method comprising:

passing a solution including an acid compound (CA) having a pKa of 2.0 or more, through a column packed with an ion-exchange resin;

producing an onium salt (C) by using the acid compound (CA) having been passed through the column; and mixing together the onium salt (C) and a resin (A) that undergoes an increase in polarity due to action of acid.

2. The method for producing an actinic ray-sensitive or radiation-sensitive resin composition according to claim 1, wherein the ion-exchange resin has, as an ion-exchange group, a strongly acidic cation-exchange group.

3. The method for producing an actinic ray-sensitive or radiation-sensitive resin composition according to claim 2, wherein the strongly acidic cation-exchange group is a sulfonic group.

4. The method for producing an actinic ray-sensitive or radiation-sensitive resin composition according to claim 1, wherein the acid compound (CA) has a pKa of 3.0 or more.

5. The method for producing an actinic ray-sensitive or radiation-sensitive resin composition according to claim 1, wherein the acid compound (CA) is a carboxylic acid or a phenol.

6. The method for producing an actinic ray-sensitive or radiation-sensitive resin composition according to claim 1, wherein the acid compound (CA) is a compound represented by General formula (CA1) or (CA2) below, (CA1)

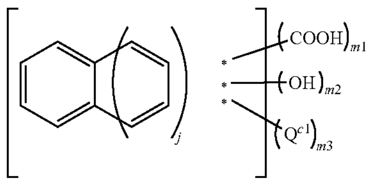

in General formula (CA1), j represents 0 or 1, $Q^{C1}$ represents a substituent, m1 and m2 each independently represent 0 or 1, m3 represents an integer of 0 or more and (6+2j−m1−m2) or less, a sum of m1 and m2 is 1 or 2, and

*'s each represent a direct bond connecting to the aromatic hydrocarbon described in General formula (CA1), and (CA2)

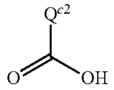

in General formula (CA2), $Q^{C2}$ represents an alkyl group or a cycloalkyl group.

7. The method for producing an actinic ray-sensitive or radiation-sensitive resin composition according to claim 1, wherein a value provided by subtracting, from the pKa of the acid compound (CA), a pKa of an ion-exchange group of the ion-exchange resin is 3.0 or more.

8. The method for producing an actinic ray-sensitive or radiation-sensitive resin composition according to claim 1, wherein the ion-exchange resin has a degree of crosslinking of 10% or less.

9. The method for producing an actinic ray-sensitive or radiation-sensitive resin composition according to claim 1, wherein the actinic ray-sensitive or radiation-sensitive resin composition includes the onium salt (C) in an amount of 10 mass % or more relative to a total solid content.

10. The method for producing an actinic ray-sensitive or radiation-sensitive resin composition according to claim 1, wherein the actinic ray-sensitive or radiation-sensitive resin composition further contains a compound (B) that generates acid in response to irradiation with an actinic ray or radiation, and the actinic ray-sensitive or radiation-sensitive resin composition has a mass-based content $A_C$ of the onium salt (C) and a mass-based content $A_B$ of the compound (B), and satisfies $A_C$:$A_B$=1:4 to 4:1.

11. The method for producing an actinic ray-sensitive or radiation-sensitive resin composition according to claim 1, wherein the resin (A) has at least one selected from the group consisting of a repeating unit represented by General formula (A1) below, a repeating unit represented by General formula (A2) below, and a repeating unit represented by General formula (A3) below, (A1)

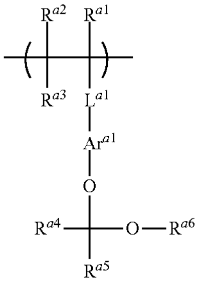

(A2)

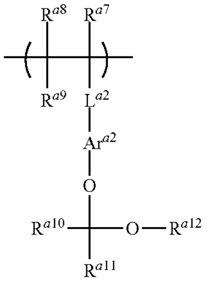

(A3)

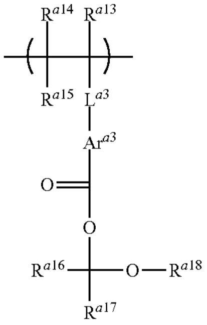

in General formula (A1), $R^{a1}$, $R^{a2}$, and $R^{a3}$ each independently represent a hydrogen atom, an alkyl group, a cycloalkyl group, a halogen atom, a cyano group, or an alkoxycarbonyl group, $L^{a1}$ represents a single bond or a divalent linking group, $Ar^{a1}$ represents an aromatic ring group, $R^{a4}$ represents a hydrogen atom, an alkyl group, a cycloalkyl group, an aryl group, an aralkyl group, or an alkenyl group, $R^{a5}$ and $R^{a6}$ each independently represent an alkyl group, a cycloalkyl group, an aryl group, an aralkyl group, or an alkenyl group, $R^{a4}$ and $R^{a5}$ may be linked together to form a ring, and $Ar^{a1}$ may be linked with $R^{a3}$ or $R^{a4}$ to form a ring, in General formula (A2), $R^{a7}$, $R^{a8}$, and $R^{a9}$ each independently represent a hydrogen atom, an alkyl group, a cycloalkyl group, a halogen atom, a cyano group, or an alkoxycarbonyl group, $L^{a2}$ represents a single bond or a divalent linking group, $Ar^{a2}$ represents an aromatic ring group, $R^{a10}$, $R^{a11}$, and $R^{a12}$ each independently represent an alkyl group, a cycloalkyl group, an aryl group, an aralkyl group, or an alkenyl group, and two of $R^{a10}$, $R^{a11}$, and $R^{a12}$ may be linked together to form a ring, and in General formula (A3), $R^{a13}$, $R^{a14}$, and $R^{a15}$ each independently represent a hydrogen atom, an alkyl group, a cycloalkyl group, a halogen atom, a cyano group, or an alkoxycarbonyl group, $L^{a3}$ represents a single bond or a divalent linking group, $Ar^{a3}$ represents an aromatic ring group, $R^{a16}$, $R^{a17}$, and $R^{a18}$ each independently represent an alkyl group, a cycloalkyl group, an aryl group, an aralkyl group, or an alkenyl group, and two of $R^{a16}$, $R^{a17}$, and $R^{a18}$ may be linked together to form a ring.

12. The method for producing an actinic ray-sensitive or radiation-sensitive resin composition according to claim 1, wherein the resin (A) has a repeating unit having a group that generates acid in response to irradiation with an actinic ray or radiation.

13. A pattern forming method comprising forming a resist film on a substrate by an actinic ray-sensitive or radiation-sensitive resin composition produced by the following method for producing an actinic ray-sensitive or radiation-sensitive resin composition, exposing the resist film, and developing the exposed resist film by a developer, said method for producing an actinic ray-sensitive or radiation-sensitive resin composition comprising the following steps:

passing a solution including an acid compound (CA) having a pKa of 2.0 or more, through a column packed with an ion-exchange resin;

producing an onium salt (C) by using the acid compound (CA) having been passed through the column; and mixing together the onium salt (C) and a resin (A) that undergoes an increase in polarity due to action of acid.

14. A method for producing an electronic device, the method comprising the pattern forming method according to claim 13.

15. A method for producing an onium salt, the method comprising:

passing a solution including an acid compound (CA) having a pKa of 2.0 or more, through a column packed with an ion-exchange resin; and producing an onium salt (C) by using the acid compound (CA) having been passed through the column.

* * * * *